US011066438B2

(12) United States Patent
Barbut et al.

(10) Patent No.: US 11,066,438 B2
(45) Date of Patent: Jul. 20, 2021

(54) SQUALAMINE SOLID FORMS AND METHODS OF MAKING THE SAME

(71) Applicant: Enterin, Inc., Philadelphia, PA (US)

(72) Inventors: Denise Barbut, Philadelphia, PA (US); Michael Zasloff, Philadelphia, PA (US)

(73) Assignee: Enterin, Inc., Philadelphia, PA (US)

( * ) Notice: Subject to any disclaimer, the term of this patent is extended or adjusted under 35 U.S.C. 154(b) by 0 days.

(21) Appl. No.: 16/172,204

(22) Filed: Oct. 26, 2018

(65) Prior Publication Data
US 2019/0127416 A1  May 2, 2019

Related U.S. Application Data

(60) Provisional application No. 62/579,084, filed on Oct. 30, 2017.

(51) Int. Cl.
C07J 41/00  (2006.01)
(52) U.S. Cl.
CPC ....... C07J 41/0005 (2013.01); *C07B 2200/13* (2013.01)
(58) Field of Classification Search
CPC .................. C07J 41/0005; C07B 2200/13
See application file for complete search history.

(56) References Cited

U.S. PATENT DOCUMENTS

| | | | |
|---|---|---|---|
| 3,773,919 | A | 11/1973 | Boswell et al. |
| 4,485,045 | A | 11/1984 | Regen |
| 4,544,545 | A | 10/1985 | Ryan et al. |
| 5,192,756 | A | 3/1993 | Zasloff et al. |
| 8,623,416 | B2 * | 1/2014 | Zasloff ................. A61K 9/0019 424/130.1 |
| 8,729,058 | B2 | 5/2014 | Zasloff |
| 2007/0010504 | A1 | 1/2007 | Chellquist et al. |
| 2011/0123624 | A1 | 5/2011 | Zasloff |
| 2015/0368290 | A1 | 12/2015 | Zasloff et al. |

FOREIGN PATENT DOCUMENTS

| | | |
|---|---|---|
| DE | 3218121 A1 | 11/1983 |
| EP | 102324 | 3/1984 |
| EP | 52322 | 3/1985 |
| EP | 133988 | 3/1985 |
| EP | 142641 | 5/1985 |
| EP | 0 058 481 B1 | 10/1986 |
| EP | 88046 | 12/1987 |
| EP | 143949 | 10/1988 |
| EP | 36676 | 9/1990 |
| WO | WO 98/50347 | 11/1998 |
| WO | WO 98/54366 | 12/1998 |

OTHER PUBLICATIONS

Barbara Rodriguez-Spong et al., General principles of pharmaceutical solid polymorphism: a supramolecular perspective, Advanced Drug Delivery Reviews 56 (2004) 241-274 (Year: 2004).*
Dario Braga et al., Crystal Polymorphism and Multiple Crystal Forms, Struct Bond (2009) 132: 25-50 (Year: 2009).*
Alexander et al., "Membrane surface charge dictates the structure and function of the epithelial na+/h+ exchanger," EMBO J., 30:679-691 (2011).
Bhargava et al., "A phase I and pharmacokinetic study of squalamine, a novel antiangiogenic agent, in patients with advanced cancers," *Clin. Cancer Res.*, 7(12): 3912-9 (2001).
Chen, et al., "Inactivation of HIV-1 Chemokine Co-Receptor CXCR-4 by a Novel Intrakine Strategy," *Nat. Med*, vol. 3, pp. 1110-1116 (1997).
Chitkul, et al., "A new bio-compatible pH cleavable linker for solid-phase synthesis of a squalamine analogue," *Tetrahedron Letters*, vol. 42, pp. 6211-6214 (2001).
Connolly, et al., "Squalamine Lactate for Exudative Age-Related Macular Degeneration," *Ophthalmol. Clin. North Am.*, vol. 19, pp. 381-391 (2006).
Genaidy et al., "Effect of squalamine on iris neovascularization in monkeys." *Retina*, 22(6): 772-8 (2002)[Abstract].
Gonda, Aerosols for Dellvery of Therapeutic and Diagnostic Agents to the Respiratory Tract, Critical Reviews in Therapeutic Drug Carter Systems, vol. 6, No. 4, pp. 273-313 (Jan. 1990).
Gonzalez-Rey et al., "Therapeutic effect of vasoactive intestinal peptide on experimental autoimmune encephalomyelitis: down-regulation of inflammatory and autoimmune responses," *Am. J. Pathol.*, 168(4): 1179-88 (2006).
Gressens et al., "Vasoactive intestinal peptide prevents excitotoxic cell death in the murine developing brain," *J. Clin. Invest.*, 100(2): 390-7 (1997).
Hao et al., "A Phase I and pharmacokinetic study of squalamine, an aminosterol angiogenesis inhibitor," *Clin. Cancer Res.*, 9(7): 2465-71 (2003).
Herbst et al., "A phase I/IIA trial of continuous five-day infusion of squalamine lactate (MSI-1256F) plus carboplatin and paclitaxel in patients with advanced non-small cell lung cancer," *Clin. Cancer Res.*, 9(11): 4108-15 (2003).
Higgins et al., "Regression of Retinopathy by Squalimine in a Mouse Model," *Pediatric Research*, vol. 56, No. 1, pp. 144-149 (2004).
Higgins et al., "Squalamine improves retinal neovascularization," *Invest. Ophthalmol. Vis. Sci.*, 41(6): 1507-12 (2000).
Jones, et al., "Efficient Route to 7 α-(Benzoyloxy)-3-dioxolane Cholestan-24(R)-ol, a Key Intermediate in the Synthesis of Squalamine," *The Journ. of Organic Chemistry*, vol. 63, pp. 3786-3789 (1998).
Li et al., "GLP-1 receptor stimulation preserves primary cortical and dopaminergic neurons in cellular and rodent models of stroke and Parkinsonism," *Proc. Natl. Acad. Sci. USA*, 106(4): 1285-90 (2009).
Langer, et al., "Biocompatibility of polymeric delivery systems for macromolecules," *J. Biomed. Mater Res.*, vol. 15, No. 2, pp. 267-277 (Mar. 1981).
Langer, "New Methods of Drop Delivery," Science, vol. 249, No. 4976, 1527-1533 (Sep. 1990).
Li et al., "Squalamine and cisplatin block angiogenesis and growth of human ovarian cancer cells with or without HER-2 gene overexpression," *Oncogene*, 21(18): 2805-14 (2002).
Moore et al., "Squalamine: an aminosterol antibiotic from the shark," *Proc. Natl. Acad. Sci. USA*, 90(4): 1354-8 (1993).
Perni, et al., "A Natural Product Inhibits the Initiation of a-synuclein aggregation and suppresses its toxicity," *Proc. Natl. Acad. Sci.*, 114(6), E1009-E1017 (Feb. 2017).

(Continued)

*Primary Examiner* — Sarah Pihonak
*Assistant Examiner* — Jason Deck
(74) *Attorney, Agent, or Firm* — Foley & Lardner LLP

(57) ABSTRACT

Provided herein are crystalline solid forms of squalamine phosphate designated as Form 1 and Form 2, compositions containing one or both forms, and methods of their preparation and of their use.

8 Claims, 17 Drawing Sheets

(56) References Cited

OTHER PUBLICATIONS

Raeburn; et al., "Techniques for drug delivery to the airways, and the assessment of lung function in animal models," Journal of Pharmacological and Toxicological Methods, vol. 27, Issue 3, May 1992, pp. 143-159.
Rao et al., "Aminosterols from the dogfish shark Squalus acanthias," *J. Nat. Prod.*, 63(5): 631-5 (2000) [Abstract].
Salmi et al., "New stereoselective titanium reductive amination synthesis of 3-amino and polyaminosterol derivatives possessing antimicrobial activities," *Eur. J. Med. Chem.*, 43(3): 540-7 (2008) [Abstract].
Salmi et al., "Squalamine: an appropriate strategy against the emergence of multidrug resistant gram-negative bacteria?" *PLoS ONE*, 3(7): e2765 (2008).
Schiller, J. H. and G. Bittner, "Potentiation of platinum antitumor effects in human lung tumor xenografts by the angiogenesis inhibitor squalamine: effects on tumor neovascularization," *Clin. Cancer Res.*, 5(12): 4287-94 (1999).
Selinsky et al., "Squalamine is not a proton ionophore," *Biochim. Biophys. Acta.*, 1464(1): 135-41 (2000).
Selinsky et al., "The aminosterol antibiotic squalamine permeabilizes large unilamellar phospholipid vesicles," *Biochim. Biophys. Acta.*, 1370(2): 218-34 (1998).
Sidman, et al., "Controlled release of macromolecules and pharmaceuticals from synthetic polypeptides based on glutamic acid," Biopolymers, vol. 22, pp. 547-556 (1933).
Sills et al., "Squalamine inhibits angiogenesis and solid tumor growth in vivo and perturbs embryonic vasculature," *Cancer Res.*, 58(13): 2784-92 (1998).
Sokoloff et al., "Adjunctive therapy for men with high risk localized and locally advanced prostate cancer: targeting disseminated tumor cells," *J. Urol.*, 172(6 Pt 2): 2539-44 (2004) [Abstract].
Sumioka et al., "TARP phosphorylation regulates synaptic AMPA receptors through lipid bilayers," *Neuron*, 66(5): 755-767 (2009).
Williams et al., "Squalamine treatment of human tumors in nu/nu mice enhances platinum-based chemotherapies," *Clin. Cancer Res.*, 7(3): 724-33 (2001).
Yeung et al., "Membrane phosphatidylserine regulates surface charge and protein localization," *Science*, 319(5860): 210-3 (2008) [Abstract].
Yin et al., "Antiangiogenic treatment delays chondrocyte maturation and bone formation during limb skeletogenesis," *J. Bone Miner. Res.*, 17(1): 56-65 (2002).
Yun et al., Identification of Squalamine in the Plasma Membrane of White Blood Cells in the Sea Lamprey, *Petromyzon marinus*, pp. vol. 48, No. 12, pp. 2579-2586 (2007).
Zasloff et al., "A spermine-coupled cholesterol metabolite from the shark with potent appetite suppressant and antidiabetic properties," *Int. J. Obes. Relat. Metab. Disord.*, 25(5): 689-97 (2001).
Zasloff et al., "Squalamine as a broad-spectrum systemic antiviral agent with therapeutic potential," *Proc. Natl. Acad. Sci. USA*, 108(38): 15978-83 (2011).
Zasloff, M., "Antimicrobial peptides of multicellular organisms," *Nature*, 415(6870): 389-95 (2002) [Abstract].
International Search Report and Written Opinion issued in co-pending International Patent Application No. PCT/US2018/057650, completed Feb. 8, 2019.
International Preliminary Report on Patentability in co-pending International Patent Application No. PCT/US2018/057650, dated May 14, 2020.
Langer, "Controlled release of macromolecules", Chemtech, 1982, pp. 98-105, vol. 12.
Lopez-Berestein, "Treatment of systemic fungal infections with liposomal amphotericin B," *Arch. Intern. Med.*, vol. 149, No. 11, pp. 2533-2536 (1989).

\* cited by examiner

SQUALAMINE SOLID FORMS AND METHODS OF MAKING THE SAME

CROSS-REFERENCE TO RELATED APPLICATION

This application claims priority to U.S. Provisional Application No. 62/579,084, filed on Oct. 30, 2017, the disclosure of which is specifically incorporated by reference in its entirety.

FIELD OF THE DISCLOSURE

The present technology relates generally to solid forms of squalamine phosphate.

BACKGROUND

The discovery of squalamine, a water soluble compound, the structure of which is shown below, was reported by Michael Zasloff in 1993 (U.S. Pat. No. 5,192,756). Squalamine was discovered in various tissues of the dogfish shark (*Squalus acanthias*) in a search for antibacterial agents. The most abundant source of squalamine is in the livers of *Squalus acanthias*, though it is found in other sources, such as lampreys (Yun et al., "Identification of Squalamine in the Plasma Membrane of White Blood Cells in the Sea Lamprey," *J. Lipid Res.*, 48(12): 2579-2586 (2007)).

states known to be associated with pathological neovascularization, such as cancer (Sills et al., "Squalamine inhibits angiogenesis and solid tumor growth in vivo and perturbs embryonic vasculature," *Cancer Res.*, 58(13): 2784-92 (1998); Schiller, J. H. and G. Bittner, "Potentiation of platinum antitumor effects in human lung tumor xenografts by the angiogenesis inhibitor squalamine: effects on tumor neovascularization," *Clin. Cancer Res.*, 5(12): 4287-94 (1999); Bhargava et al., "A phase I and pharmacokinetic study of squalamine, a novel antiangiogenic agent, in patients with advanced cancers," *Clin. Cancer Res.*, 7:3912-9 (2001); Williams et al., "Squalamine treatment of human tumors in nu/nu mice enhances platinum-based chemotherapies," *Clin. Cancer Res.*, 7(3): 724-33 (2001); Hao et al., "A Phase I and pharmacokinetic study of squalamine, an aminosterol angiogenesis inhibitor," *Clin. Cancer Res.*, 9(7): 2465-71 (2003); Herbst et al., "A Phase PITA Trial of Continuous Five-Day Infusion of Squalamine Lactate (MSI-1256F) Plus Carboplatin and Paclitaxel in Patients with Advanced Non-Small Cell Lung Cancer 1," *Clinical Cancer Research*, 9:4108-4115 (2003); Sokoloff et al., "Adjunctive therapy for men with high risk localized and locally advanced prostate cancer: targeting disseminated tumor cells," *J. Urol.*, 172(6 Pt 2): 2539-44 (2004)), and vascular disorders of the eye, including macular degeneration (US 2007/10504A1), retinopathy of prematurity (Higgins et al., "Squalamine improves retinal neovascularization," *Invest. Ophthalmol. Vis. Sci.*, 41(6): 1507-12 (2000); Higgins et al.,

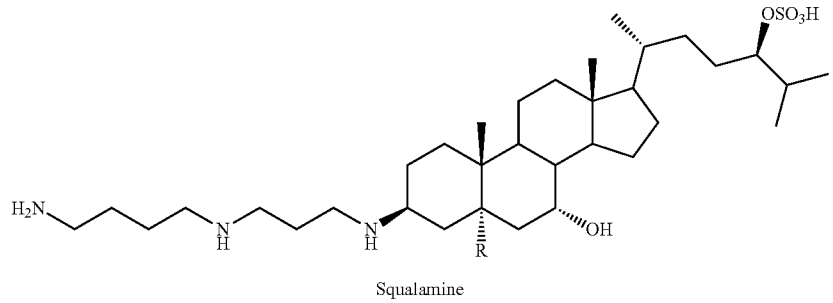

Squalamine

Chemically, squalamine presented a structure never before seen in nature, that being a bile acid coupled to a polyamine (spermidine); i.e., a steroid chemically linked to a polyamine. The chemical structure of squalamine, also known as 3 beta-N-1-(N-[3-(4-aminobutyl)]-1,3-diaminopropane)-7 alpha,24 zeta-dihydroxy-5 alpha-cholestane 24-sulfate, has been determined by fast atom bombardment mass spectroscopy and NMR. Squalamine is a cationic steroid characterized by a condensation of an anionic bile salt intermediate with spermidine.

Numerous studies later demonstrated that squalamine exhibits potent antibacterial activity in vitro (Salmi et al., "Squalamine: an appropriate strategy against the emergence of multidrug resistant gram-negative bacteria?" *PLoS ONE*, 3(7): e2765 (2008)). Subsequently, squalamine was discovered to exhibit antiangiogenic activity in vitro and upon administration to animals (Sills et al., "Squalamine inhibits angiogenesis and solid tumor growth in vivo and perturbs embryonic vasculature," *Cancer Res.*, 58(13): 2784-92 (1998); Yin et al., "Antiangiogenic treatment delays chondrocyte maturation and bone formation during limb skeletogenesis," *J. Bone Miner. Res.*, 17(1): 56-65 (2002)). As a consequence, squalamine has been evaluated in disease "Regression of retinopathy by squalamine in a mouse model," *Pediatr. Res.*, 56(1): 144-9 (2004); US2007/10504A1), corneal neovascularization (Genaidy et al., "Effect of squalamine on iris neovascularization in monkeys." Retina, 22(6): 772-8 (2002)) and diabetic retinopathy (US 2007/10504A1).

The utility of squalamine as an anti-infective has been demonstrated in vitro against bacteria and fungi (Moore et al., "Squalamine: an aminosterol antibiotic from the shark," *Proc. Natl. Acad. Sci. USA*, 90(4): 1354-8 (1993); Rao et al., "Aminosterols from the dogfish shark *Squalus acanthias*," *J. Nat. Prod.*, 63(5): 631-5 (2000); Salmi et al., "Squalamine: an appropriate strategy against the emergence of multidrug resistant gram-negative bacteria?" *PLoS ONE*, 3(7): e2765 (2008)). Squalamine is a cationic amphipathic substance exhibiting an affinity for membranes composed of anionic phospholipids (Selinsky et al., "The aminosterol antibiotic squalamine permeabilizes large unilamellar phospholipid vesicles," *Biochim. Biophys. Acta.*, 1370(2): 218-34 (1998); Selinsky et al., "Squalamine is not a proton ionophore," *Biochim. Biophys. Acta.*, 1464(1): 135-41 (2000)). Like other such agents, including magainin and other cationic antimicrobial peptides, squalamine is believed to exert antimicrobial action by interacting electrostatically with the membranes of target microorganisms, which generally display anionic phospholipids on the membrane surface exposed to the environment, subsequently disturbing their functional integrity, and causing death of the targeted microbe (Sills et al., "Squalamine inhibits angiogenesis and solid tumor growth in vivo and perturbs embryonic vasculature," *Cancer Res.*, 58(13): 2784-92 (1998); Zasloff, M., "Antimicrobial peptides of multicellular organisms," *Nature*, 415(6870): 389-95 (2002); Salmi et al., "Squalamine: an appropriate strategy against the emergence of multidrug resistant gram-negative bacteria?" *PLoS ONE*, 3(7): e2765 (2008)).

Recent studies have highlighted the efficacy of systemically administered squalamine to prevent or treat viral infections in animals (Zasloff et al., "Squalamine as a broad-spectrum systemic antiviral agent with therapeutic potential," *Proc. Natl. Acad. Sci. USA*, 108(38): 15978-83 (2011); U.S. Pat. No. 8,729,058).

The mechanism of action. It has been reported that squalamine exerts its effects at the cellular level by displacing proteins bound electrostatically to negatively charged membranes, causing pleiotropic changes in the functional state of the cell (Alexander et al., "Membrane surface charge dictates the structure and function of the epithelial na+/h+ exchanger," *EMBO J.*, 30:679-691.(2011); Yeung et al., "Membrane phosphatidylserine regulates surface charge and protein localization," *Science*, 319(5860): 210-3 (2008); Sumioka et al., "TARP phosphorylation regulates synaptic AMPA receptors through lipid bilayers," *Neuron*, 66(5): 755-67 (2009); Zasloff et al., "Squalamine as a broad-spectrum systemic antiviral agent with therapeutic potential," *Proc. Natl. Acad. Sci. USA*, 108(38): 15978-83 (2011)).

Prior clinical studies in humans have focused on the anti-angiogenic properties of squalamine. Squalamine in its intravenous form, squalamine lactate, is in the process of being tested as a treatment for fibrodysplasia ossificans progressiva, a rare disease where connective tissue will ossify when damaged. Genesis, A., "Squalamine trial for the treatment of fibrodysplasia ossificans progressiva initiated", *Angiogenesis Weekly*, 8:45 (2002). Squalamine is also undergoing trials for treatment of non-small cell lung cancer (stage PITA) as well as general phase I pharmacokinetic studies. Herbst et al., "A Phase PITA Trial of Continuous Five-Day Infusion of Squalamine Lactate (MSI-1256F) Plus Carboplatin and Paclitaxel in Patients with Advanced Non-Small Cell Lung Cancer 1," *Clinical Cancer Research*, 9:4108-4115 (2003); Hao et al., "A Phase I and Pharmacokinetic Study of Squalamine, an Aminosterol Angiogenesis Inhibitor", *Clin Cancer Res.*, 9(7): 2465-2471 (2003). In 2005, the Food and Drug Administration granted squalamine Fast Track status for approval for treatment of age-related macular degeneration. CATE: California Assistive Technology Exchange," California Assistive Technology Exchange, http://cate.ca.gov/index.cfm?a=Resources&p=News&article=176, Retrieved 2009-03-31. In 2011, Ohr Pharmaceuticals initiated clinical trials to evaluate squalamine lactate, administered as an eye drop, for the treatment of wet macular degeneration, based on their assessment that sufficiently high concentrations of squalamine can access the retina, when the substance is placed onto the corneal surface. These studies are ongoing. Genaera Corporation discontinued trials for the use of squalamine in treating cancer in 2007. "PROSTATE CANCER; Genaera Discontinues LOMUCIN in Cystic Fibrosis and Squalamine in Prostate Cancer Studies," *Drug Week, pp.* 251. 2007-07-20; "Reports describe the most recent news from Genaera Corporation," *Biotech Business Week*, pp. 1540 (2007-09-17).

Squalamine is also marketed under the brand name Squalamax™ as a dietary supplement, though it has not been approved as a drug in this form and thus cannot make therapeutic claims. Squalamax™ is an unfractionated extract of shark liver, containing innumerable uncharacterized substances in addition to squalamine, and squalamine is present in Squalamax™ at less than 0.01% of the total weight of the extract. "Cyber Warning Letter", Center for Drug Evaluation and Research (2002-05-06), www.fda.gov/CDER/warn/cyber/2002/CFSANnuGen.htm; Retrieved 2009-03-31. Moreover, the dietary supplement form of squalamine is not pharmaceutical grade squalamine, as pharmaceutical grade squalamine requires significantly greater manufacturing efforts.

By 2006, over 300 patients had received squalamine in doses ranging from 6-700 mg/m$^2$/day by iv administration, in three Phase I and nine Phase II studies. Hao et al., "A Phase I and pharmacokinetic study of squalamine, an aminosterol angiogenesis inhibitor," *Clin. Cancer Res.*, 9:2465-71 (2003); Herbst et al., "A phase PITA trial of continuous five-day infusion of squalamine lactate (MSI-1256F) plus carboplatin and paclitaxel in patients with advanced non-small cell lung cancer," *Clin. Cancer Res.*, 9:4108-15 (2003); Bhargava et al., "A phase I and pharmacokinetic study of squalamine, a novel antiangiogenic agent, in patients with advanced cancers," *Clin. Cancer Res.*, 7:3912-9 (2001); and Connolly et al., "Squalamine lactate for exudative age-related macular degeneration," *Ophthalmol. Clin. North Am.*, 19:381-91 (2006). The studies showed that the compound exhibited an acceptable safety profile and evidence of efficacy in these early trials. In 2006 development of squalamine was halted for economic/strategic reasons by Genaera. In 2011 Ohr Pharmaceuticals initiated studies of the compound administered as an eye drop for the treatment of retinal eye disease, but all studies of this compound against cancer have remained in a dormant stage since.

In 2017 Enterin, Inc. initiated a Phase 2a clinical trial evaluating orally administered squalamine phosphate tablets for the treatment of constipation associated with Parkinson's disease. The science behind this trial is based on the discovery that squalamine can displace alpha-synuclein, the protein involved in the pathophysiology of Parkinson's disease, from membranes both in vitro and in vivo via the electrostatic displacement mechanism described above (Perni M, Galvagnion C, Maltsev A, Meisl G, Müller M B, Challa P K, Kirkegaard J B, Flagmeier P, Cohen S I, Cascella R, Chen S W, Limboker R, Sormanni P, Heller G T, Aprile F A, Cremades N, Cecchi C, Chiti F, Nollen E A, Knowles T P, Vendruscolo M, Bax A, Zasloff M, Dobson C M. A natural product inhibits the initiation of α-synuclein aggregation and suppresses its toxicity. Proc Natl Acad Sci USA. 2017 Feb. 7; 114(6):E1009-E1017).

Given the potential clinical significance of squalamine, there is a need in the art for new forms of the drug. The present invention satisfies this need.

SUMMARY

In one aspect, provided herein is an isolated solid form of squalamine phosphate designated as Form 1. In some embodiments, the solid form has an X-ray powder diffraction pattern comprising peaks, in terms of 2-theta, at about 15.7° and about 23.7°. In some embodiments, the solid form has an X-ray powder diffraction pattern comprising peaks, in terms of 2-theta, at about 11.7°, about 15.7°, about 19.7°, and about 23.7°. In some embodiments, the solid form has an X-ray powder diffraction pattern substantially as shown in FIG. 8. In some embodiments, the solid form has a differential scanning calorimetry (DSC) thermogram comprising an endothermic peak at about 96.6° C. In some embodiments, the solid form has a differential scanning calorimetry (DSC) thermogram substantially as shown in FIG. 9. In some embodiments, the solid form has a thermogravimetric analysis (TGA) substantially as shown in FIG. 10. In some embodiments, the solid form is substantially purified. In some embodiments, the solid form has a water content of less than about 8%. In some embodiments, the solid form has a water content of about 6-8%.

In another aspect, provided herein is a solid form of squalamine phosphate having an X-ray powder diffraction pattern comprising peaks, in terms of 2-theta, at about 15.7° and at about 23.7°. In some embodiments, the solid form has an X-ray powder diffraction pattern comprising peaks, in terms of 2-theta, at about 11.7°, about 15.7°, about 19.7°, and about 23.7°. In some embodiments, the solid form has an X-ray powder diffraction pattern substantially as shown in FIG. 8. In some embodiments, the solid form has a differential scanning calorimetry (DSC) thermogram comprising an endothermic peak at about 96.6° C. In some embodiments, the solid form has a differential scanning calorimetry (DSC) thermogram substantially as shown in FIG. 9. In some embodiments, the solid form has a thermogravimetric analysis (TGA) substantially as shown in FIG. 10. In some embodiments, the solid form is substantially purified. In some embodiments, the solid form has a water content of less than about 8%. In some embodiments, the solid form has a water content of about 6-8%.

In another aspect, provided herein is a crystalline squalamine phosphate, characterized by an X-ray powder diffraction pattern comprising the following peaks: about 15.7° 2-theta and about 23.7° 2-theta, as determined on a diffractometer using Cu-Kα radiation at a wavelength of 1.5406 Å.

In another aspect, provided herein is an isolated squalamine phosphate solid form designated as Form 2. In some embodiments, the solid form has an X-ray powder diffraction pattern comprising a peak, in terms of 2-theta, at about 15.2° and at about 22.9°. In some embodiments, the solid form has an X-ray powder diffraction pattern comprising a peak, in terms of 2-theta, at about 11.4°, at about 15.2° and at about 22.9°. In some embodiments, the solid form has an X-ray powder diffraction pattern substantially as shown in FIG. 15. In some embodiments, the solid form has a differential scanning calorimetry (DSC) thermogram comprising an endothermic peak at about 90.9° C. In some embodiments, the solid form has a differential scanning calorimetry (DSC) thermogram substantially as shown in FIG. 16. In some embodiments, the solid form has a thermogravimetric analysis (TGA) substantially as shown in FIG. 17. In some embodiments, the solid form is substantially purified. In some embodiments, the solid form has a water content of about 9-12%. In some embodiments, the solid form has a water content of more than about 9%.

In another aspect, provided herein is a solid form of squalamine phosphate having an X-ray powder diffraction pattern comprising a peak, in terms of 2-theta, at about 15.2° and at about 22.9°. In some embodiments, the solid form has an X-ray powder diffraction pattern substantially as shown in FIG. 15. In some embodiments, the solid form has a differential scanning calorimetry (DSC) thermogram comprising an endothermic peak at about 90.9° C. In some embodiments, the solid form has a differential scanning calorimetry (DSC) thermogram substantially as shown in FIG. 16. In some embodiments, the solid form has a thermogravimetric analysis (TGA) substantially as shown in FIG. 17. In some embodiments, the solid form is substantially purified. In some embodiments, the solid form has a water content of about 9-12%. In some embodiments, the solid form has a water content of more than about 9%.

In another aspect, provided herein is a crystalline squalamine phosphate, characterized by an X-ray powder diffraction pattern comprising the following peaks: at about 11.4° 2-theta, at about 15.2° 2-theta and at about 22.9° 2-theta, as determined on a diffractometer using Cu-Kα radiation at a wavelength of 1.5406 Å.

In another aspect, provided herein are pharmaceutical composition comprising the squalamine phosphate solid form of Form 1 or Form 2, and a pharmaceutically acceptable carrier.

In another aspect, provided herein are pharmaceutical compositions comprising squalamine phosphate, wherein the squalamine phosphate in the composition comprises the squalamine phosphate solid form of Form 1 or Form 2 in an amount of at least about 90% by weight.

In another aspect, provided herein are pharmaceutical compositions consisting essentially of the squalamine phosphate solid form of Form 1 or Form 2.

In another aspect, provided herein are pharmaceutical composition comprising the squalamine phosphate solid form of Form 1, the squalamine phosphate solid form of Form 2, and a pharmaceutically acceptable carrier.

In another aspect, provided herein are pharmaceutical compositions comprising squalamine phosphate, wherein the squalamine phosphate in the composition comprises the squalamine phosphate solid form of Form 1 and the squalamine phosphate solid form of Form 2 in a total amount of at least about 90% by weight.

In another aspect, provided herein are pharmaceutical compositions consisting essentially of the squalamine phosphate solid form of Form 1 and the squalamine phosphate solid form of Form 2.

In another aspect, provided herein are methods for treating a subject in need having a condition susceptible to treatment with an aminosterol, comprising administering to the subject a therapeutically effective amount of the squalamine phosphate solid form of Form 1 and/or Form 2, or a pharmaceutical composition comprising the squalamine phosphate solid form of Form 1 and/or Form 2. In some embodiments, provided herein are methods for treating a subject in need having a condition susceptible to treatment with an aminosterol, comprising administering to the subject a therapeutically effective amount of a composition comprising or consisting essentially of a squalamine phosphate solid form of Form 1 and/or Form 2, and one or more pharmaceutically acceptable carriers and/or excipients.

In some embodiments, the subject in need has a condition selected from the group consisting of viral infections, antimicrobial infections, Gram-negative and Gram-positive bacterial infections, Mycobacteria infections, fungal infections, protozoan infections, disease states known to be associated with pathological neovascularization, such as cancer, vascular disorders of the eye, including macular degeneration, such as age-related macular degeneration, retinopathy of prematurity, corneal neovascularization, diabetic retinopathy, weight loss or weight management, dose-dependent weight loss; diseases, including viral infections, where sodium-hydrogen exchanger ("NHE-3") plays a critical role, treatment of fibrodysplasia ossificans progressiva, disorders of neovascularization, and sleep disorders. In some embodiments, the viral infection is caused by a virus selected from the group consisting of Yellow Fever, Cytomegalovirus, Eastern Equine Encephalitis virus, Hepatitis B virus, Hepatitis Delta virus, Dengue virus, and Human Immunodeficiency virus. In some embodiments, the condition to be treated is a viral infection caused by a virus selected from the group consisting of "African Swine Fever Viruses," Arbovirus, Adenoviridae, Arenaviridae, Arterivirus, Astroviridae, Baculoviridae, Bimaviridae, Birnaviridae, Bunyaviridae, Caliciviridae, Caulimoviridae, Circoviridae, Coronaviridae, Cystoviridae, Dengue, EBV, HIV, Deltaviridae, Filviridae, Filoviridae, Flaviviridae, Hepadnaviridae (Hepatitis), Herpesviridae (such as, Cytomegalovirus, Herpes Simplex, Herpes Zoster), Iridoviridae, Mononegavirus (e.g., Paramyxoviridae, Morbillivirus, Rhabdoviridae), Myoviridae, Orthomyxoviridae (e.g., Influenza A, Influenza B, and parainfluenza), Papiloma virus, Papovaviridae, Paramyxoviridae, Prions, Parvoviridae, Phycodnaviridae, Picomaviridae (e.g., Rhinovirus, Poliovirus), Poxviridae (such as Smallpox or Vaccinia), Potyviridae, Reoviridae (e.g., Rotavirus), Retroviridae (HTLV-I, HTLV-II, Lentivirus), Rhabdoviridae, Tectiviridae, Togaviridae (e.g., Rubivirus), herpes, pox, papilloma, corona, influenza, hepatitis, sendai, sindbis, vaccinia viruses, west nile, hanta, viruses which cause the common cold, and any combination thereof. In some embodiments, the condition to be treated is selected from the group consisting of AIDS, viral meningitis, Dengue, EBV, hepatitis, a chronic disease suspected to be of viral origin, multiple sclerosis, Type I diabetes, Type II diabetes, atherosclerosis, cardiomyopathies, Kawaski disease, aplastic anemia, and any combination thereof. In some embodiments, the condition to be treated is a neurological disorder selected from the group consisting of Parkinson's disease, autism, multiple system atrophy, depression, Alzheimer's disease, Huntington's Disease, schizophrenia, multiple sclerosis, and degenerative processes associated with aging, autonomic system instability, circadian rhythm disruption, delays in sleep onset, fragmentation of sleep, reduced REM sleep, reduced total sleep time, REM-behavior disorder, sleep breathing disorder including snoring and sleep apnea, hallucinations, narcolepsy, and day-time sleepiness. In some embodiments, the condition to be treated is a gastrointestinal disorder selected from the group consisting of constipation, inflammatory bowel disease, and irritable bowel syndrome. In some embodiments, the method further comprises administering an additional active agent, wherein the additional active agent is administered via a method selected from the group consisting of (a) concomitantly; (b) as an admixture; (c) separately and simultaneously or concurrently; and (d) separately and sequentially. In some embodiments, the subject is human.

In another aspect, the subject in need has a condition selected from the group consisting of disorders of gastrointestinal motility, such as chronic idiopathic constipation, opioid induced constipation, irritable bowel syndrome, and inflammatory bowel disease; diabetes mellitus and diabetic neuropathy; disorders of the nervous system that could benefit from neuro-protection, such as Parkinson's Disease, Alzheimer's disease, Huntington's Disease, acute traumatic injury to the central nervous system, including the spinal cord, stroke, acute head and/or spine injury, degenerative processes associated with aging, including memory loss ("dementia of aging"), cerebral palsy, epilepsy, peripheral sensory neuropathy, and multiple sclerosis; autism; sleep disorders; schizophrenia; depression; and autonomic system lability.

In another aspect, provided herein are processes for preparing the squalamine phosphate solid form of Form 1, the process comprising: (a) combining a solution of squalamine lactate with an aqueous solution of sodium phosphate dibasic and sodium phosphate monobasic to form a combined mixture; (b) heating the combined mixture before allowing the combined mixture to cool; and (c) isolating the combined mixture to isolate the squalamine phosphate solid form. In some embodiments, the combining step is performed at a temperature of about 55° C. to about 70° C. In some embodiments, the combining step is performed at 60±5° C. In some embodiments, the solution of squalamine lactate is a methanol solution of squalamine lactate. In some embodiments, the heating step is performed at 70±5° C. In some embodiments, the process further comprises stirring the combined mixture after cooling but before the isolating step. In some embodiments, the isolating step comprises filtering the combined mixture and washing filtered solids with acetone.

In another aspect, provided herein are processes for preparing the squalamine phosphate solid form of Form 2, the process comprising: (a) dissolving squalamine lactate in base, water, and alcohol to form a first solution; (b) heating the first solution to a first elevated temperature, wherein the first elevated temperature is greater than 25° C.; (c) adding a first amount of phosphoric acid ($H_3PO_4$) to the first solution to form a second solution; (d) heating the second solution to a second elevated temperature higher than the first elevated temperature; (e) adding a second amount of $H_3PO_4$ to the second solution; (f) obtaining a slurry; and (h) isolating the squalamine phosphate solid form. In some embodiments, the base is sodium hydroxide. In some embodiments, the alcohol is ethanol. In some embodiments, the first elevated temperature is at least about 35° C. In some embodiments, the second elevated temperature is at least about 45° C. In some embodiments, the step of obtaining the slurry comprises seeding the mixture. In some embodiments, the step of obtaining the slurry comprises adding a third amount of $H_3PO_4$ to the second solution. In some embodiments, the step of obtaining the slurry comprises cooling the second solution. In some embodiments, the process further comprises aging the slurry prior to the isolating step. In some embodiments, the isolating step comprises filtering the slurry and washing filtered solids with acetone.

The inventions described and claimed herein have many attributes and embodiments including, but not limited to, those set forth or described or referenced in this Brief Summary and the following Brief Description of the Drawings and Detailed Description. It is not intended to be all-inclusive and the inventions described and claimed herein are not limited to or by the features or embodiments identified in this Brief Summary, which is included for purposes of illustration only and not restriction. Additional embodiments may be disclosed in the Detailed Description below.

DETAILED DESCRIPTION

The present technology relates to solid forms of squalamine phosphate, methods of preparing the solid forms, compositions comprising one or more of the solid forms of squalamine phosphate, and methods of use thereof. The solid forms include crystalline solid forms.

Various embodiments are described herein. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As described herein, squalamine has been explored as a pharmaceutical agent useful in treating a wide variety of conditions. However, one of the challenges with methods of treatment using squalamine is identifying a repeatable source for squalamine. Isolation of the compound from its naturally occurring source, e.g., the dogfish shark, is not feasible for large scale use of squalamine. Moreover, synthetic methods of making squalamine have to date been complex, and therefore expensive, due to the structural complexity of the compound. Described herein are methods of making novel crystalline forms of squalamine that can be easily isolated and are suitable for oral and topical formulation. These new methods of chemical synthesis and isolation result in effective and novel forms of squalamine.

One of the challenges of administering squalamine orally or by nasal or pulmonary routes is its extremely bitter taste, making oral and inhalation dosing approaches unacceptable to the patient. Squalamine phosphate, which has limited solubility at neutral pH, has reduced bitterness compared with an equivalent concentration of the fully soluble salt. By virtue of the strong interaction between phosphate ions and squalamine, the free concentration of the squalamine ion (the molecule recognized by the taste receptors) in the presence of phosphate is many orders of magnitude lower than it would be in the absence of phosphate, thereby reducing the effective concentration bathing the taste receptors on the tongue.

I. Solid Forms

A. Form 1

Figure 8:
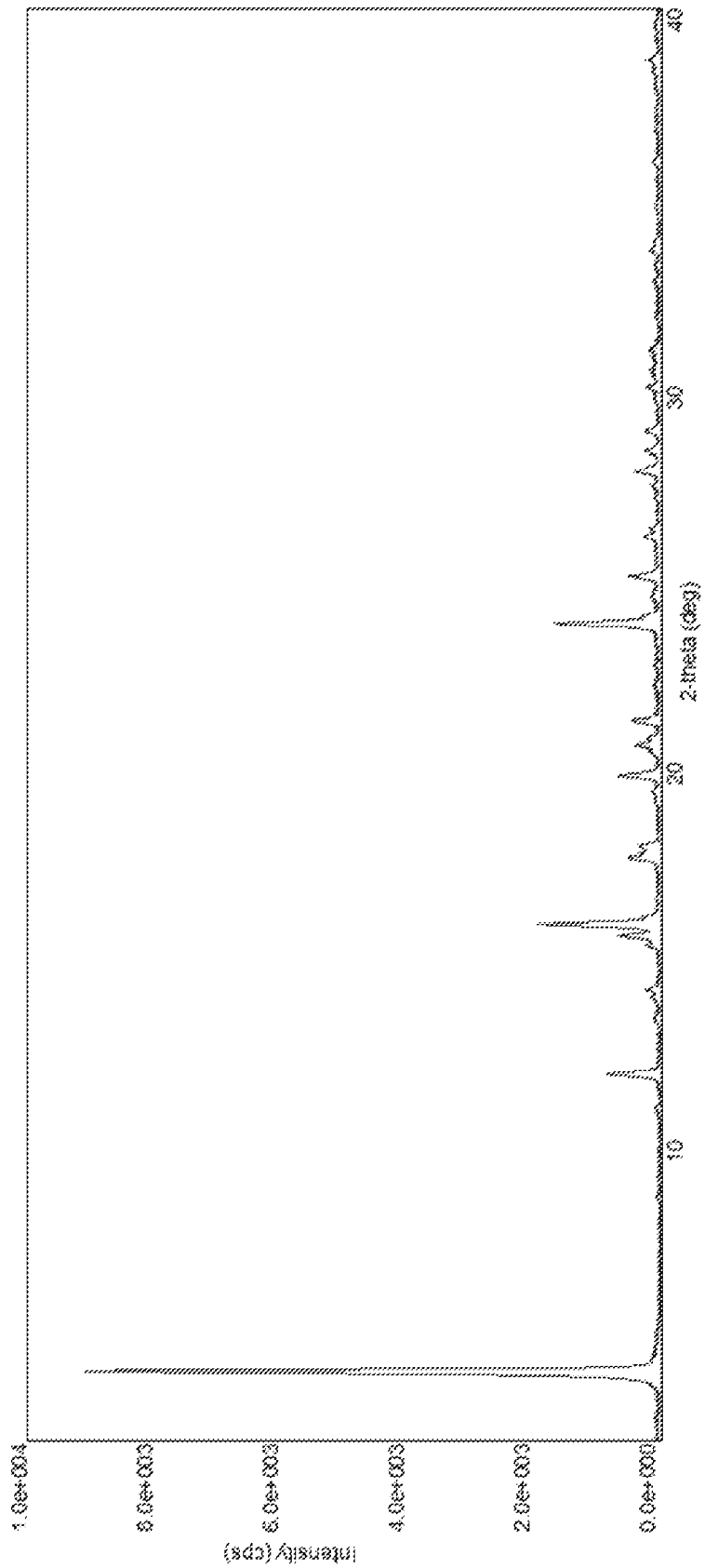
FIG. 8 shows an XRPD pattern of squalamine phosphate, Form 1.
Figure 9:
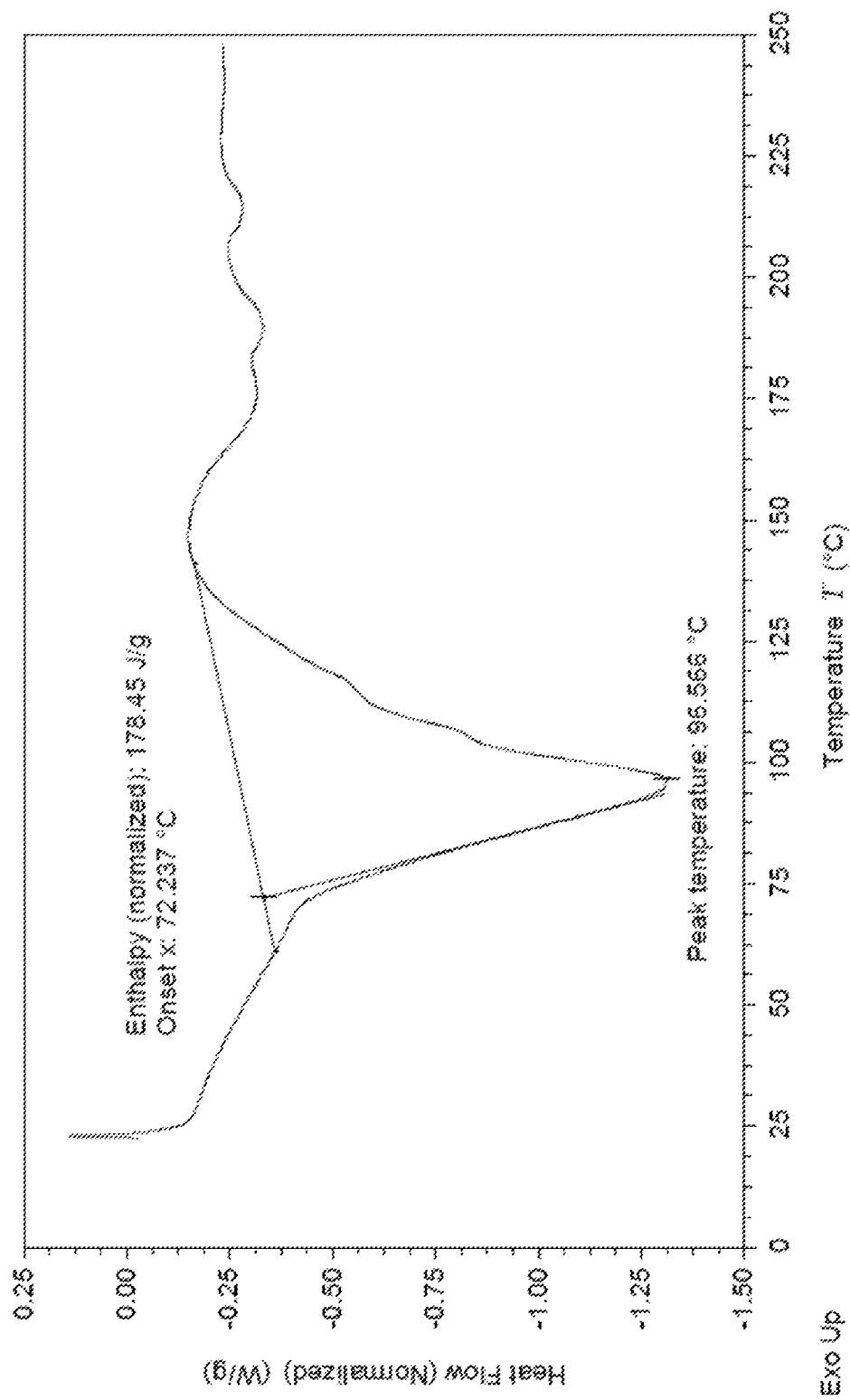
FIG. 9 shows results from DSC of squalamine phosphate, Form 1.
Figure 10:
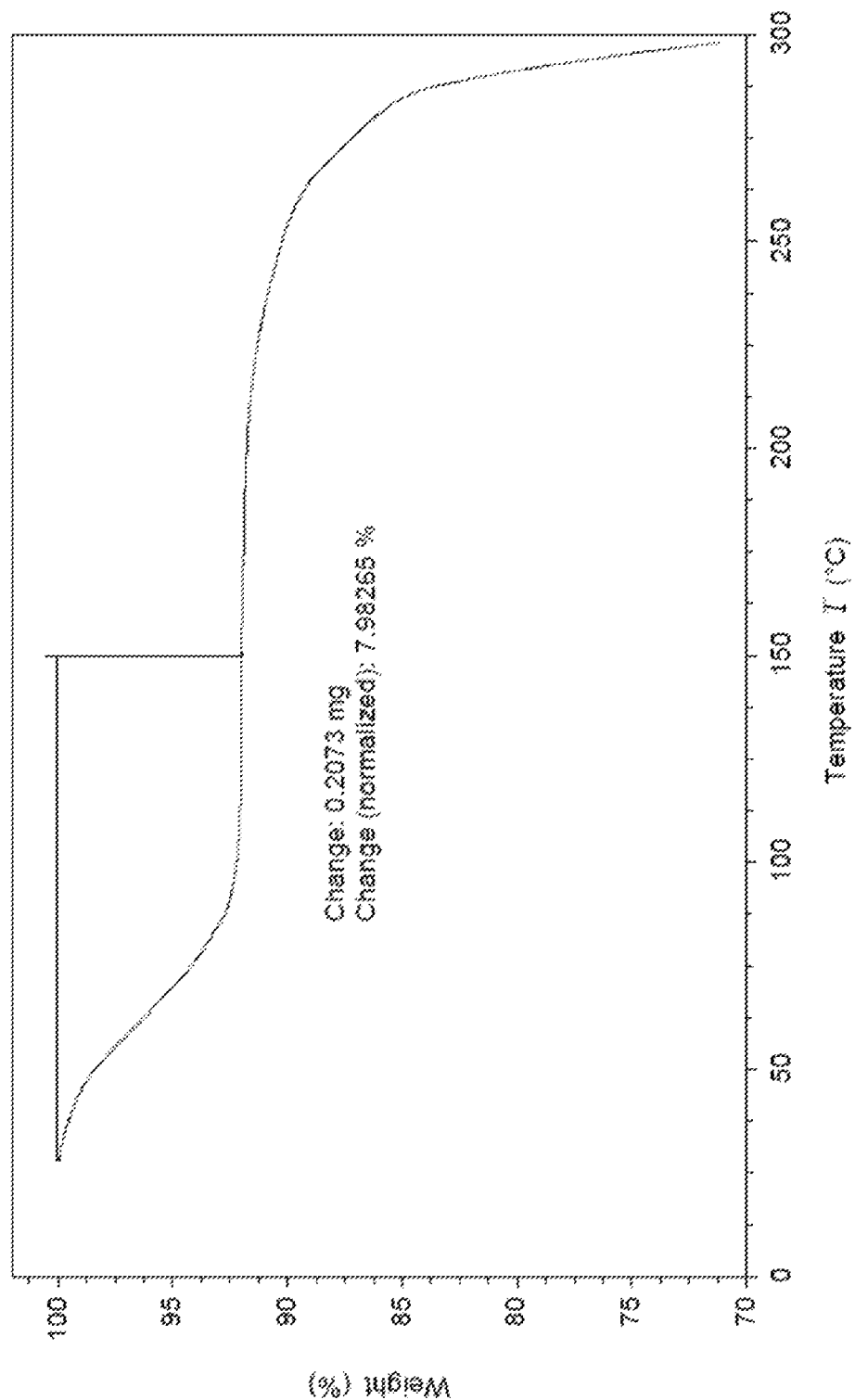
FIG. 10 shows results from TGA of squalamine phosphate, Form 1.

In one aspect, provided herein is an isolated solid form of squalamine phosphate designated as Form 1. In some embodiments, the solid form has an X-ray powder diffraction pattern comprising peaks, in terms of 2-theta, at about 15.7° and at about 23.7°. In some embodiments, the solid form has an X-ray powder diffraction pattern comprising peaks, in terms of 2-theta, at about 11.7°, about 15.7°, about 19.7°, and about 23.7°. In some embodiments, the solid form has an X-ray powder diffraction pattern substantially as shown in FIG. 8. In some embodiments, the solid form has a differential scanning calorimetry (DSC) thermogram comprising an endothermic peak at about 96.6° C. In some embodiments, the solid form has a differential scanning calorimetry (DSC) thermogram substantially as shown in FIG. 9. In some embodiments, the solid form has a thermogravimetric analysis (TGA) substantially as shown in FIG. 10.

In another aspect, provided herein is a solid form having an X-ray powder diffraction pattern comprising peaks, in terms of 2-theta, at about 15.7° and at about 23.7°. In some embodiments, the solid form has an X-ray powder diffraction pattern comprising peaks, in terms of 2-theta, at about 11.7°, about 15.7°, about 19.7°, and about 23.7°. In some embodiments, the solid form has an X-ray powder diffraction pattern substantially as shown in FIG. 8. In some embodiments, the solid form has a differential scanning calorimetry (DSC) thermogram comprising an endothermic peak at about 96.6° C. In some embodiments, the solid form has a differential scanning calorimetry (DSC) thermogram substantially as shown in FIG. 9. In some embodiments, the solid form has a thermogravimetric analysis (TGA) substantially as shown in FIG. 10.

In another aspect, provided herein is a crystalline squalamine phosphate, characterized by an X-ray powder diffraction pattern comprising the following peaks: about 15.7° 2-theta and about 23.7° 2-theta, as determined on a diffractometer using Cu-Kα radiation at a wavelength of 1.5406 Å. In some embodiments, the crystalline squalamine phosphate has an X-ray powder diffraction pattern comprising peaks, in terms of 2-theta, at about 11.7°, about 15.7°, about 19.7°, and about 23.7°. In some embodiments, the crystalline squalamine phosphate has an X-ray powder diffraction pattern substantially as shown in FIG. 8. In some embodiments, the crystalline squalamine phosphate has a differential scanning calorimetry (DSC) thermogram comprising an endothermic peak at about 96.6° C. In some embodiments, the crystalline squalamine phosphate has a differential scanning calorimetry (DSC) thermogram substantially as shown in FIG. 9. In some embodiments, the crystalline squalamine phosphate has a thermogravimetric analysis (TGA) substantially as shown in FIG. 10. In some embodiments, the X-ray powder diffraction comprises a peak, in terms of 2-theta, at about 11.7°, about 15.7°, about 19.7°, and about 23.7°, as determined on a diffractometer using Cu-Kα radiation at a wavelength of 1.5406 Å.

In another aspect, provided herein is a crystalline squalamine phosphate, characterized by (i) an X-ray powder diffraction pattern comprising the following peaks: about 15.7° 2-theta and about 23.7° 2-theta, as determined on a diffractometer using Cu-Kα radiation at a wavelength of 1.5406 Å; and (ii) a differential scanning calorimetry (DSC) thermogram comprising an endothermic peak at about 96.6° C. In some embodiments, the X-ray powder diffraction comprises a peak, in terms of 2-theta, at about 11.7°, about 15.7°, about 19.7°, and about 23.7°, as determined on a diffractometer using Cu-Kα radiation at a wavelength of 1.5406 Å.

In another aspect, provided herein is a crystalline squalamine phosphate, characterized by (i) an X-ray powder diffraction pattern comprising the following peaks: about 15.7° 2-theta and about 23.7° 2-theta, as determined on a diffractometer using Cu-Kα radiation at a wavelength of 1.5406 Å; (ii) a differential scanning calorimetry (DSC) thermogram comprising an endothermic peak at about 96.6° C.; and (iii) has a thermogravimetric analysis (TGA) substantially as shown in FIG. 10. In some embodiments, the X-ray powder diffraction comprises a peak, in terms of 2-theta, at about 11.7°, about 15.7°, about 19.7°, and about 23.7°, as determined on a diffractometer using Cu-Kα radiation at a wavelength of 1.5406 Å.

In another aspect, provided herein is a crystalline squalamine phosphate, characterized by (i) an X-ray powder diffraction pattern comprising the following peaks: about 15.7° 2-theta and about 23.7° 2-theta, as determined on a diffractometer using Cu-Kα radiation at a wavelength of 1.5406 Å; (ii) a differential scanning calorimetry (DSC) thermogram substantially as shown in FIG. 9; and (iii) has a thermogravimetric analysis (TGA) substantially as shown in FIG. 10. In some embodiments, the X-ray powder diffraction comprises a peak, in terms of 2-theta, at about 11.7°, about 15.7°, about 19.7°, and about 23.7°, as determined on a diffractometer using Cu-Kα radiation at a wavelength of 1.5406 Å.

The squalamine phosphate solid form of Form 1 may have a water content of less than or equal to about 8%. In some embodiments, the squalamine phosphate solid form of Form 1 has a water content of less than or equal to about 7%. Thus, in other embodiments of the invention, the squalamine phosphate solid form of Form 1 has a water content of less than or equal to about 7.5%, less than or equal to about 7%, less than or equal to about 6.5%, less than or equal to about 6%, less than or equal to about 5.5%, less than or equal to about 5%, less than or equal to about 4.5%, less than or equal to about 4%, less than or equal to about 3.5%, less than or equal to about 3%, less than or equal to about 2.5%, less than or equal to about 2%, less than or equal to about 1.5%, or less than or equal to about 1.5%, including increments between any of these values. In an exemplary embodiment, the squalamine phosphate solid form of Form 1 may have a water content of about 6% to about 8%, or about 6% to about 7%, or about 7% to about 8%.

B. Form 2

Figure 15:
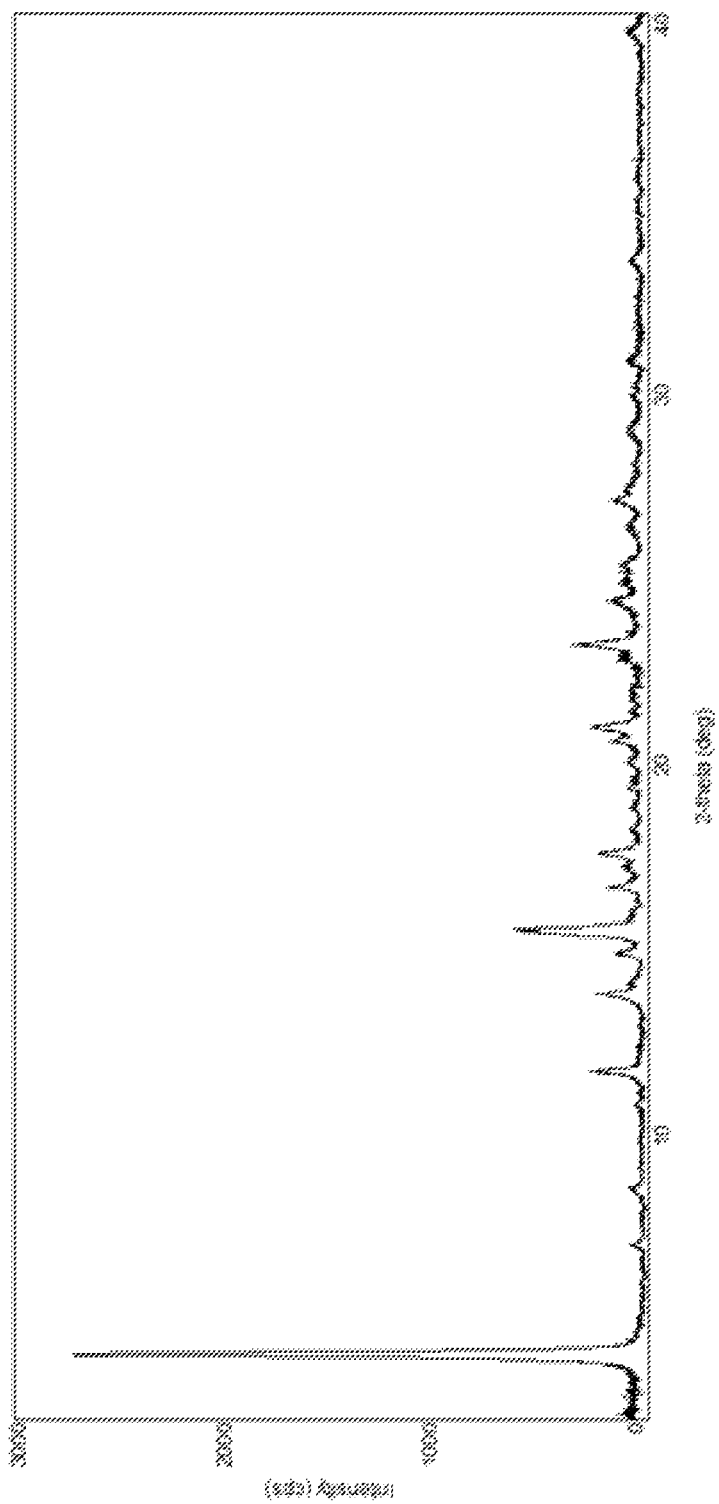
FIG. 15 shows an XRPD pattern of squalamine phosphate, Form 2.
Figure 16:
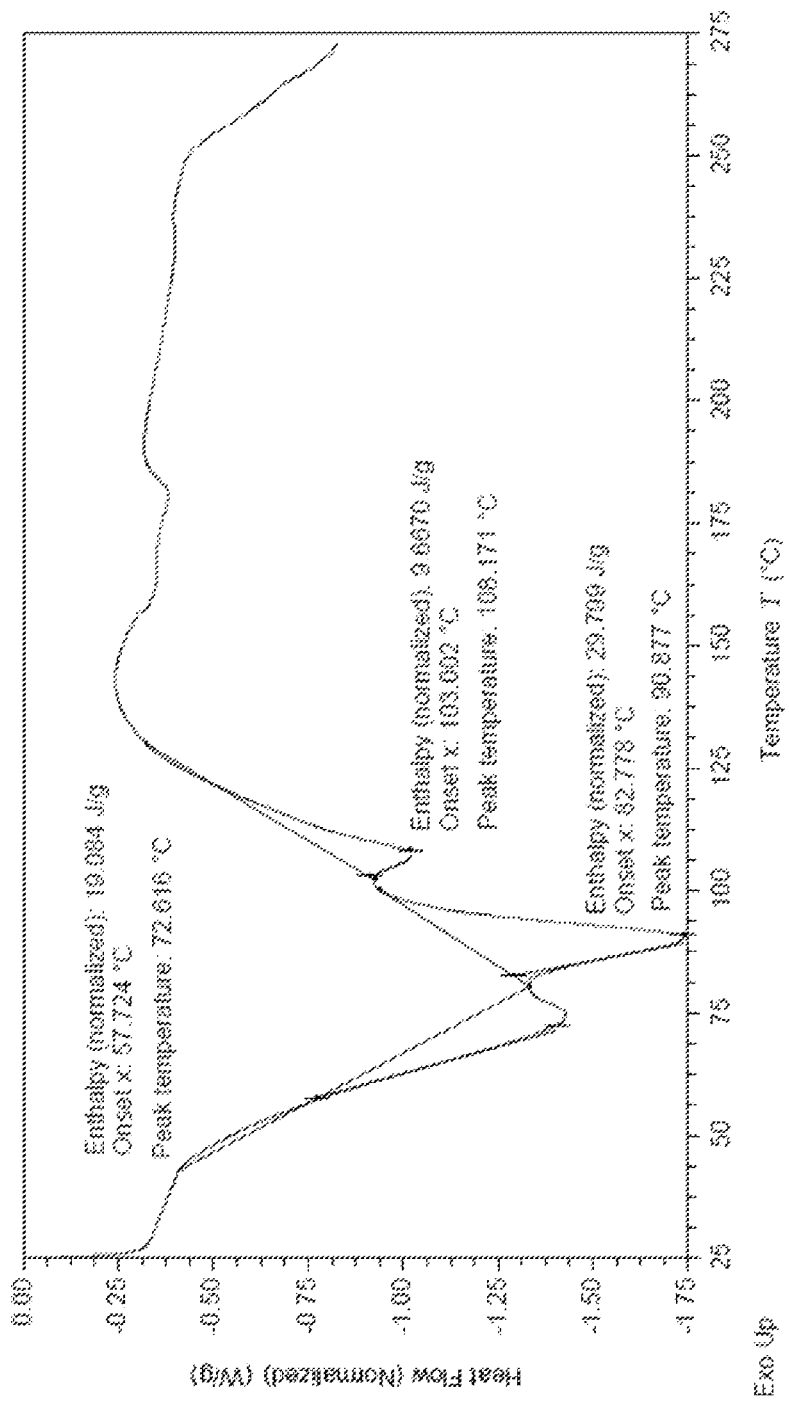
FIG. 16 shows results from DSC of squalamine phosphate, Form 2.
Figure 17:
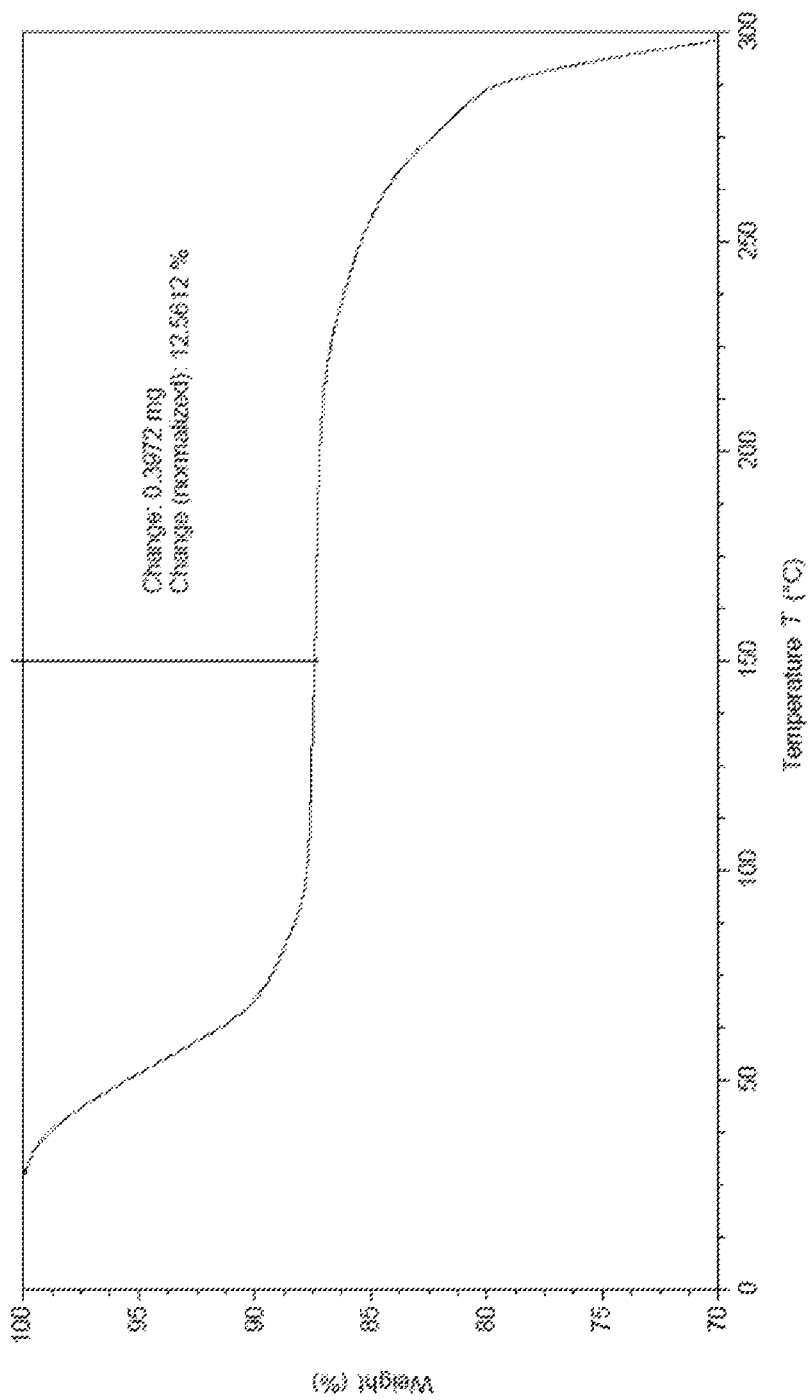
FIG. 17 shows results from TGA of squalamine phosphate, Form 2.

In another aspect, provided herein is an isolated squalamine phosphate solid form designated as Form 2. In some embodiments, the solid form has an X-ray powder diffraction pattern comprising a peak, in terms of 2-theta, at about 15.2° and at about 22.9°. In some embodiments, the solid form has an X-ray powder diffraction pattern comprising a peak, in terms of 2-theta, at about 11.4°, at about 15.2° and at about 22.9°. In some embodiments, the solid form has an X-ray powder diffraction pattern substantially as shown in FIG. 15. In some embodiments, the solid form has a differential scanning calorimetry (DSC) thermogram comprising an endothermic peak at about 90.9° C. In some embodiments, the solid form has a differential scanning calorimetry (DSC) thermogram substantially as shown in FIG. 16. In some embodiments, the solid form has a thermogravimetric analysis (TGA) substantially as shown in FIG. 17.

In another aspect, provided herein is a solid form having an X-ray powder diffraction pattern comprising a peak, in terms of 2-theta, at about 15.2° and at about 22.9°. In some embodiments, the solid form has an X-ray powder diffraction pattern substantially as shown in FIG. 15. In some embodiments, the solid form has a differential scanning calorimetry (DSC) thermogram comprising an endothermic peak at about 90.9° C. In some embodiments, the solid form has a differential scanning calorimetry (DSC) thermogram substantially as shown in FIG. 16. In some embodiments, the solid form has a thermogravimetric analysis (TGA) substantially as shown in FIG. 17.

In another aspect, provided herein is a crystalline squalamine phosphate, characterized by an X-ray powder diffraction pattern comprising the following peaks: about 15.2° 2-theta and at about 22.9° 2-theta, as determined on a diffractometer using Cu-Kα radiation at a wavelength of 1.5406 Å. In some embodiments, the crystalline squalamine phosphate has an X-ray powder diffraction pattern substantially as shown in FIG. 15. In some embodiments, the crystalline squalamine phosphate has a differential scanning calorimetry (DSC) thermogram comprising an endothermic peak at about 90.9° C. In some embodiments, the crystalline squalamine phosphate has a differential scanning calorimetry (DSC) thermogram substantially as shown in FIG. 16. In some embodiments, the crystalline squalamine phosphate has a thermogravimetric analysis (TGA) substantially as shown in FIG. 17. In some embodiments, the X-ray powder diffraction comprises a peak, in terms of 2-theta, at about 11.4°, about 15.2°, and about 22.9°, as determined on a diffractometer using Cu-Kα radiation at a wavelength of 1.5406 Å.

In another aspect, provided herein is a crystalline squalamine phosphate, characterized by (i) an X-ray powder diffraction pattern comprising the following peaks: about 15.2° 2-theta and at about 22.9° 2-theta, as determined on a diffractometer using Cu-Kα radiation at a wavelength of 1.5406 Å; and (ii) a differential scanning calorimetry (DSC) thermogram comprising an endothermic peak at about 90.9° C. In some embodiments, the X-ray powder diffraction comprises a peak, in terms of 2-theta, at about 11.4°, about 15.2°, and about 22.9°, as determined on a diffractometer using Cu-Kα radiation at a wavelength of 1.5406 Å.

In another aspect, provided herein is a crystalline squalamine phosphate, characterized by (i) an X-ray powder diffraction pattern comprising the following peaks: about 15.2° 2-theta and at about 22.9° 2-theta, as determined on a diffractometer using Cu-Kα radiation at a wavelength of 1.5406 Å; (ii) a differential scanning calorimetry (DSC) thermogram comprising an endothermic peak at about 90.9° C.; and (iii) a thermogravimetric analysis (TGA) substantially as shown in FIG. 17. In some embodiments, the X-ray powder diffraction comprises a peak, in terms of 2-theta, at about 11.4°, about 15.2°, and about 22.9°, as determined on a diffractometer using Cu-Kα radiation at a wavelength of 1.5406 Å.

In another aspect, provided herein is a crystalline squalamine phosphate, characterized by (i) an X-ray powder diffraction pattern comprising the following peaks: about 15.2° 2-theta and at about 22.9° 2-theta, as determined on a diffractometer using Cu-Kα radiation at a wavelength of 1.5406 Å; (ii) a differential scanning calorimetry (DSC) thermogram substantially as shown in FIG. 16; and (iii) a thermogravimetric analysis (TGA) substantially as shown in FIG. 17. In some embodiments, the X-ray powder diffraction comprises a peak, in terms of 2-theta, at about 11.4°, about 15.2°, and about 22.9°, as determined on a diffractometer using Cu-Kα radiation at a wavelength of 1.5406 Å.

The squalamine phosphate solid form of Form 2 may have a water content of equal to or greater than about 9%. This includes a water content of about 10%, 11%, or 12%, including increments therein. In some embodiments, the squalamine phosphate solid form of Form 2 has a water content of more than about 10%. In some embodiments, the squalamine phosphate solid form of Form 2 has a water content equal to or greater than about 9%, equal to or greater than about 9.5%, equal to or greater than about 10%, equal to or greater than about 10.5%, equal to or greater than about 11%, equal to or greater than about 11.5%, equal to or greater than about 12%, equal to or greater than about 12.5%, equal to or greater than about 13%, equal to or greater than about 13.5%, equal to or greater than about 14%, equal to or greater than about 14.5%, or up to about 15%, including any amount in-between these values.

The squalamine phosphate solid form of Form 2 may have a water content of about 9% up to about 12%. This includes a water content of about 9%, about 10%, about 11%, or about 12%, including increments therein. In some embodiments, the squalamine phosphate solid form of Form 2 has a water content of about 9% to about 11%, about 9% to about 10%, about 10% to about 11%, about 10% to about 12%, or about 11% to about 12%.

II. Compositions

In another aspect, provided herein are compositions comprising Form 1 and/or Form 2 of squalamine phosphate.

In some embodiments, provided herein are pharmaceutical compositions comprising the squalamine phosphate solid form of Form 1, and one or more pharmaceutically acceptable carriers. In some embodiments, provided herein are pharmaceutical compositions comprising the squalamine phosphate solid form of Form 1, and a pharmaceutically acceptable carrier. In some embodiments, provided herein are pharmaceutical compositions consisting essentially of the squalamine phosphate solid form of Form 1. In some embodiments, provided herein are pharmaceutical compositions consisting of the squalamine phosphate solid form of Form 1 and one or more pharmaceutically acceptable carriers and/or excipients.

In some embodiments, provided herein are pharmaceutical compositions comprising the squalamine phosphate solid form of Form 2, and one or more pharmaceutically acceptable carriers. In some embodiments, provided herein are pharmaceutical compositions comprising the squalamine phosphate solid form of Form 2, and a pharmaceutically acceptable carrier. In some embodiments, provided herein are pharmaceutical compositions consisting essentially of the squalamine phosphate solid form of Form 2. In some embodiments, provided herein are pharmaceutical compositions consisting of the squalamine phosphate solid form of Form 2 and one or more pharmaceutically acceptable carriers and/or excipients.

In some embodiments, provided herein are pharmaceutical compositions comprising squalamine phosphate, wherein the squalamine phosphate in the composition comprises the squalamine phosphate solid form of Form 1 and/or Form 2 in an amount of at least about 88% by weight of the squalamine phosphate in the composition. This includes an amount of about 88%, about 89%, about 90%, about 91%, about 92%, about 93%, about 94%, about 95%, about 96%, about 9%7, about 98%, about 99%, or more, by weight of the squalamine phosphate in the composition, including increments therein.

A. Pharmaceutical Carriers

While it is possible for a squalamine phosphate composition to be administered alone, it is preferable to present it as a pharmaceutical formulation, together with one or more acceptable carriers. The carrier(s) must be "acceptable" in the sense of being compatible with Form 1 and/or Form 2 of squalamine phosphate and not deleterious to the recipients thereof.

Generally, the formulations are prepared by contacting Form 1 and/or Form 2 of squalamine phosphate, uniformly and intimately with liquid carriers or finely divided solid carriers or both. Then, if necessary, the product is shaped into the desired formulation. Non-aqueous vehicles such as fixed oils and ethyl oleate are also useful herein, as well as liposomes.

The carrier suitably comprises minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as gelatin, serum albumin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

In instances where aerosol administration is appropriate, Form 1 and/or Form 2 of squalamine phosphate can be formulated as aerosols using standard procedures. The term "aerosol" includes any gas-borne suspended phase of a compound described herein which is capable of being inhaled into the bronchioles or nasal passages, and includes dry powder and aqueous aerosol, and pulmonary and nasal aerosols. Specifically, aerosol includes a gas-born suspension of droplets of a compound described herein, as may be produced in a metered dose inhaler or nebulizer, or in a mist sprayer. Aerosol also includes a dry powder composition of a composition of the present technology suspended in air or other carrier gas, which may be delivered by insufflation from an inhaler device, for example. See Ganderton & Jones, *Drug Delivery to the Respiratory Tract* (Ellis Horwood, 1987); Gonda, *Critical Reviews in therapeutic Drug*

*Carrier Systems*, 6:273-313 (1990); and Raeburn et al., *Pharmacol. Toxicol. Methods*, 27:143-159 (1992).

B. Dosage Forms

The formulations may conveniently be presented in unit dosage form and may be prepared by any of the methods well known in the art of pharmacy. Any pharmaceutically acceptable dosage form may be employed in the methods of the present technology. For example, the composition can be formulated: (a) for administration selected from the group consisting of oral,-pulmonary, rectal, colonic, parenteral, intracisternal, intravaginal, intraperitoneal, intravenous, subcutaneous, intramuscular, nebulization, inhalation, ocular, otic, local, buccal, nasal, and topical administration; (b) into a dosage form selected from the group consisting of liquid dispersions, gels, aerosols, ointments, creams, lyophilized formulations, tablets, capsules; (c) into a dosage form selected from the group consisting of controlled release formulations, fast melt formulations, delayed release formulations, extended release formulations, pulsatile release formulations, and mixed immediate release and controlled release formulations; or (d) any combination of (a), (b), and (c).

An exemplary dosage form is an orally administered dosage form, such as a tablet or capsule. Such methods include the step of bringing into association Form 1 and/or Form 2 of squalamine phosphate with the carrier that constitutes one or more accessory ingredients. In general, the formulations are prepared by uniformly and intimately bringing into association the active ingredient with liquid carriers or finely divided solid carriers or both, and then, if necessary, shaping the product.

1. Exemplary Dosage Forms

Formulations or compositions of the present technology may be packaged together with, or included in a kit with, instructions or a package insert. For instance, such instructions or package inserts may address recommended storage conditions, such as time, temperature and light, taking into account the shelf-life of Form 1 and/or Form 2 of squalamine phosphate. Such instructions or package inserts may also address the particular advantages of Form 1 and/or Form 2 of squalamine phosphate, such as the ease of storage for formulations that may require use in the field, outside of controlled hospital, clinic or office conditions.

The composition disclosed herein can also be included in nutraceuticals. For instance, the composition may be administered in natural products, including milk or milk product. Form 1 and/or Form 2 of squalamine phosphate can also be provided in powder or tablet form, with or without other known additives, carriers, fillers and diluents. Exemplary nutraceuticals are described in Scott Hegenhart, *Food Product Design*, December 1993.

The composition disclosed herein will be formulated and dosed in a fashion consistent with good medical practice, taking into account the clinical condition of the individual patient (especially the side effects of treatment with the solid form(s) of squalamine phosphate alone), the site of delivery, the method of administration, the scheduling of administration, and other factors known to practitioners. The "effective amount" for purposes herein is thus determined by such considerations.

As a general proposition, the total pharmaceutically effective amount of Form 1 and/or Form 2 of squalamine phosphate administered parenterally per dose will be in the range of about 0.1 mg/kg/day to 20 mg/kg/day of patient body weight, although, as noted above, this will be subject to therapeutic discretion. An intravenous bag solution may also be employed. The length of treatment needed to observe changes and the interval following treatment for responses to occur appears to vary depending on the desired effect.

"Pharmaceutically acceptable carrier" refers to a non-toxic solid, semisolid or liquid filler, diluent, encapsulating material or formulation auxiliary of any type.

For oral administration, the compositions disclosed herein can be formulated by combining Form 1 and/or Form 2 of squalamine phosphate with pharmaceutically acceptable carriers known in the art. Such carriers enable Form 1 and/or Form 2 of squalamine phosphate to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with Form 1 and/or Form 2 of squalamine phosphate, optionally grinding the resulting mixture, and processing the mixture of granules after adding suitable auxiliaries, if desired, to obtain tablets or dragee cores.

Examples of coatings for solid oral formulations include sugar coating and film coating. Film coatings may contain polymers such as, but not limited to, hydroxypropyl methylcellulose (HPMC), methyl hydroxyethyl cellulose, ethylcellulose, povidone, cellulose acetate phthalate, acrylate polymers (e.g., Eudragit L and Eudragit S), and HPMC phthalate.

Form 1 and/or Form 2 of squalamine phosphate is also suitably administered by sustained-release systems. Examples of sustained-release compositions may be administered orally, rectally, parenterally, intracisternally, intravaginally, intraperitoneally, topically (as by powders, ointments, gels, drops or transdermal patch), bucally, or as an oral or nasal spray.

Additional examples of sustained-release compositions include suitable polymeric materials (such as, for example, semi-permeable polymer matrices in the form of shaped articles, e.g., films, or mirocapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman et al., *Biopolymers*, 22:547-556 (1983)), poly (2-hydroxyethyl methacrylate) (Langer et al., *J. Biomed. Mater. Res.*, 15:167-277 (1981), and Langer, *Chem. Tech.*, 12:98-105 (1982)), ethylene vinyl acetate (Langer et al., Id.) or poly-D-(−)-3-hydroxybutyric acid (EP 133,988).

Sustained-release compositions may also include liposomally entrapped compounds described herein (see generally, Langer, *Science*, 249:1527-1533 (1990); Treat et al., in *Liposomes in the Therapy of Infectious Disease and Cancer*, Lopez-Berestein and Fidler (eds.), pp. 317-327 and 353-365 (Liss, N.Y., 1989). Liposomes comprising Form 1 and/or Form 2 of squalamine phosphate may be prepared by methods known per se: DE 3,218,121; Epstein et al., *Proc. Natl. Acad. Sci. (USA)*, 82:3688-3692 (1985); Hwang et al., *Proc. Natl. Acad. Sci. (USA)*, 77:40304034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal therapeutic.

Other controlled release systems are discussed in the review by Langer (*Science* 249:1527-1533 (1990)).

The present technology also provides a pharmaceutical pack or kit comprising one or more containers filled with the composition described herein. Associated with such container(s) can be a notice in the form prescribed by a governmental agency regulating the manufacture, use or sale of pharmaceuticals or biological products, which notice reflects approval by the agency of manufacture, use or sale for human administration. In addition, Form 1 and/or Form 2 of squalamine phosphate may be employed in conjunction with other therapeutic compounds.

2. Other Pharmaceutical Excipients

Pharmaceutical compositions according to the present technology may also comprise one or more binding agents, filling agents, lubricating agents, suspending agents, sweeteners, flavoring agents, preservatives, buffers, wetting agents, disintegrants, effervescent agents, and other excipients. Such excipients are known in the art.

Examples of filling agents include lactose monohydrate, lactose anhydrous, and various starches; examples of binding agents include various celluloses and cross-linked polyvinylpyrrolidone, microcrystalline cellulose, such as AVICEL® PH101 and AVICEL® PH102, microcrystalline cellulose, and silicified microcrystalline cellulose (ProSolv SMCC™).

Suitable lubricants, including agents that act on the flowability of the powder to be compressed, may include colloidal silicon dioxide, such as AEROSIL® 200 (hydrophilic fumed silica), talc, stearic acid, magnesium stearate, calcium stearate, and silica gel.

Examples of sweeteners may include any natural or artificial sweetener, such as sucrose, xylitol, sodium saccharin, cyclamate, aspartame, and acesulfame. Examples of flavoring agents are MAGNASWEET® (trademark of MAFCO), bubble gum flavor, and fruit flavors, and the like.

Examples of preservatives include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as AVICEL® PH101 and AVICEL® PH102; lactose such as lactose monohydrate, lactose anhydrous, and PHARMATOSE® DCL21 (lactose anhydrous NF DCL-21); dibasic calcium phosphate such as EMCOMPRESS®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents include effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

3. Dosages

Examples of dosages of squalamine tolerated by humans are well known in the art. For example, Hao et al., (2003). "A Phase I and pharmacokinetic study of squalamine, an aminosterol angiogenesis inhibitor." Clin Cancer Res 9(7): 2465-71, describes exemplary dosages for a 5-day continuous i.v. infusion every 3 weeks for treating advanced solid malignancies. Dose levels ranging from 6 to 700 mg/m(2)/day. Hepatotoxicity, characterized by brief, asymptomatic elevations in transaminases and hyperbilirubinemia, was the principal dose-limiting toxicity of squalamine. At 700 mg/m(2)/day, two of three patients developed grade 4 hyperbilirubinemia, which precluded further dose escalation. At 500 mg/m(2)/day, one of seven patients experienced dose-limiting grade 4 hyperbilirubinemia and grade 3 neurosensory changes, which resolved soon after treatment. Squalamine pharmacokinetics were dose-proportional. At 500 mg/m(2)/day, the mean (percentage coefficient of variation) clearance, half-life, and volume of distribution of squalamine were 2.67 liters/h/m(2) (85%), 9.46 h (81%), and 36.84 liters/m(2) (124%), respectively, and steady-state concentrations [20.08 micro g/ml (13%)] were well above those that inhibit angiogenesis in preclinical models. The study concluded that at a dose of 500 mg/m(2)/day, squalamine is well tolerated.

In addition, Herbst et al., (2003). "A phase I/IIA trial of continuous five-day infusion of squalamine lactate (MSI-1256F) plus carboplatin and paclitaxel in patients with advanced non-small cell lung cancer." Clin Cancer Res 9(11): 4108-15, also describes exemplary therapeutic dosage of squalamine. This reference describes a Phase I/IIA study designed to assess the safety, clinical response, and pharmacokinetics of squalamine when administered as a 5-day continuous infusion in conjunction with standard chemotherapy every 3 weeks in patients with stage IIIB (pleural effusion) or stage IV non-small cell lung cancer. Patients with chemotherapy-naive non-small cell lung cancer were treated with escalating doses of squalamine in combination with standard doses of paclitaxel and carboplatin. Paclitaxel and carboplatin were administered on day 1, followed by squalamine as a continuous infusion on days 1-5, every 21 days. The starting dose of squalamine was 100 mg/m(2)/day and escalated to 400 mg/m(2)/day; two of three patients at 400 mg/m(2)/day had dose-limiting toxicity that included grade 3/4 arthralgia, myalgia, and neutropenia. On the basis of safety and toxicity, 300 mg/m(2)/day was selected as the Phase II dose of squalamine in this combination regimen. The combination of squalamine given continuously daily for 5 days, with paclitaxel and carboplatin given on day 1, was well tolerated.

C. Adjuvants

Form 1 and/or Form 2 of squalamine phosphate may be administered alone or in combination with one or more adjuvants. For example, for antiviral applications, an adjuvant is a substance that indirectly enhances the therapeutic activity of the squalamine phosphate by stimulating the antiviral arm of the innate and/or the adaptive immune system. Adjuvants that may be administered with Form 1 and/or Form 2 of squalamine phosphate include, but are not limited to, cytokines and/or interleukins (such as IL2, IL3, IL4, IL5, IL6, IL7, IL8, IL-9, IL10, IL-11, IL12, IL13, IL-14, IL15, IIL16, IL-17, IL-18, IL-19, IL-20, IL-21, anti-CD40, CD40L, IFN-gamma, TNF-alpha, IL-Ialpha, IL-1beta), Lipid A, including monophosphoryl lipid A, bacterial products, endotoxins, cholesterol, fatty acids, aliphatic amines, paraffinic and vegetable oils, threonyl derivative, and muramyl dipeptide, alum, alum plus deoxycholate (ImmunoAg), MTP-PE (Biocine Corp.), QS21 (Genentech, Inc.), BCG (e.g., THERACYS®), MPL and nonviable preparations of *Corynebacterium parvum*. In a specific embodiment, Form 1 and/or Form 2 of squalamine phosphate is administered in combination with alum. In another specific embodiment, Form 1 and/or Form 2 of squalamine phosphate is administered in combination with QS-21. Further adjuvants that may be administered with Form 1 and/or Form 2 of squalamine phosphate include, but are not limited to, Monophosphoryl lipid immunomodulator, AdjuVax 100a, QS-21, QS-18, CRL1005, Aluminum salts, MF-59, and Virosomal adjuvant technology.

D. Vaccines

Vaccines that may be administered with Form 1 and/or Form 2 of squalamine phosphate include any antigen capable of eliciting an immune response. The vaccine may be comprised of either live or inactivated virus. Exemplary vaccines include, but are not limited to, vaccines directed toward protection against MMR (measles, mumps, rubella), polio, varicella, tetanus/diptheria, hepatitis A, hepatitis B, *Haemophilus influenzae* B, whooping cough, pneumonia, influenza, Lyme's Disease, rotavirus, cholera, yellow fever, Japanese encephalitis, poliomyelitis, rabies, typhoid fever, pertussis, PA-toxin (e.g., anthrax), Human Immunodeficiency Virus (HIV-1 and HIV-2), Avian Flu antigen (e.g., H5N1; avian influenza virus A/FPV/Rostock/34 (H7N1) (FPV)), cancer, Severe Acute Respiratory Syndrome (SARS), and tuberculosis. Useful antigens include but are not limited to viral, prion, bacterial, parasitic, mycotic, etc. antigens.

Combinations may be administered either concomitantly, e.g., as an admixture, separately but simultaneously or concurrently; or sequentially. In addition, as used herein "combination administration" includes compounds which are attached to Form 1 and/or Form 2 of squalamine phosphate This also includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

E. Combination Therapy

The squalamine phosphate compositions of the present technology may be administered alone or in combination with other therapeutic agents. As noted above, the squalamine phosphate compositions of the present technology are useful in treating and/or preventing: (1) viral infections, (2) antimicrobial infections, including but not limited to Gram-negative and Gram-positive bacterial infections, fungal infections, and protozoan infections; (3) disease states known to be associated with pathological neovascularization, such as cancer, due to squalamine's anti-angiogenic properties; (4) vascular disorders of the eye, including macular degeneration, such as age-related macular degeneration, retinopathy of prematurity, corneal neovascularization, diabetic retinopathy; (5) weight loss or weight management, dose-dependent weight loss; (6) diseases, including viral infections, where sodium-hydrogen exchanger ("NHE-3") plays a critical role, and where its inhibition (by squalamine) could be effected; and (7) treatment of fibrodysplasia ossificans progressiva, a rare disease where connective tissue will ossify when damaged. Thus, any active agent known to be useful in treating these conditions can be used in conjunction with the squalamine phosphate compositions of the present technology. For example, in methods of treating a microbial infection, the squalamine phosphate compositions of the present technology can be co-administered or combined with an antibiotic.

For treating a viral infection, the squalamine phosphate compositions of the present technology can be co-administered or combined with an antiviral agent, etc.

For example, the squalamine phosphate compositions described herein may be administered in combination compounds including but not limited to, chemotherapeutic agents, antibiotics, steroidal and non-steroidal anti-inflammatories, conventional immunotherapeutic agents, antiviral agents, and/or therapeutic treatments described below. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

1. Anti-Viral Agents

For example, squalamine phosphate compositions of the present technology can be combined with conventional antiviral therapies for treating and preventing viral infections. For example, the squalamine phosphate compositions of the present technology can be combined with any known antiviral agent.

Designing safe and effective antiviral drugs is difficult, because viruses use the host's cells to replicate. This makes it difficult to find targets for the drug that would interfere with the virus without harming the host organism's cells. Almost all anti-microbials, including anti-viralsa, are subject to drug resistance as the pathogens mutate over time, becoming less susceptible to the treatment. For instance, a recent study published in Nature Biotechnology emphasized the urgent need for augmentation of oseltamivir (TAMIFLU®) stockpiles with additional antiviral drugs including zanamivir (RELENZA®) based on an evaluation of the performance of these drugs in the scenario that the 2009 H1N1 'Swine Flu' neuraminidase (NA) were to acquire the TAMIFLU®-resistance (His274Tyr) mutation which is currently wide-spread in seasonal H1N1 strains. Soundararajan et al., "Extrapolating from sequence the 2009 H1N1 'swine' influenza virus". Nature Biotechnology 27 (6) (2009). Thus, there is a need for compositions, such as those described herein, which are useful in conjunction with conventional antiviral treatments.

Conventional antiviral treatments include, but are not limited to (1) Amantadine and rimantadine, which combat influenza and act on penetration/uncoating; (2) Pleconaril, which works against rhinoviruses, which cause the common cold; (3) nucleotide or nucleoside analogues, such as acyclovir, zidovudine (AZT), lamivudine; (4) drugs based on "antisense" molecules, such as fomivirsen; (5) ribozyme antivirals; (6) protease inhibitors; (7) assembly inhibitors, such as Rifampicin; (8) release phase inhibitors, such as zanamivir (Relenza) and oseltamivir (Tamiflu); (9) drugs which stimulate the immune system, such as interferons, which inhibit viral synthesis in infected cells (e.g., interferon alpha), and synthetic antibodies (A monoclonal drug is now being sold to help fight respiratory syncytial virus in babies, and antibodies purified from infected individuals are also used as a treatment for hepatitis B). Examples of antiviral drugs include, but are not limited to, Abacavir, Aciclovir, Acyclovir, Adefovir, Amantadine, Amprenavir, Arbidol, Atazanavir, Atripla, Boceprevir, Cidofovir, Combivir, Darunavir, Delavirdine, Didanosine, Docosanol, Edoxudine, Efavirenz, Emtricitabine, Enfuvirtide, Entecavir, Entry inhibitors, Famciclovir, Fixed dose combination (antiretroviral), Fomivirsen, Fosamprenavir, Foscarnet, Fosfonet, Fusion inhibitor, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Molixan (NOV-205), Moroxydine, Nelfinavir, Nevirapine, Nexavir, Nucleoside analogues, Oseltamivir (Tamiflu), Peginterferon alfa-2a, Penciclovir, Peramivir, Pleconaril, Podophyllotoxin, Protease inhibitor (pharmacology), Raltegravir, Reverse transcriptase inhibitor, Ribavirin, Rimantadine, Ritonavir, Saquinavir, Stavudine, Synergistic enhancer (antiretroviral), Tenofovir, Tenofovir disoproxil, Tipranavir, Trifluridine, Trizivir, Tromantadine, Truvada, Valaciclovir (Valtrex), Valganciclovir, Vicriviroc, Vidarabine, Viramidine, Zalcitabine, Zanamivir (Relenza), and Zidovudine In certain embodiments, Form 1 and/or Form 2 of squalamine phosphate is administered in combination with antiretroviral agents, nucleoside/nucleotide reverse transcriptase inhibitors (NRTIs), non-nucleoside reverse transcriptase inhibitors (NNRT1s), and/or protease inhibitors (PIs). NRTIs that may be administered in combination with Form 1 and/or Form 2 of squalamine phosphate, include, but are not limited to, RETROVIR™ (zidovudine/AZT), VIDEX™ (didanosineIddI), HIVID™ (zalcitabine/ddC), ZERIT™ (stavudine/d4T), EPIVIR™ (lamivudine/3TC), and COMBIVIR™ (zidovudine/lamivudine). NNRTIs that may be administered in combination with squalamine composition, include, but are not limited to, VIRAMUNE™ (nevirapine), RESCRIPTOR™ (delavirdine), and SUSTIVA™ (efavirenz). Protease inhibitors that may be administered in combination with Form 1 and/or Form 2 of squalamine phosphate include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with Form 1 and/or Form 2 of squalamine phosphate to treat AIDS and/or to prevent or treat HIV infection.

Additional NRTIs include LODENOSINE™ (F-ddA; an acid-stable adenosine NRTI; Triangle/Abbott; COVIRACIL™ (emtricitabine/FTC; structurally related to lamivudine (3TC) but with 3-to 10-fold greater activity in vitro; Triangle/Abbott); dOTC (BCH-10652, also structurally related to lamivudine but retains activity against a substantial proportion of lanivudine-resistant isolates; Biochem Pharma); Adefovir (refused approval for anti-HIV therapy by FDA; Gilead Sciences); PREVEON® (Adefovir Dipivoxil, the active prodrug of adefovir; its active form is PMEA-pp); TENOFOVIR™ (bis-POC PMPA, a PMPA prodrug; Gilead); DAPD/DXG (active metabolite of DAPD; Triangle/Abbott); D-D4FC (related to 3TC, with activity against AZT/3TC-resistant virus); GW420867 (Glaxo Wellcome); ZIAGEN™ (abacavir/159U89; Glaxo Wellcome Inc.); CS-87 (3'azido-2',3'-dideoxyuridine; WO 99/66936); and S-acyl-2-thioethyl (SATE)-bearing prodrug forms of beta-L-FD4C and P-L-FddC (WO 98/17281).

Additional NNRTIs include COACTINON™ (Emivirine/MKC442, potent NNRTI of the HEPT class; Triangle/Abbott); CAPRAVIRINE™ (AG-1549/S-1153, a next generation NNRTI with activity against viruses containing the K103N mutation; Agouron); PNU-142721 (has 20- to 50-fold greater activity than its predecessor delavirdine and is active against K103N mutants; Pharmacia & Upjohn); DPC-961 and DPC-963 (second-generation derivatives of efavirenz, designed to be active against viruses with the K103N mutation; DuPont); GW420867X (has 25-fold greater activity than HBY097 and is active against K103N mutants; Glaxo Wellcome); CALANOLIDE A (naturally occurring agent from the latex tree; active against viruses containing either or both the Y181C and K103N mutations); and Propolis (WO 99/49830).

Additional protease inhibitors include LOPINAVIR™ (ABT378/r; Abbott Laboratories); BMS-232632 (an azapeptide; Bristol-Myres Squibb); TIPRANAVIR™ (PNU-140690, a non-peptic dihydropyrone; Pharmacia & Upjohn); PD-178390 (a nonpeptidic dihydropyrone; Parke-Davis); BMS 232632 (an azapeptide; Bristol-Myers Squibb); L-756, 423 (an indinavir analog; Merck); DMP450 (a cyclic urea compound; Avid & DuPont); AG-1776 (a peptidomimetic with in vitro activity against protease inhibitor-resistant viruses; Agouron); VX-175/GW433908 (phosphate prodrug of amprenavir; Vertex & Glaxo Welcome); CGP61755 (Ciba); and AGENERASE™ (amprenavir; Glaxo Wellcome Inc.).

Additional antiretroviral agents include fusion inhibitors/gp41 binders. Fusion inhibitors/gp41 binders include T-20 (a peptide from residues 643-678 of the HIV gp41 transmembrane protein ectodomain which binds to gp41 in its resting state and prevents transformation to the fusogenic state; Trimeris) and T-1249 (a second-generation fusion inhibitor; Trimeris).

Additional antiretroviral agents include fusion inhibitors/chemokine receptor antagonists. Fusion inhibitors/chemokine receptor antagonists include CXCR4 antagonists such as AMD 3100 (a bicyclam), SDF-1 and its analogs, and ALX404C (a cationic peptide), T22 (an 18 amino acid peptide; Trimeris) and the T22 analogs T134 and T140; CCR5 antagonists such as RANTES (9-68), AOP-RANTES, NNY-RANTES, and TAK-779; and CCR5/CXCR4 antagonists such as NSC 651016 (a distamycin analog). Also included are CCR2B, CCR3, and CCR6 antagonists. Chemokine receptor agonists such as RANTES, SDF-1, MEP-1alpha, MIP-1beta, etc., may also inhibit fusion.

Additional antiretroviral agents include integrase inhibitors. Integrase inhibitors include dicaffeoylquinic (DFQA) acids; L-chicoric acid (a dicaffeoyltartaric (DCTA) acid); quinalizarin (QLC) and related anthraquinones; ZINTEVIR™ (AR 177, an oligonucleotide that probably acts at cell surface rather than being a true integrase inhibitor; Arondex); and naphthols such as those disclosed in WO 98/50347.

Additional antiretroviral agents include hydroxyurea-like compounds such as BCX-34 (a purine nucleoside phosphorylase inhibitor; Biocryst); ribonucleotide reductase inhibitors such as DIDOX™ (Molecules for Health); inosine monophosphate dehydrogenase (IMPDH) inhibitors such as VX-497 (Vertex); and mycopholic acids such as CellCept (mycophenolate mofetil; Roche).

Additional antiretroviral agents include inhibitors of viral integrase, inhibitors of viral genome nuclear translocation such as arylene bis(methylketone) compounds; inhibitors of HIV entry such as AOP-RANTES, NNY-RANTES, RANTES-IgG fusion protein, soluble complexes of RANTES and glycosaminoglycans (GAG), and AMD-3100; nucleocapsid zinc finger inhibitors such as dithiane compounds; targets of HIV Tat and Rev; and pharmacoenhancers such as ABT-378.

Other antiretroviral therapies and adjunct therapies include cytokines and lymphokines such as MIP-1alpha, MIP-1beta, SDF-1alpha, IL-2, PROLEUKIN™ (aldesleukin/L2-7001; Chiron), IL4, IL-10, IL-12, and IL-13; interferons such as IFN-alpha2a, IFN-alpha2b, or IFN-beta;

antagonists of TNFs, NFkappaB, GM-CSF, M-CSF, and IL-10; agents that modulate immune activation such as cyclosporin and prednisone; vaccines such as Remune™ (HIV Immunogen), APL 400-003 (Apollon), recombinant gp120 and fragments, bivalent (B/E) recombinant envelope glycoprotein, rgp120CM235, MN rgp120, SF-2 rgp120, gp120/soluble CD4 complex, Delta JR-FL protein, branched synthetic peptide derived from discontinuous gp120 C3/C4 domain, fusion-competent immunogens, and Gag, Pol, Nef, and Tat vaccines; gene-based therapies such as genetic suppressor elements (GSEs; WO 98/54366), and intrakines (genetically modified CC chemokines targeted to the ER to block surface expression of newly synthesized CCR5 (Yang et al., PNAS, 94:11567-72 (1997); Chen et al., Nat. Med., 3:1110-16 (1997)); antibodies such as the anti-CXCR4 antibody 12G5, the anti-CCR5 antibodies 2D7, 5C7, PA8, PA9, PA10, PA11, PA12, and PA14, the anti-CD4 antibodies Q4120 and RPA-T4, the anti-CCR3 antibody 7B11, the anti-gp120 antibodies 17b, 48d, 447-52D, 257-D, 268-D and 50.1, anti-Tat antibodies, anti-TNF-alpha antibodies, and monoclonal antibody 33A; aryl hydrocarbon (AH) receptor agonists and antagonists such as TCDD, 3,3',4,4',5-pentachlorobiphenyl, 3,3',4,4'-tetrachlorobiphenyl, and alpha-naphthoflavone (WO 98/30213); and antioxidants such as gamma-L-glutamyl-L-cysteine ethyl ester (gamma-GCE; WO 99/56764).

2. Anti-inflammatory Agents

In certain embodiments, the squalamine phosphate composition described herein is administered alone or in combination with an anti-inflammatory agent. Anti-inflammatory agents that may be administered with the squalamine phosphate compositions described herein include, but are not limited to, corticosteroids (e.g., betamethasone, budesonide, cortisone, dexamethasone, hydrocortisone, methylprednisolone, prednisolone, prednisone, and triamcinolone), nonsteroidal anti-inflammatory drugs (e.g., diclofenac, diflunisal, etodolac, fenoprofen, floctafenine, flurbiprofen, ibuprofen, indomethacin, ketoprofen, meclofenamate, mefenamic acid, meloxicam, nabumetone, naproxen, oxaprozin, phenylbutazone, piroxicam, sulindac, tenoxicam, tiaprofenic acid, and tolmetin), as well as antihistamines, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

3. Antibiotic Agents

In certain embodiments, the squalamine phosphate composition described herein is administered alone or in combination with one or more antibiotics. Examples of such antibiotic agents include, but are not limited to, aminoglycosides, Ansamycins, Carbacephems, Carbapenems, Cephalosporins, Glycopeptides, Macrolides, Monobactams, Penicillins, Polypeptides, Polymyxin, Quinolones, Sulfonamides, Tetracyclines, and others (e.g., Arsphenamine, Chloramphenicol, Clindamycin, Lincomycin, Ethambutol, Fosfomycin, Fusidic acid, Furazolidone, Isoniazid, Linezolid, Metronidazole, Mupirocin, Nitrofurantoin, Platensimycin, Pyrazinamide, Quinupristin/Dalfopristin, Rifampicin (Rifampin in US), Thiamphenicol, Tinidazole, Dapsone, and lofazimine).

Examples of these classes of antibiotics include, but are not limited to, Amikacin, Gentamicin, Kanamycin, Neomycin, Netilmicin, Streptomycin, Tobramycin, Paromomycin, Geldanamycin, Herbimycin, Loracarbef, Ertapenem, Doripenem, Imipenem/Cilastatin, Meropenem, Cefadroxil, Cefazolin, Cefalotin or Cefalothin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftobiprole, Teicoplanin, Vancomycin, Azithromycin, Clarithromycin, Dirithromycin, Erythromycin, Roxithromycin, Troleandomycin, Telithromycin, Spectinomycin, Aztreonam, Amoxicillin, Ampicillin, Azlocillin, Carbenicillin, Cloxacillin, Dicloxacillin, Flucloxacillin, Mezlocillin, Meticillin, Nafcillin, Oxacillin, Penicillin, Piperacillin, Ticarcillin, Bacitracin, Colistin, Polymyxin B, Ciprofloxacin, Enoxacin, Gatifloxacin, Levofloxacin, Lomefloxacin, Moxifloxacin, Norfloxacin, Ofloxacin, Trovafloxacin, Grepafloxacin, Sparfloxacin, Temafloxacin, Mafenide, Sulfonamidochrysoidine (archaic), Sulfacetamide, Sulfadiazine, Sulfamethizole, Sulfanilimide (archaic), Sulfasalazine, Sulfisoxazole, Trimethoprim, rimethoprim-Sulfamethoxazole (Co-trimoxazole) (TMP-SMX), Demeclocycline, Doxycycline, Minocycline, Oxytetracycline, and Tetracycline.

4. Antifungal Agents

In certain embodiments, the squalamine phosphate composition described herein is administered alone or in combination with one or more antifungal, antiyeast or antimold agents.

Exemplary active agents include, but are not limited to, (1) azoles (imidazoles), (2) antimetabolites, (3) allylamines, (4) morpholine, (5) glucan Synthesis Inhibitors (chemical family: echinocandins), (6) polyenes, (7) benoxaborales, (8) other antifungal/onychomycosis agents, and (9) new classes of antifungal/onychomycosis agents.

Examples of azoles include, but are not limited to, Bifonazole, Clotrimazole, Econazole, Miconazole, Tioconazole, Fluconazole, Itraconazole, Ketoconazole, Pramiconazole, Ravuconazole, Posaconazole, and Voriconazole. An example of an antimetabolite includes, but is not limited to, Flucytosine. Examples of allylamines include, but are not limited to, Terbinafine and Naftidine. Morpholine is also known as amorolfine. Examples of glucan Synthesis Inhibitors include, but are not limited to, Caspofungin, Micafungin, and Anidulafungin. Examples of polyenes include, but are not limited to, Amphotericin B, Nystatin, and pimaricin. An example of a benoxaborale is AN2690. Other examples of antifungal agents include, but are not limited to, griseofulvin and ciclopirox. Finally, examples of new classes of antifungal/onychomycosis agents include, but are not limited to, sodarin derivatives and nikkomycins.

5. Anticancer Agents

In certain embodiments, the squalamine phosphate composition described herein is administered alone or in combination with one or more anticancer agents. For example, the anticancer agent may be a nitrosourea (such as BCNU), cyclophosphamide, adriamycin, 5-fluorouracil, paclitaxel and its derivatives, cisplatin or other platinum containing cancer treating agents. There are no limitations on the chemotherapeutic agent that can be used in this present technology. Other conventional chemotherapeutic agents that can be used with the squalamine phosphate composition of the present technology include, for example, methotrexate, thiotepa, mitoxantrone, vincristine, vinblastine, etoposide, ifosfamide, bleomycin, procarbazine, chlorambucil, fludarabine, mitomycin C, vinorelbine, and gemcitabine.

The majority of chemotherapeutic drugs can be divided in to alkylating agents, antimetabolites, anthracyclines, plant alkaloids, topoisomerase inhibitors, and other antitumour agents. All of these drugs affect cell division or DNA synthesis and function in some way. Some newer agents do not directly interfere with DNA. These include monoclonal antibodies and the new tyrosine kinase inhibitors e.g. imatinib mesylate (Gleevec or Glivec), which directly targets a molecular abnormality in certain types of cancer (chronic myelogenous leukemia, gastrointestinal stromal tumors). In addition, some drugs that modulate tumor cell behaviour without directly attacking those cells may be used. Hormone treatments fall into this category.

Alkylating agents: Alkylating antineoplastic agents are so named because of their ability to add alkyl groups to many electronegative groups under conditions present in cells. Cisplatin and carboplatin, as well as oxaliplatin, are alkylating agents. Other agents are mechlorethamine, cyclophosphamide, chlorambucil, ifosfamide.

Anti-metabolites: Plant alkaloids and terpenoids are derived from plants and block cell division by preventing microtubule function. The main examples are vinca alkaloids and taxanes. Vinca alkaloids include Vincristine, Vinblastine, Vinorelbine, and Vindesine. Podophyllotoxin is used to produce two other cytostatic drugs, etoposide and teniposide. The prototype taxane is the natural product paclitaxel. Docetaxel is a semi-synthetic analogue of paclitaxel.

Topoisomerase inhibitors include camptothecins (irinotecan and topotecan, amsacrine, etoposide, etoposide phosphate, teniposide, dactinomycin, doxorubicin, epirubicin, bleomycin and others.

6. Weight Loss Agents

In certain embodiments, the squalamine phosphate composition described herein is administered alone or in combination with one or more appetite suppressants or weight loss agents.

7. Neurologically Directed Agents

In certain embodiments, the squalamine phosphate composition described herein is administered alone or in combination with one or more agents targeting a neurological condition. The methods of the invention are useful in treating and/or preventing the conditions described herein, including but not limited to neurological disorders, such as Parkinson's disease, autism, multiple system atrophy, depression, Alzheimer's disease, Huntington's Disease, schizophrenia, multiple sclerosis, and degenerative processes associated with aging, autonomic system instability, including delays in sleep onset, fragmentation of sleep, reduced REM sleep, reduced total sleep time, REM-behavior disorder, sleep breathing disorder including snoring and sleep apnea, hallucinations, narcolepsy, and day-time sleepiness.

8. Gastrointestinal Disorders

In certain embodiments, the squalamine phosphate composition described herein is administered alone or in combination with one or more agents used to treat gastronintestinal disorders such as constipation, Crohn's disease or IBS. Thus, any active agent known to be useful in treating these conditions can be used in the disclosed, and either combined with the aminosterol compositions used in the methods, or administered separately or sequentially.

III. Methods of Using the Compositions of the Present Technology

The present technology also provides methods of treatment and/or prevention of diseases or disorders (such as, for example, any one or more of the diseases or disorders disclosed herein) by administration to a subject of an effective amount of Form 1 and/or Form 2 of squalamine phosphate in one or more pharmaceutically acceptable carriers. The compositions of the present technology can be administered using any pharmaceutically acceptable method, including but not limited to oral, pulmonary, nasal, and nebularization administration.

The squalamine phosphate compositions of the present technology can be used to treat any indication known to be amenable to treatment with squalamine. The squalamine phosphate compositions of the present technology can be used to treat, for example, (1) viral infections, (2) antimicrobial infections, including but not limited to treating and/or preventing Gram-negative and Gram-positive bacterial infections, fungal infections, and protozoan infections; (3) disease states known to be associated with pathological neovascularization, such as cancer, due to squalamine's anti-angiogenic properties; (4) vascular disorders of the eye, including macular degeneration, such as age-related macular degeneration, retinopathy of prematurity, corneal neovascularization, diabetic retinopathy; (5) weight loss or weight management, dose-dependent weight loss; (6) diseases, including viral infections, where sodium-hydrogen exchanger ("NHE-3") plays a critical role, and where its inhibition (by squalamine) could be effected; (7) treatment of fibrodysplasia ossificans progressiva, a rare disease where connective tissue will ossify when damaged; (8) disorders of neovascularization; (9) disorders of gastrointestinal motility, such as chronic idiopathic constipation, opioid induced constipation, irritable bowel syndrome, and inflammatory bowel disease; (10) diabetes mellitus and diabetic neuropathy; (11) disorders of the nervous system that could benefit from neuro-protection, such as Parkinson's Disease, Alzheimer's disease, Huntington's Disease, acute traumatic injury to the central nervous system, including the spinal cord, stroke, acute head and/or spine injury, degenerative processes associated with aging, including memory loss ("dementia of aging"), cerebral palsy, epilepsy, peripheral sensory neuropathy, and multiple sclerosis;(12) autism; (13) sleep disorders; (14) schizophrenia; (15) depression; and (16) autonomic system lability.

Accordingly, in some embodiments, provided herein are methods for treating a subject in need having a condition susceptible to treatment with an aminosterol, comprising administering to the subject a therapeutically effective amount of a squalamine phosphate solid form of Form 1 and/or Form 2. In some embodiments, provided herein are methods for treating a subject in need having a condition susceptible to treatment with an aminosterol, comprising administering to the subject a therapeutically effective amount of a composition comprising or consisting essentially of a squalamine phosphate solid form of Form 1 and/or Form 2, and one or more pharmaceutically acceptable carriers and/or excipients. In some embodiments, the subject in need has a condition selected from the group consisting of viral infections, antimicrobial infections, Gram-negative and Gram-positive bacterial infections, Mycobacteria infections, fungal infections, protozoan infections, disease states known to be associated with pathological neovascularization, such as cancer, vascular disorders of the eye, including macular degeneration, such as age-related macular degeneration, retinopathy of prematurity, corneal neovascularization, diabetic retinopathy, weight loss or weight management, dose-dependent weight loss; diseases, including viral infections, where sodium-hydrogen exchanger ("NHE-3") plays a critical role, treatment of fibrodysplasia ossificans progressiva, and disorders of neovascularization. In some embodiments, the viral infection is caused by a virus selected from the group consisting of Yellow Fever, Cytomegalovirus, Eastern Equine Encephalitis virus, Hepatitis B virus, Hepatitis Delta virus, Dengue virus, and Human Immunodeficiency virus. In some embodiments, the condition to be treated is a viral infection caused by a virus selected from the group consisting of "African Swine Fever Viruses," Arbovirus, Adenoviridae, Arenaviridae, Arterivirus, Astroviridae, Baculoviridae, Bimaviridae, Birnaviridae, Bunyaviridae, Caliciviridae, Caulimoviridae, Circoviridae, Coronaviridae, Cystoviridae, Dengue, EBV, HIV, Deltaviridae, Filviridae, Filoviridae, Flaviviridae, Hepadnaviridae (Hepatitis), Herpesviridae (such as, Cytomegalovirus, Herpes Simplex, Herpes Zoster), Iridoviridae, Mononegavirus (e.g., Paramyxoviridae, Morbillivirus, Rhabdoviridae), Myoviridae, Orthomyxoviridae (e.g., Influenza A, Influenza B, and parainfluenza), Papiloma virus, Papovaviridae, Paramyxoviridae, Prions, Parvoviridae, Phycodnaviridae, Picomaviridae (e.g., Rhinovirus, Poliovirus), Poxviridae (such as Smallpox or Vaccinia), Potyviridae, Reoviridae (e.g., Rotavirus), Retroviridae (HTLV-I, HTLV-II, Lentivirus), Rhabdoviridae, Tectiviridae, Togaviridae (e.g., Rubivirus), herpes, pox, papilloma, corona, influenza, hepatitis, sendai, sindbis, vaccinia viruses, west nile, hanta, viruses which cause the common cold, and any combination thereof. In some embodiments, the condition to be treated is selected from the group consisting of AIDS, viral meningitis, Dengue, EBV, hepatitis, a chronic disease suspected to be of viral origin, multiple sclerosis, Type I diabetes, Type II diabetes, atherosclerosis, cardiomyopathies, Kawaski disease, aplastic anemia, and any combination thereof. In some embodiments, the method further comprises administering an additional active agent, wherein the additional active agent is administered via a method selected from the group consisting of (a) concomitantly; (b) as an admixture; (c) separately and simultaneously or concurrently; and (d) separately and sequentially. In some embodiments, the subject is human.

A. Treating Viral Infections

In some embodiments, provided herein are methods of treating and/or preventing viral infections comprising administering a therapeutically effective amount of a squalamine phosphate composition disclosed herein to a subject in need. A "subject in need" is a human or animal at risk of a viral infection, or which has contracted a viral infection. As noted above, this method encompasses using a squalamine phosphate composition described herein in combination with conventional antiviral treatments to treat viral infections.

The viral infection to be treated or prevented can be caused by any virus, including but not limited to, "African Swine Fever Viruses," Arbovirus, Adenoviridae, Arenaviridae, Arterivirus, Astroviridae, Baculoviridae, Bimaviridae, Birnaviridae, Bunyaviridae, Caliciviridae, Caulimoviridae, Circoviridae, Coronaviridae, Cystoviridae, Dengue, EBV, HIV, Deltaviridae, Filviridae, Filoviridae, Flaviviridae, Hepadnaviridae (Hepatitis), Herpesviridae (such as, Cytomegalovirus, Herpes Simplex, Herpes Zoster), Iridoviridae, Mononegavirus (e.g., Paramyxoviridae, Morbillivirus, Rhabdoviridae), Myoviridae, Orthomyxoviridae (e.g., Influenza A, Influenza B, and parainfluenza), Papiloma virus, Papovaviridae, Paramyxoviridae, Prions, Parvoviridae, Phycodnaviridae, Picomaviridae (e.g., Rhinovirus, Poliovirus), Poxviridae (such as Smallpox or Vaccinia), Potyviridae, Reoviridae (e.g., Rotavirus), Retroviridae (HTLV-I, HTLV-II, Lentivirus), Rhabdoviridae, Tectiviridae, Togaviridae (e.g., Rubivirus), or any combination thereof. In another embodiment of the present technology, the viral infection is caused by a virus selected from the group consisting of herpes, pox, papilloma, corona, influenza, hepatitis, sendai, sindbis, vaccinia viruses, west nile, hanta, or viruses which cause the common cold. In another embodiment of the present technology, the condition to be treated is selected from the group consisting of AIDS, viral meningitis, Dengue, EBV, hepatitis, and any combination thereof.

In one embodiment of the present technology, the condition to be treated is a chronic disease suspected to be of viral origin. For example, the condition to be treated can be multiple sclerosis, Type I diabetes, Type II diabetes, atherosclerosis, cardiomyopathies, Kawaski disease, aplastic anemia, etc.

In another embodiment of the present technology, combination methods of treating or preventing a viral infection are described. The combination methods comprise: (1) administering a therapeutically effective amount of Form 1 and/or Form 2 of squalamine phosphate to a subject in need; and (2) administering a conventional antiviral drug. The squalamine composition and conventional antiviral drug can be administered sequentially or simultaneously. If Form 1 and/or Form 2 of squalamine phosphate or a conventional antiviral drug are administered sequentially, either squalamine or the conventional antiviral drug can be administered first.

In contrast to traditional antiviral therapies, viruses are not expected to develop resistance to squalamine. This is because unlike conventional antiviral therapies, squalamine does not act upon a single mechanism by which a virus infects a cell. Rather, squalamine changes the cell structure for a period of time during which the virus cannot infect the cell. In contrast, certain anti-HIV drugs target the CD4 receptor and other antiviral drugs target inhibition of replication. Viral variants can circumvent each of these targeted antiviral therapies. In one embodiment of the present technology, squalamine does not demonstrate an altered $IC_{50}$ or $IC_{90}$ (drug concentration required to inhibit viral growth by 50% or 90% respectively) over time. In other embodiments of the present technology, squalamine demonstrates an $IC_{50}$ or $IC_{90}$ which does not increase by more than 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, or 30% over time. In other embodiments of the present technology, the time period over which the change in $IC_{50}$ or $IC_{90}$ (or lack thereof) is measured is 1 week, 2 weeks, 3 weeks, 4 weeks, 1 month, 1.5 months, 2 months, 2.5 months, 3 months, 3.5 months, 4 months, 4.5 months, 5 months, 5.5 months, 6 months, 6.5 months, 7 months, 7.5 months, 8 months, 8.5 months, 9 months, 9.5 months, 10 months, 10.5 months, 11 months, 11.5 months, 12 months, 1 year, 1.5 years, 2 years, 2.5 years, 3 years, 3.5 years, 4 years, 4.5 years, or 5 years.

Toxicity: Conventional antiviral agents are generally designed to target viral specific enzymes, such as RNA and DNA polymerases, proteases, or glycosidases; and as a consequence the drug inhibits the activity of the viral enzyme to a far greater extent than it does to analogous human enzymes, required for normal cellular functioning. In many instances toxicity develops as a consequence of the residual activity of the agent towards the analogous enzymes of the host. The experience collected to date involving the administration of squalamine to humans suggests that the compound has an acceptable therapeutic index, a property that further enhances the utility of the present technology disclosed herein.

B. Microbial Infections

The present technology is directed to methods of treating and/or preventing microbial infections, and in particular pathogenic microorganisms, comprising administering a therapeutically effective amount of a squalamine phosphate composition described herein to a subject in need. As noted above, this method encompasses using a squalamine phosphate composition described herein in combination with conventional antimicrobial treatments to treat and/or prevent infections. A "subject in need" is a human or animal at risk of a microbial infection, or which has contracted a microbial infection.

As used herein the term "microorganism" refers to microscopic organisms and taxonomically related macroscopic organisms within the categories of algae, bacteria, fungi (including lichens), protozoa, viruses, and subviral agents. The term microorganism encompasses both those organisms that are in and of themselves pathogenic to another organism (e.g., animals, including humans, and plants) and those organisms that produce agents that are pathogenic to another organism, while the organism itself is not directly pathogenic or infective to the other organism. As used herein the term "pathogen," and grammatical equivalents, refers to an organism, including microorganisms, that causes disease in another organism (e.g., animals and plants) by directly infecting the other organism, or by producing agents that causes disease in another organism (e.g., bacteria that produce pathogenic toxins and the like).

1. Bacterial Infection

The bacterial infection to be treated and/or prevented can be due to a gram negative bacteria, gram positive bacteria, Mycobacteria, bacterial spore, or any combination thereof. Pathogenic bacteria are a major cause of human death and disease and cause infections such as tetanus, typhoid fever, diphtheria, syphilis, cholera, foodborne illness, leprosy and tuberculosis. Examples of gram positive bacteria include, but are not limited to genera such as *Staphylococcus, Streptococcus, Enterococcus,* (which are cocci) and *Bacillus, Corynebacterium, Nocardia, Clostridium, Actinobacteria,* and *Listeria*. Examples of gram negative bacteria include, but are not limited to, *Escherichia coli, Salmonella, Shigella, Enterobacteriaceae, Neisseria, Pseudomonas, Moraxella, Helicobacter, Stenotrophomonas, Bdellovibrio,* acetic acid bacteria, *Legionella* and alpha-proteobacteria as Wolbachia and many others. Other notable groups of Gram-negative bacteria include the cyanobacteria, spirochaetes, green sulfur and green non-sulfur bacteria. Medically relevant Gram-negative bacilli include a multitude of species. Some of them primarily cause respiratory problems (*Hemophilus influenzae, Klebsiella pneumoniae, Legionella pneumophila, Pseudomonas aeruginosa*), primarily urinary problems (*Escherichia coli, Proteus mirabilis, Enterobacter cloacae, Serratia marcescens*), and primarily gastrointestinal problems (*Helicobacter pylori, Salmonella enteritidis, Salmonella typhi*). Gram-negative bacteria associated with nosocomial infections include *Acinetobacter baumannii,* which cause bacteremia, secondary meningitis, and ventilator-associated pneumonia in intensive care units of hospital establishments. Relevant Mycobacteria include M tuberculosis complex (MTBC), *M. tuberculosis, M. bovis, M. africanum,* and *M. microti; M. leprae, M. avium* complex, *M. avium paratuberculosis, M. avium sylvaticum,* or any of the Mycobacterial species demonstrated to cause disease in man and/or animals.

2. Fungal Infections

The fungal, yeast and/or mold infection to be treated, prevented, and/or cured may be a tinea infection, dermatophytoses, or a dermatophytoma. Examples of fungal microorganisms include, but are not limited to, *Trichophyton* spp., *Epidermophyton* spp., *Fusarium* spp., *Aspergillus* spp., *Paecilomyces* spp., *Acremonium* spp., *Scytalydium* spp., *Scopulariopsis* spp., *Scedosporium* spp., *Alternaria* spp., *Epicoccum* spp., *Curvularia* spp., *Candida* spp., *Phoma* spp., *Chaetomium* spp., and *Microsporum* spp.

Molds include, but are not limited to infections caused by the fungi *Acremonium* spp., *Aspergillus* spp. (e.g., *A. sydowii, A. terreus, A. niger*), *Fusarium* spp. (e.g., *F. oxysporum, F. solani, F. semitectum*), *Scopulariopsis* spp. (e.g., *Scopulariopsis brevicaulis*), *Scedosporuim* spp., *Alternaria* spp., *Paecilomyces lilacinus, Epiccocum nigrum, Phoma* spp. *Chaetomium* spp., *Curvularia* spp., *Onychocola canadensis,* and *Scytalidium* spp., (e.g., *S. dimidiatum*).

Yeast, as defined herein, include, but are not limited to, Candida species causing yeast infections.

C. Cancer

The present technology is directed to methods of treating malignant and cancerous tumors, comprising administering a therapeutically effective amount of a squalamine phosphate composition described herein to a subject in need. A "subject in need" is a human or animal having a malignant and cancerous tumor. As noted above, this method encompasses using a squalamine phosphate composition described herein in combination with conventional cancer treatments to treat tumors.

Examples of tumors that can be treated with the compositions of the present technology include, but are not limited to, breast, brain, lung (e.g., non-small cell lung cancer), and CNS. An example of a solid brain tumor that can be treated with a composition according to the present technology is a malignant glioma. Other examples of cancers that can be treated with compositions according to the present technology include, but are not limited to, prostate cancer.

D. Neurological Disorders

The invention also encompasses use of the pharmaceutical compositions of the invention in methods of treatment of neurological disorders, such as Parkinson's disease, autism, multiple system atrophy, depression, Alzheimer's disease, Huntington's Disease, schizophrenia, multiple sclerosis, and degenerative processes associated with aging, autonomic system instability, including delays in sleep onset, fragmentation of sleep, reduced REM sleep, reduced total sleep time, REM-behavior disorder, sleep breathing disorder including snoring and sleep apnea, hallucinations, narcolepsy, and day-time sleepiness.

E. Gastrointestinal Disorders

The invention also encompasses use of the pharmaceutical compositions of the invention in methods of treatment of gastronintestinal disorders such as constipation, Crohn's disease or IBS. Thus, any active agent known to be useful in treating these conditions can be used in the disclosed, and either combined with the aminosterol compositions used in the methods, or administered separately or sequentially.

IV. Methods of Preparing Form 1 or Form 2

In another aspect, provided herein are processes to prepare the squalamine phosphate solid form of Form 1 or Form 2.

In some embodiments, provided herein is a process for preparing the squalamine phosphate solid form of Form 1, the process comprising: (a) combining a solution of squalamine lactate with an aqueous solution of sodium phosphate dibasic and sodium phosphate monobasic to form a combined mixture; (b) heating the combined mixture before allowing the combined mixture to cool; and (c) isolating the combined mixture to isolate the squalamine phosphate solid form.

As used herein, "squalamine lactate" refers to any lactate salt of squalamine. In some embodiments, squalamine lactate refers to squalamine monolactate. In some embodiments, squalamine lactate refers to squalamine dilactate.

As used herein, "squalamine phosphate" refers to any phosphate salt of squalamine. In some embodiments, squalamine phosphate refers to squalamine monophosphate. In some embodiments, squalamine phosphate refers to squalamine bis-phosphate. In some embodiments, squalamine phosphate refers to a hydrated phosphate salt of squalamine.

In some embodiments, the combining step is performed at a temperature of about 55° C. to about 70° C. This includes a temperature of about 55° C. to about 65° C., about 55° C. to about 60° C., about 60° C. to about 70° C., about 60° C. to about 65° C., or about 65° C. to about 70° C. In some embodiments, the temperature is about 55, about 56, about 57, about 58, about 59, about 60, about 61, about 62, about 63, about 64, about 65, about 66, about 67, about 68, about 69, or about 70° C., including increments therein. In some embodiments, the combining step is performed at 60±5° C.

In some embodiments, the solution of squalamine lactate is a methanol solution of squalamine lactate.

In some embodiments, the heating step is performed at a temperature of about 65° C. to about 75° C. This includes a temperature of about 65, about 66, about 67, about 68, about 69, about 70, about 71, about 72, about 73, about 74, or about 75° C., including increments therein. In some embodiments, the heating step is performed at a temperature of about 65° C. to about 70° C., or about 70° C. to about 75° C. In some embodiments, the heating step is performed at 70±5° C. In some embodiments, the heating step is performed at a temperature above the temperature attained during the combining step.

In some embodiments, the process further comprises stirring the combined mixture after cooling but before the isolating step.

In some embodiments, the isolating step comprises filtering the combined mixture and washing filtered solids with a solvent. In some embodiments, the isolating step comprises filtering the combined mixture and washing filtered solids with acetone. In some embodiments, the isolating step comprises filtering the combined mixture and washing filtered solids with acetone, water, ethanol, methanol, methyl ethyl ketone, or any combination thereof.

In some embodiments, provided herein is a process for preparing the squalamine phosphate solid form of Form 2, the process comprising: (a) dissolving squalamine lactate in base, water, and alcohol to form a first solution; (b) heating the first solution to a first elevated temperature, wherein the first elevated temperature is greater than 25° C.; (c) adding a first amount of phosphoric acid ($H_3PO_4$) to the first solution to form a second solution; (d) heating the second solution to a second elevated temperature higher than the first elevated temperature; (e) adding a second amount of $H_3PO_4$ to the second solution; (f) obtaining a slurry; and (h) isolating the squalamine phosphate solid form.

In some embodiments, the base is sodium hydroxide. In some embodiments, the base is potassium hydroxide. In some embodiments, the base is lithium hydroxide.

In some embodiments, the alcohol is ethanol. In some embodiments, the alcohol is methanol. In some embodiments, the alcohol is propanol. In some embodiments, the alcohol is ethanol, methanol, propanol, or any combination thereof.

In some embodiments, the first elevated temperature is at least about 35° C. This includes a first elevated temperature of at least about 36, about 37, about 38, about 39, about 40, about 41, about 42, about 43, about 44, about 45, about 46, about 47, about 48, about 49, about 50, about 51, about 52, about 53, about 54, or about 55° C., including increments therein. In some embodiments, the first elevated temperature is about 35, about 36, about 37, about 38, about 39, about 40, about 41, about 42, about 43, about 44, about 45, about 46, about 47, about 48, about 49, about 50, about 51, about 52, about 53, about 54, or about 55° C., including increments therein. In some embodiments, the first elevated temperature is about 35° C. to about 55° C. This includes the temperature range of about 35° C. to about 50° C., about 35° C. to about 45° C., about 35° C. to about 40° C., about 40° C. to about 55° C., about 40° C. to about 50° C., about 40° C. to about 45° C., about 45° C. to about 55° C., about 45° C. to about 50° C., or about 50° C. to about 55° C.

In some embodiments, the second elevated temperature is at least about 45° C. This includes a second elevated temperature of at least about 46, about 47, about 48, about 49, about 50, about 51, about 52, about 53, about 54, or about 55° C., including increments therein. In some embodiments, the second elevated temperature is about 45, about 46, about 47, about 48, about 49, about 50, about 51, about 52, about 53, about 54, or about 55° C., including increments therein. In some embodiments, the second elevated temperature is about 45° C. to about 55° C. This includes the temperature range of about 45° C. to about 50° C., or about 50° C. to about 55° C.

In some embodiments, the step of obtaining the slurry comprises seeding the mixture. In some embodiments, a previous batch of squalamine phosphate is used to seed the mixture, preferably of the same form that is being prepared.

In some embodiments, the step of obtaining the slurry comprises adding a third amount of $H_3PO_4$ to the second solution.

In some embodiments, the step of obtaining the slurry comprises cooling the second solution. In some embodiments, the step of obtaining the slurry comprises cooling the second solution to room temperature.

In some embodiments, the process further comprises aging the slurry prior to the isolating step. In some embodiments, the step of aging the slurry is performed for at least about 8, about 9, about 10, about 11, about 12, about 13, about 14, about 15, or about 16 hours. In some embodiments, the step of aging the slurry is performed for about 8, about 9, about 10, about 11, about 12, about 13, about 14, about 15, or about 16 hours.

In some embodiments, the isolating step comprises filtering the slurry and washing filtered solids with a solvent. In some embodiments, the isolating step comprises filtering the slurry and washing filtered solids with acetone. In some embodiments, the isolating step comprises filtering the slurry and washing filtered solids with acetone. In some embodiments, the isolating step comprises filtering the slurry and washing filtered solids with acetone, water, ethanol, methanol, methyl ethyl ketone, or any combination thereof.

In some embodiments, provided herein is a process for preparing the squalamine phosphate solid form of Form 2, the process comprising: (a) combining squalamine free base in water and alcohol to form a first solution; (b) adding phosphoric acid ($H_3PO_4$) to the first solution to obtain a first slurry; (c) aging the first slurry; (d) isolating solids from the first slurry; (e) mixing the solids in water and alcohol to form a second slurry; (f) heating the second slurry; (g) cooling the second slurry; (h) repeating steps (f) and (g); and (i) isolating the squalamine phosphate solid form of Form 2.

In some embodiments, the alcohol of step (a) is ethanol. In some embodiments, the water and alcohol of step (a) is 90:10 v/v ethanol:water. In some embodiments, the water and alcohol of step (a) is from 90:10 v/v ethanol:water to 50:50 v/v ethanol:water. This includes 85:15 v/v ethanol:

water, 80:20 v/v ethanol:water, 75:25 v/v ethanol:water, 70:30 v/v ethanol:water, 65:35 v/v ethanol:water, 60:40 v/v ethanol:water, 55:45 v/v ethanol:water, and 50:50 v/v ethanol:water, including increments therein.

In some embodiments, step (a) further comprises heating to form the first solution. In further embodiments, step (a) further comprises heating to 40° C. to form the first solution.

In some embodiments, step (b) is performed at a lower temperature than step (a). In some embodiments, the lower temperature is about 35° C. In some embodiments, phosphoric acid is added batch-wise to the first solution. In some embodiments, step (b) further comprises seeding the first solution. In some embodiments, a previous batch of squalamine phosphate is used to seed the first solution, preferably of the same form that is being prepared.

In some embodiments, step (c) is performed at the same temperature as step (b). In some embodiments, step (c) is performed at the same temperature as step (b) for at least about 4 hours and then at a lower temperature for at least about 8 hours. In some embodiments, step (c) is performed at the same temperature as step (b) for about 6 hours and then at a lower temperature for about 10 hours. In some embodiments, the lower temperature is less than about 35° C. In still further embodiments, the lower temperature is about 20° C.

In some embodiments, step (d) comprises filtering the first slurry and washing filtered solids with a solvent. In some embodiments, step (d) comprises filtering the first slurry and washing filtered solids with acetone.

In some embodiments, the alcohol of step (e) is ethanol. In some embodiments, the water and alcohol of step (e) is 67:33 v/v ethanol/water.

In some embodiments, the heating in step (f) is performed at a temperature of at least about 40° C. In some embodiments, the temperature is about 41, about 42, about 43, about 44, about 45, about 46, about 47, about 48, about 49, about 50, about 51, about 52, about 53, about 54, or about 55° C.

In some embodiments, the second slurry is cooled to a temperature below about 40° C. in step (g). In some embodiments, the temperature is about 20, about 21, about 22, about 23, about 24, about 25, about 26, about 27, about 28, about 29, about 30, about 31, about 32, about 33, about 34, about 35, about 36, about 37, about 38, or about 39° C.

In some embodiments, steps (f) and (g) are repeated at least about 2, about 3, about 4, about 5, or about 6 times. In some embodiments, steps (f) and (g) are repeated about 2, about 3, about 4, about 5, or about 6 times.

In some embodiments, step (i) comprises filtering the second slurry and washing filtered solids with a solvent. In some embodiments, step (i) comprises filtering the second slurry and washing filtered solids with acetone.

In some embodiments of the methods disclosed herein, squalamine lactate is replaced with another salt of squalamine, wherein the other salt of squalamine is not squalamine phosphate. In some embodiments, squalamine lactate is converted to another salt of squalamine, wherein the other salt of squalamine is not squalamine phosphate, prior to conversion to squalamine phosphate.

V. Definitions

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term, for example, ±1%, ±2%, ±3%, ±4%, ±5%, ±6%, ±7%, ±8%, ±9% or ±10%. As used herein in the context of values of degrees 2-theta (2θ), "about" refers to ±0.2° in some embodiments, or in some embodiments, ±0.1°. As used herein in the context of the temperature(s) of endothermic peak(s) within a differential scanning calorimetry thermogram, "about" refers to ±0.4° C.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

The term "substantially" generally refers to at least 90% similarity. In some embodiments, in the context of a first X-ray powder diffraction pattern being substantially as shown in a second X-ray powder diffraction pattern, "substantially" refers to ±0.2°. In some embodiments, in the context of a first differential scanning calorimetry thermogram being substantially as shown in a second differential scanning calorimetry thermogram, "substantially" refers to ±0.4° C. In some embodiments, in the context of a first thermogravimetric analysis being substantially as shown in a second thermogravimetric analysis, "substantially" refers to ±0.4% weight. In some embodiments, "substantially purified" refers to at least 95% purity. This includes at least 96, 97, 98, or 99% purity. In further embodiments, "substantially purified" refers to about 95, 96, 97, 98, 99, 99.5, or 99.9% purity, including increments therein.

As used herein, "therapeutic activity" or "activity" may refer to an activity whose effect is consistent with a desirable therapeutic outcome in humans, or to desired effects in non-human mammals or in other species or organisms. Therapeutic activity may be measured in vivo or in vitro. For example, a desirable effect may be assayed in cell culture.

As used herein, the phrase "therapeutically effective amount" shall mean the drug dosage that provides the specific pharmacological response for which the drug is administered in a significant number of subjects in need of such treatment. It is emphasized that a therapeutically effective amount of a drug that is administered to a particular subject in a particular instance will not always be effective in treating the conditions/diseases described herein, even though such dosage is deemed to be a therapeutically effective amount by those of skill in the art.

The present technology, thus generally described, will be understood more readily by reference to the following examples, which are provided by way of illustration and are not intended to be limiting of the present technology.

EXAMPLES

Example 1

Preparation of Crude Squalamine

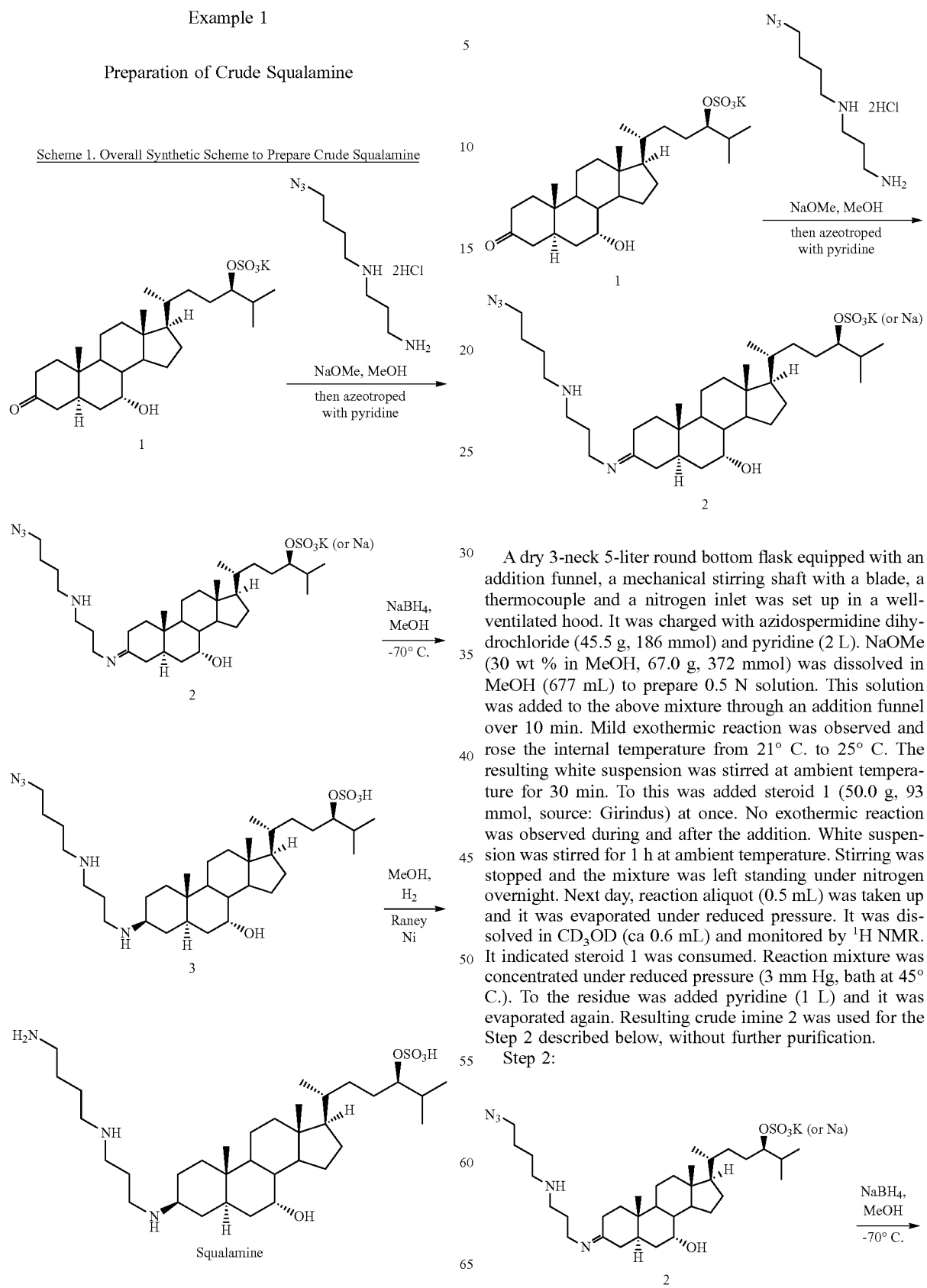

Scheme 1. Overall Synthetic Scheme to Prepare Crude Squalamine

Step 1:

A dry 3-neck 5-liter round bottom flask equipped with an addition funnel, a mechanical stirring shaft with a blade, a thermocouple and a nitrogen inlet was set up in a well-ventilated hood. It was charged with azidospermidine dihydrochloride (45.5 g, 186 mmol) and pyridine (2 L). NaOMe (30 wt % in MeOH, 67.0 g, 372 mmol) was dissolved in MeOH (677 mL) to prepare 0.5 N solution. This solution was added to the above mixture through an addition funnel over 10 min. Mild exothermic reaction was observed and rose the internal temperature from 21° C. to 25° C. The resulting white suspension was stirred at ambient temperature for 30 min. To this was added steroid 1 (50.0 g, 93 mmol, source: Girindus) at once. No exothermic reaction was observed during and after the addition. White suspension was stirred for 1 h at ambient temperature. Stirring was stopped and the mixture was left standing under nitrogen overnight. Next day, reaction aliquot (0.5 mL) was taken up and it was evaporated under reduced pressure. It was dissolved in $CD_3OD$ (ca 0.6 mL) and monitored by $^1H$ NMR. It indicated steroid 1 was consumed. Reaction mixture was concentrated under reduced pressure (3 mm Hg, bath at 45° C.). To the residue was added pyridine (1 L) and it was evaporated again. Resulting crude imine 2 was used for the Step 2 described below, without further purification.

Step 2:

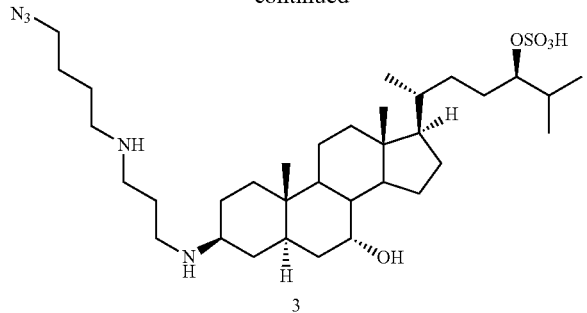

Above crude imine 2 was dissolved in MeOH (2 L) and it was cooled to −70° C. with dry ice-acetone bath under nitrogen atmosphere. While stirring with mechanical stir, NaBH$_4$ (10.6 g, 279 mmol) was added in 2 portions. After the addition, the mixture was stirred for 1 h at −70° C. At this point, the reaction was monitored by HPLC and it indicated 2 was consumed and gave azide 3 in 81:19 (β:α) selectivity at 3-position. The mixture was left stirred overnight at ambient temperature. Next day, distilled water (250 mL) was added to the mixture and the resulting clear solution was concentrated under reduced pressure (10 mm Hg, bath at 45° C.). The residue was partitioned in sec-BuOH (1.2 L) and distilled water (250 mL), and the layers were separated. The organic layer washed with distilled water (400 mL) but the layer did not separate well. Thus, MTBE (400 mL) was added to aid the separation. Organic layer was separated and it was concentrated under reduced pressure (bath at 45° C.). Resulting crude azide 3 was used for the Step 3 described below, without further purification.

Step 3:

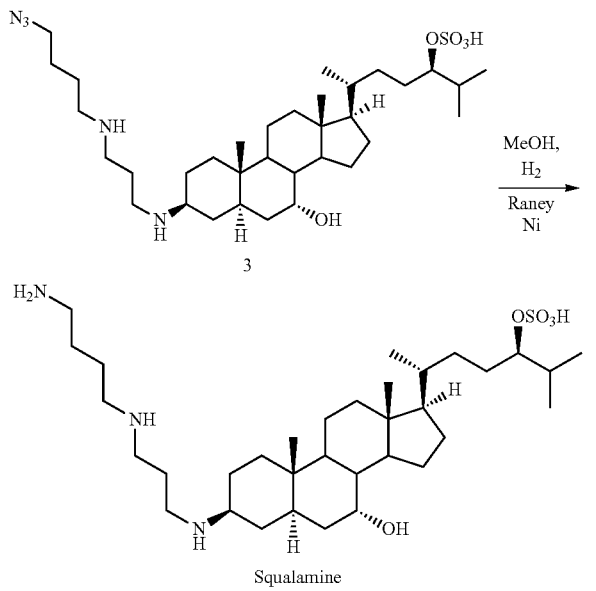

Above crude azide 3 was dissolved in MeOH (530 mL) and it was transferred to the pressure bottle. To this was added Raney Nickel (18.4 g) and the mixture was stirred under 50 psi hydrogen pressure at ambient temperature overnight. The next day, HPLC analysis indicated that azide 3 was consumed. The mixture was filtered through a pad of filter agent (AW Standard SUPERCEL® NF (Aldrich, 221791) and the filter cake was rinsed with MeOH (300 mL). Filtrate (ca 1 L) was concentrated to the volume of ca 500 mL. To this was added sec-BuOH (1 L) and the resulting clear solution was concentrated under reduced pressure to the volume of ca 500 mL. To the resulting cloudy viscous solution was added MTBE (1.25 L) and the resulting white suspension was stored in the cold room (5° C.) overnight. Next day, suspension was filtered and the filter cake was rinsed with MTBE (200 mL). Filter cake was dried in the vacuum oven at 40° C. for 6 h. Crude squalamine (57.3 g) as a white solids was obtained in a mixture of two diastereomers (86:14, 3(3:3a), contaminated with excess spermidine.

Example 2

Preparation of Squalamine Phosphate from Crude Squalamine

Preparation via Direct Crystallization (Form 2)

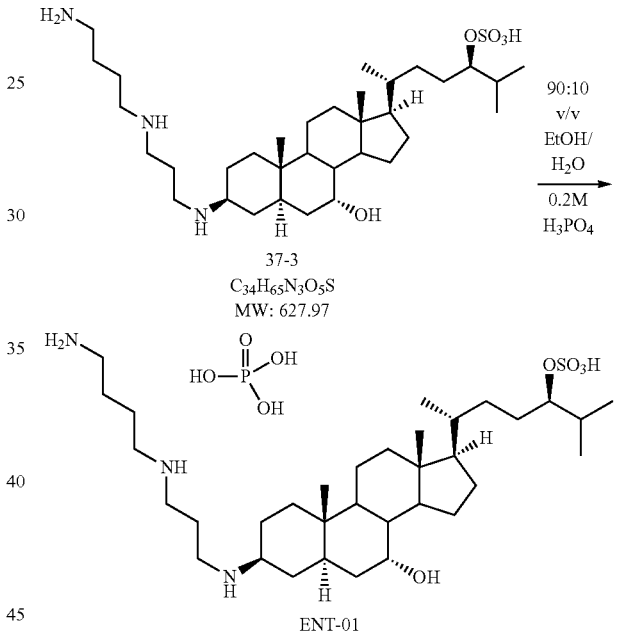

Initial Preparation 2 g of crude squalamine (Example 1) was mixed with 90:10 v/v EtOH/water (40 mL) in 100 mL EasyMax vessel with a baffle (overhead stirring at 450 rpm). The slurry was heated at 40° C. for 10 min giving a clear colorless solution. The solution was cooled to 35° C., and 0.2 M H$_3$PO$_4$ (22 mL, 1.4 equiv) was added by syringe pump over 1.5 h. The batch turned a bit hazy after 0.5 mL of 0.2 M H$_3$PO$_4$ (0.02 eq) and seed (5 mg, semi-crystalline squalamine phosphate, most closely resembling Form 2) were added. Some sticky solids formed on the surface of baffle and bottom of vessel. After 1.0 equiv of 0.2 M H$_3$PO$_4$ was added, the batch became significantly cloudy, and eventually turned into a nice free flowing white slurry after all 1.4 equiv 0.2 M H$_3$PO$_4$ was added. The slurry mixture was aged at 35° C. for 6 h, cooled to 20° C. over 2 h, aged at the same temperature for 10 h. The product was isolated by filtration. The wet cake was washed with acetone (2×15 mL). 2.24 g of squalamine phosphate solids was obtained after isolation and vacuum oven drying.

Figure 1:
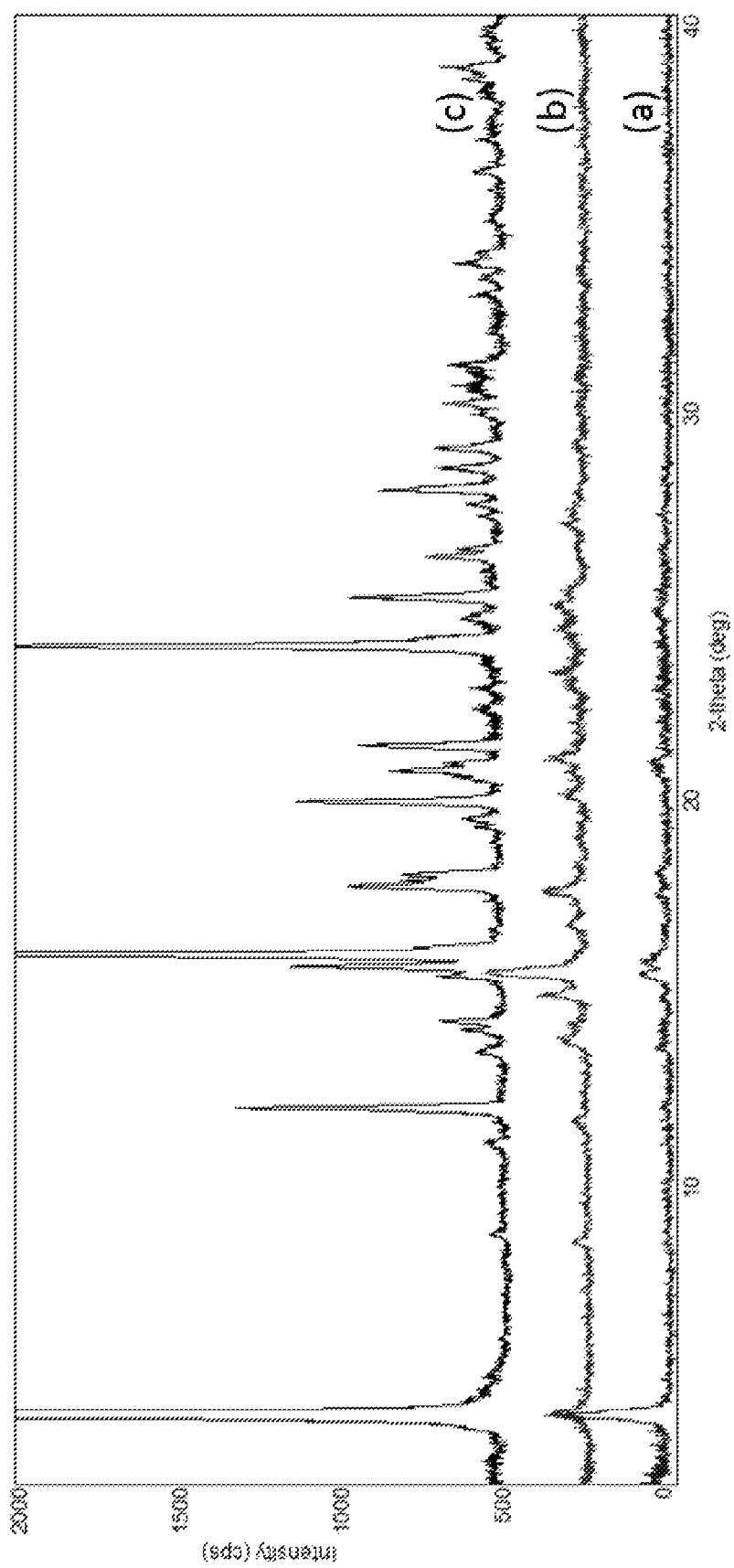
FIG. 1 shows X-ray powder diffraction (XRPD) patterns of squalamine phosphate samples of (a) dry product of initial preparation (Example 2), (b) final wet cake of initial preparation (Example 2), and (c) Form 1 (from Example 5).

X-ray powder diffraction (XRPD) patterns of the isolated product are shown in FIG. 1 (XRPD patterns (b) and (a) as wet and dry cakes, respectively), indicating Form 2. It is different from the XRPD pattern of Form 1.

Crystallinity Upgrade of Form 2

0.5 g of crude squalamine phosphate-Form 2 (from initial preparation) was mixed with 24 mL of 67:33 v/v EtOH/water. The resulting slurry mixture was treated with heating-cooling cycle: (a) 55° C. (for 30 min) cooled to 20° C. over 10 h; (b) hold at 20° C. for 2 h; (c) heat back to 55° C. over 30 min; (d) repeat above for 6 times; (e) hold at 20° C. for 10-20 h.

Figure 2:
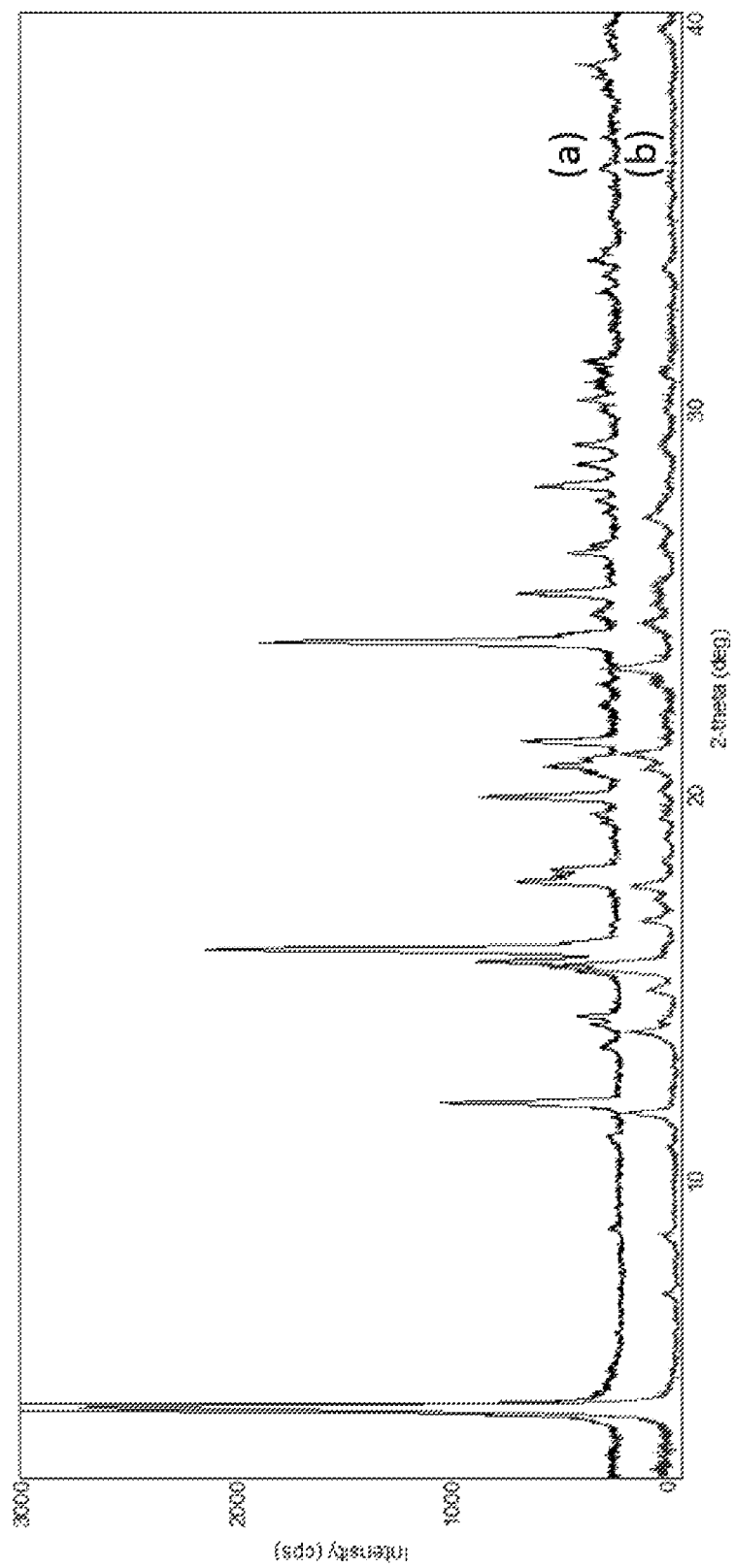
FIG. 2 shows XRPD patterns of squalamine phosphate samples of (a) Form 1 (from Example 5), and (b) end solids from crystallinity upgrade (Form 2, Example 2).

The isolated solids as wet cake gave XRPD pattern of Form 2 (see FIG. 2, XRPD pattern (b)). Select peaks from the XRPD pattern are shown in Table 1.

TABLE 1

Select peaks from XRPD pattern of squalamine phosphate (Form 2)

| No. | 2-theta (degrees) | Rel. intensity | Rel. height |
|---|---|---|---|
| 1 | 3.8 | 100 | 100 |
| 2 | 6.7 | 2.22 | 2.94 |
| 3 | 8.2 | 2.15 | 2.84 |
| 4 | 11.4 | 8.14 | 8.25 |
| 5 | 13.5 | 9.16 | 5.27 |
| 6 | 14.6 | 4.33 | 3.76 |
| 7 | 15.2 | 26.56 | 21.05 |
| 8 | 16.4 | 3.81 | 4.29 |
| 9 | 17.3 | 9.45 | 6.13 |
| 10 | 20.3 | 2.63 | 4.85 |
| 11 | 20.8 | 10.7 | 8.22 |
| 12 | 22.5 | 3.09 | 2.02 |
| 13 | 22.9 | 8.88 | 9.08 |
| 14 | 25.0 | 14.09 | 1.98 |
| 15 | 26.1 | 2 | 1.24 |
| 16 | 26.8 | 7.15 | 3.14 |

Figure 3:
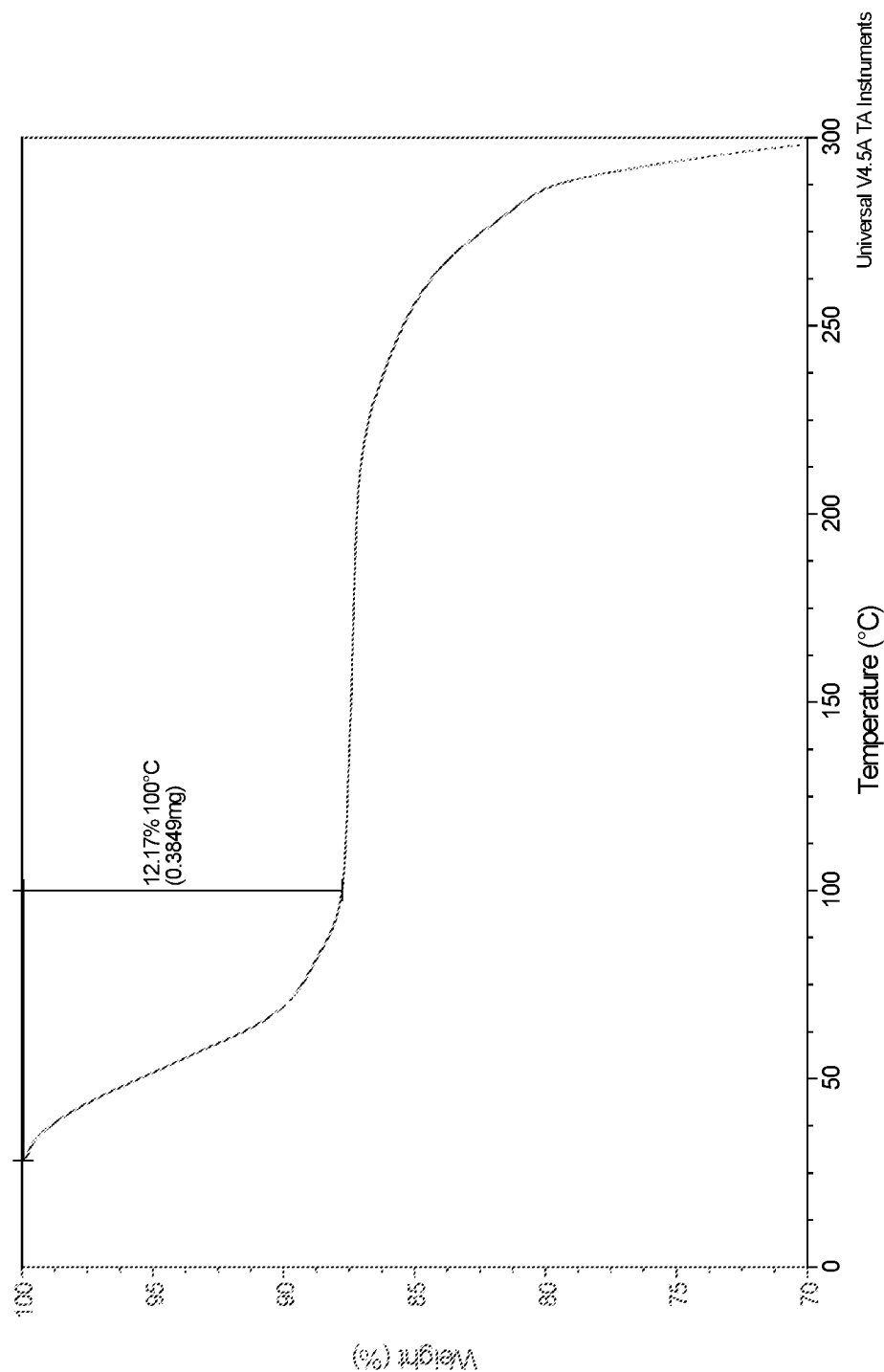
FIG. 3 shows results from thermogravimetric analysis (TGA) of squalamine phosphate, Form 2 (from Example 2).
Figure 4:
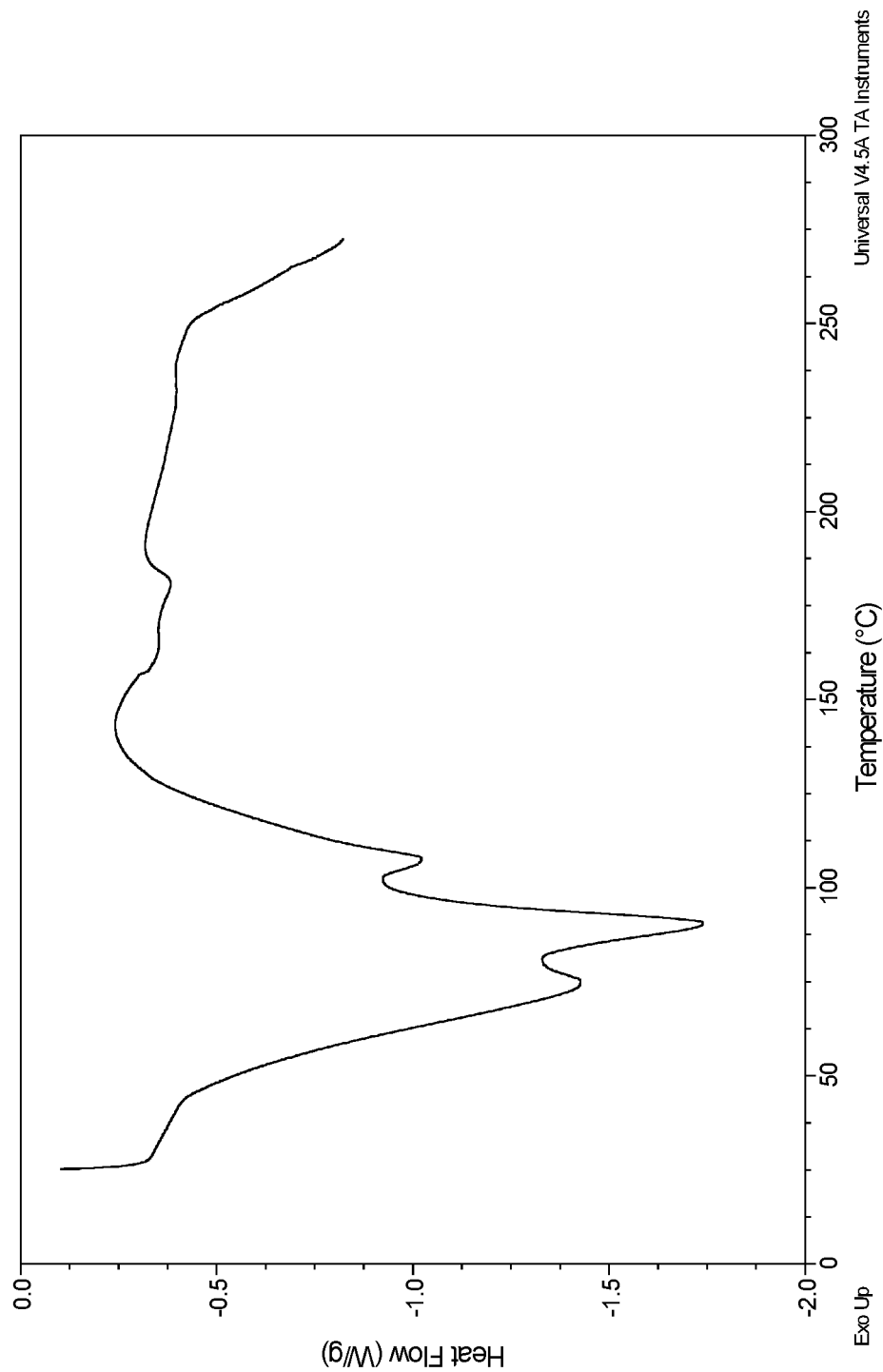
FIG. 4 shows results from differential scanning calorimetry (DSC) of squalamine phosphate, Form 2 (from Example 2).

Results from thermogravimetric analysis (TGA) and differential scanning calorimetry (DSC) of the dried sample are shown in FIG. 3 and FIG. 4, respectively.

Example 3

Preparation of Squalamine Lactate from Crude Squalamine

Squalamine lactate crystals were prepared from the crude Squalamine described in Example 1 via the literature procedure prior to conversion to the lactate salt.

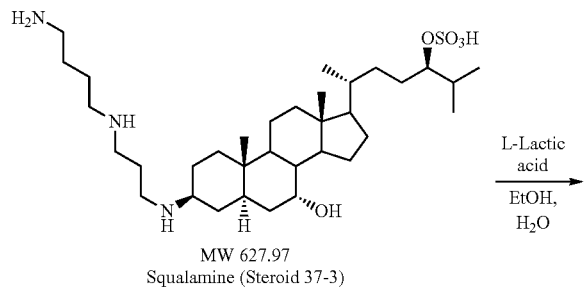

MW 627.97
Squalamine (Steroid 37-3)

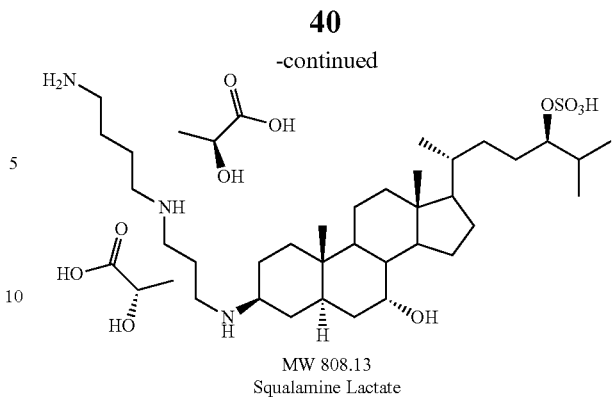

MW 808.13
Squalamine Lactate

A. Polish Filtration

Crude Squalamine (2.37 g, Example 1) was mixed with EtOH (40 mL, anhydrous, 200 proof) in a 100 mL flask with a magnetic stir bar. The mixture was stirred at RT for 10 min to get an opaque solution. The solution was polish filtered through 0.45 micron PTFE syringe filter to give a clear solution.

B. Crystallization

The clear solution was transferred to 100 mL EasyMax vessel and rinsed with EtOH (5 mL). The resulting mixture was stirred (300 rpm, with a baffle) at 20° C. In a separate 6 mL vial, water (1.9 mL) was mixed with L-lactic acid (1.36 g, 4 equiv) to get a clear solution. 1.5 equiv of L-lactic acid (1.0 mL) was added to the batch over 1 min at 20° C. Seed (5 mg, a previous batch of squalamine lactate), 99.6:0.4 ratio of 313:3a) was added, no batch cloudiness observed and most seed dissolved. Additional 0.7 equiv L-lactic acid (0.5 mL) added, Seed (5 mg, a previous batch of squalamine lactate) was added, no batch cloudiness observed and most seed dissolved. The batch temperature was decreased from 20° C. to 15° C. Additional 0.7 equiv L-lactic acid (0.5 mL) added, seed (5 mg, a previous batch of squalamine lactate) was added. The batch slowly turned hazy after seeding. The rest of L-lactic acid aqueous solution (0.73 mL) was added over 10 min at 15° C. Aliquot sample was isolated by filtration, the wet cake was sampled and analyzed by polarized light microscopy (PLM), XRPD, and HPLC (data not shown).

The batch was isolated by filtration, the wet cake was washed by EtOH (2×15 mL), dried in a vacuum oven (40° C.) with nitrogen sweep for 2 days. 1.602 g of squalamine lactate as white solid was obtained.

Example 4

Preparation of Squalamine Phosphate (Form 2) from Squalamine Lactate

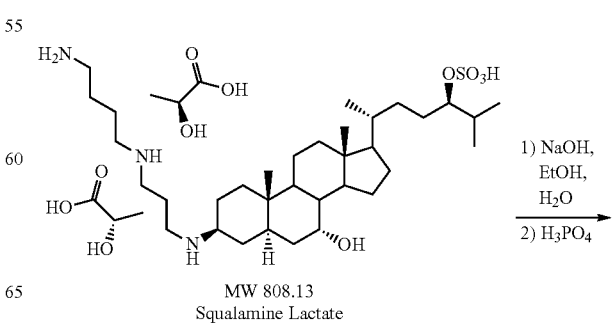

MW 808.13
Squalamine Lactate

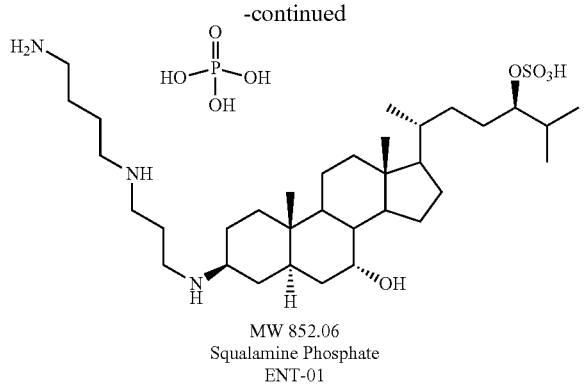

MW 852.06
Squalamine Phosphate
ENT-01

Figure 5:
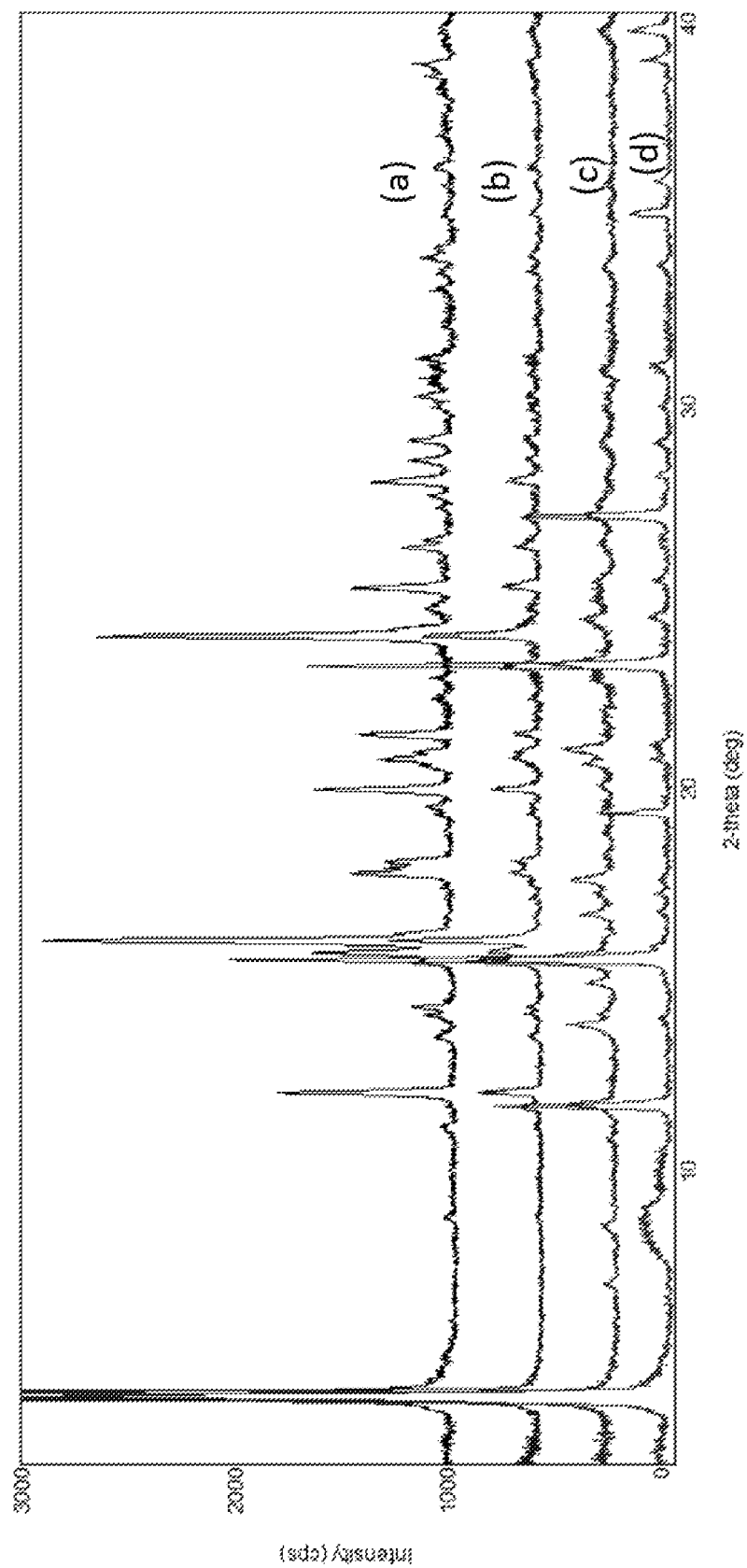
FIG. 5 shows XRPD patterns of squalamine phosphate samples of (a) Form 1 from Example 5, (b) Form 1 material (from Example 5) used as seed in Example 4, (c) Form 2 from Example 2 (after crystallinity upgrade), (d) wet cake (Form 2) of Example 4.
Figure 6:
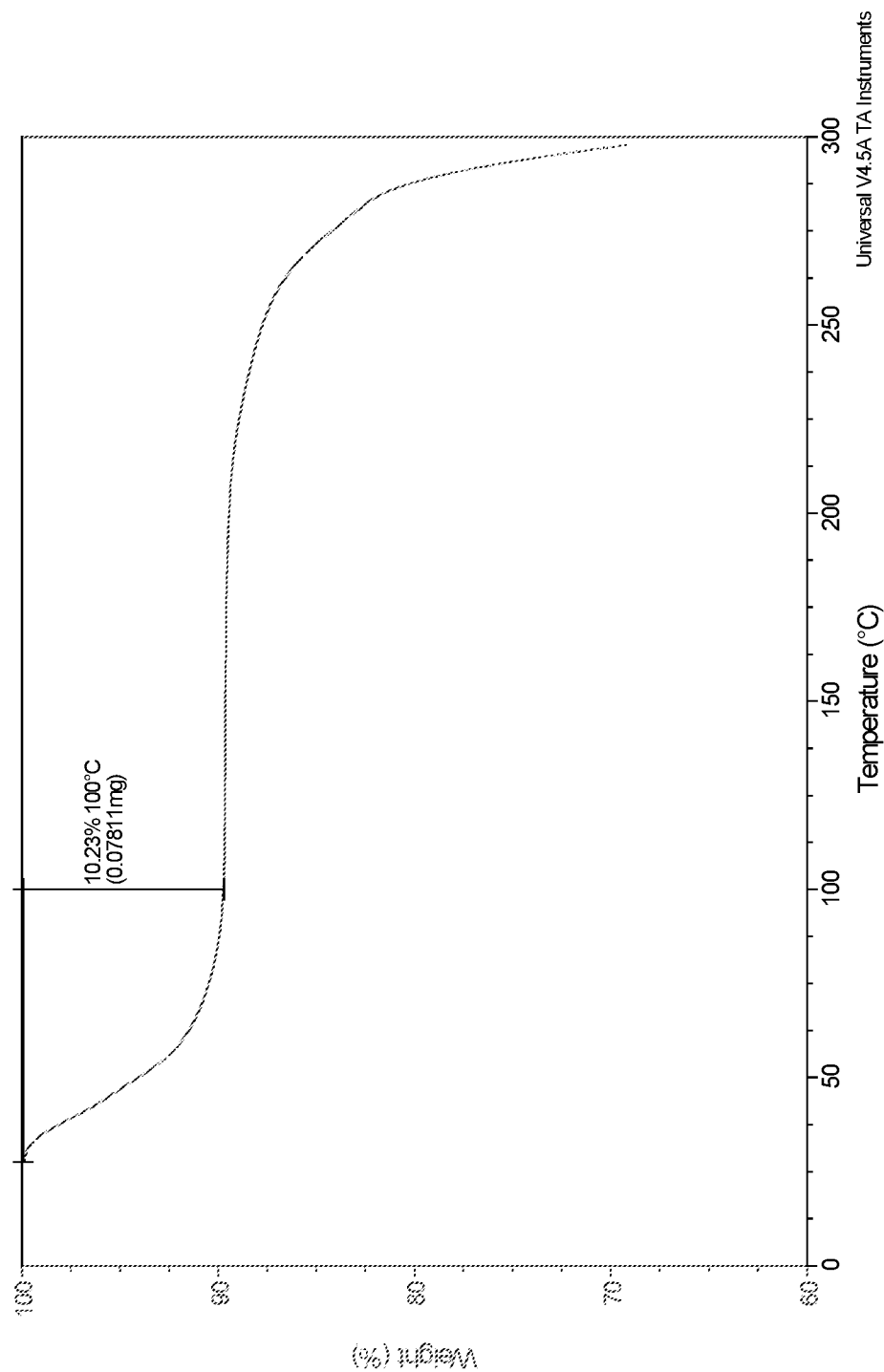
FIG. 6 shows results from TGA of squalamine phosphate, Form 2 (from Example 4).
Figure 7:
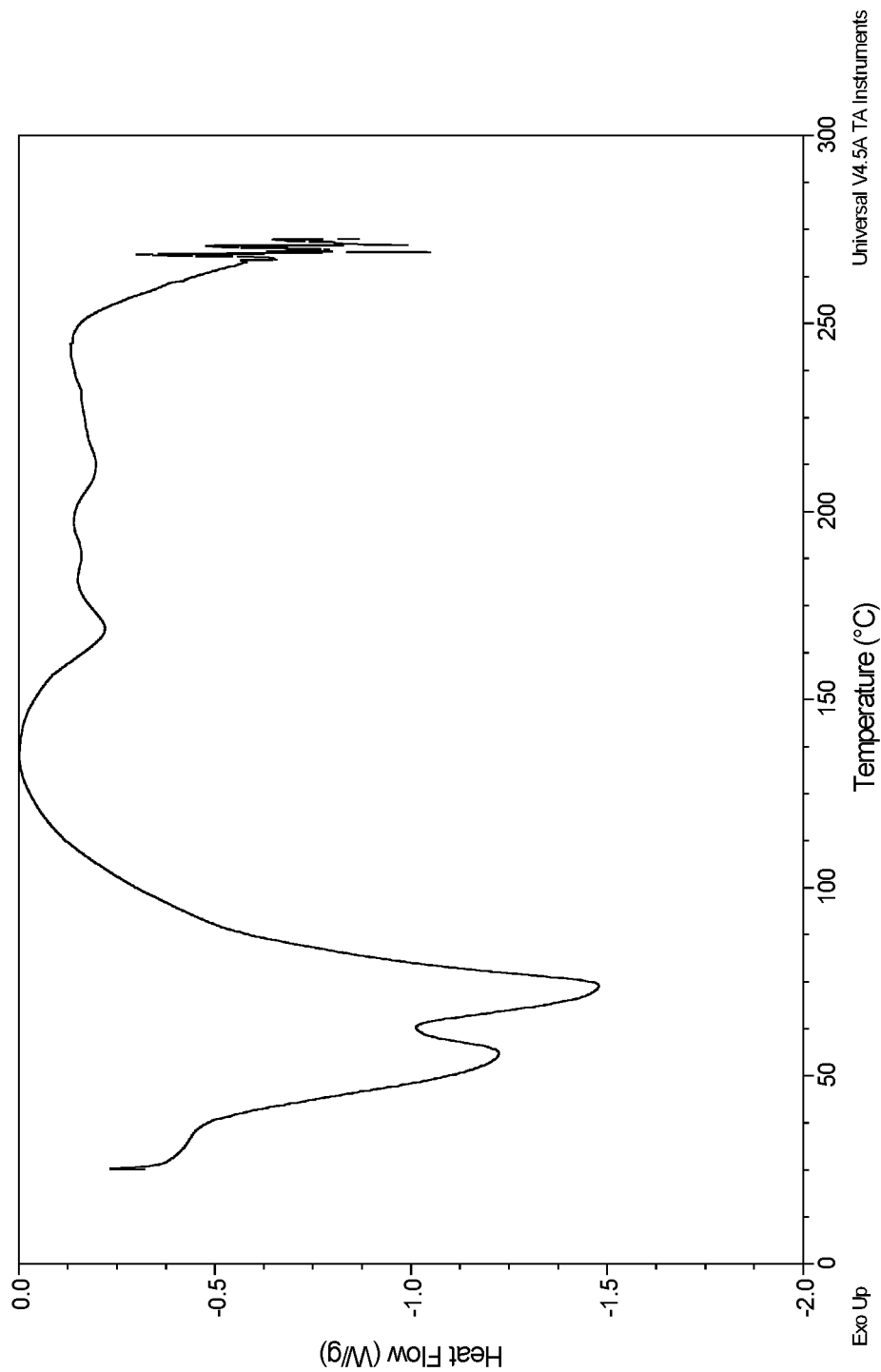
FIG. 7 shows results from DSC of squalamine phosphate, Form 2 (from Example 4).

Into a 100 mL EasyMax vessel Squalamine Lactate solids (1.55 g, Example 3) was dissolved in 1:1 v/v EtOH/water (62 mL) and 2.2 equiv of 2 N NaOH (2.11 mL) at 20° C. The batch was heated to 35° C. 0.2 M $H_3PO_4$ (4 mL out of 9 mL) was added at 35° C. over 10 min. The resulting clear solution was heated to 45° C., the remaining 5 mL 0.2 M $H_3PO_4$ was added at the rate of 2 mL/h by a syringe pump. After a total 5.2 mL of acid was charged, the mixture turned cloudy, and the acid addition was paused. Seed (5 mg, squalamine phosphate-form 1) was added in one portion. A thin slurry generated gradually. The acid addition was resumed until all 9 mL of 0.2 M $H_3PO_4$ was charged. The ending pH was 7.5. After the slurry was cooled from 45° C. to 20° C. over 2 h, the mixture was aged at 20° C. for 16 h (overnight). The slurry sample gave flake shape by PLM. The product was isolated by filtration, the wet cake was washed with acetone 2×10 mL. The wet cake was dried under vacuum at RT for 30 min, wet cake sample 99.93:0.07 ratio of 313:3-a by HPLC. Squalamine Phosphate was obtained as white solid (1.21 g). XRPD pattern of the isolated solids conforms to that of Form 2 (FIG. 5). TGA and DSC results of the product are shown in FIG. 6 and FIG. 7, respectively.

$^1$H and $^{31}$P NMR studies using phenylphosphonic acid as an internal reference indicated that the molar ratio of squalamine and phosphoric acid is roughly 1.0:0.9.

Example 5

Preparation of Squalamine Phosphate (Form 1) from Squalamine Lactate

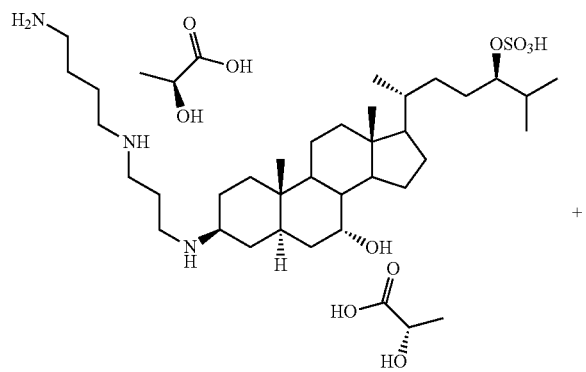

MSI-1256F
Squalamine-dilactate
$C_{40}H_{77}N_3O_{11}S$
MW: 808.12

+

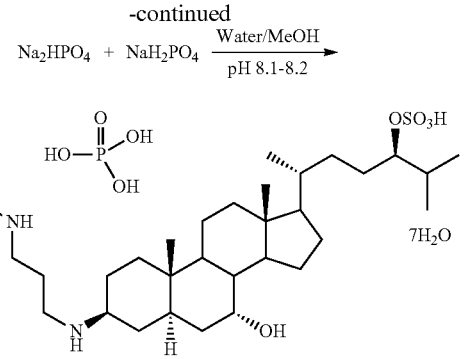

ENT-01
Squalamine-Phosphate-7H$_2$O
$C_{34}H_{82}N_3O_{16}PS$
MW: 852.06

+2 NaO

Sodium lactate
$C_3H_5NaO_3$
MW: 112.06

Figure 11:
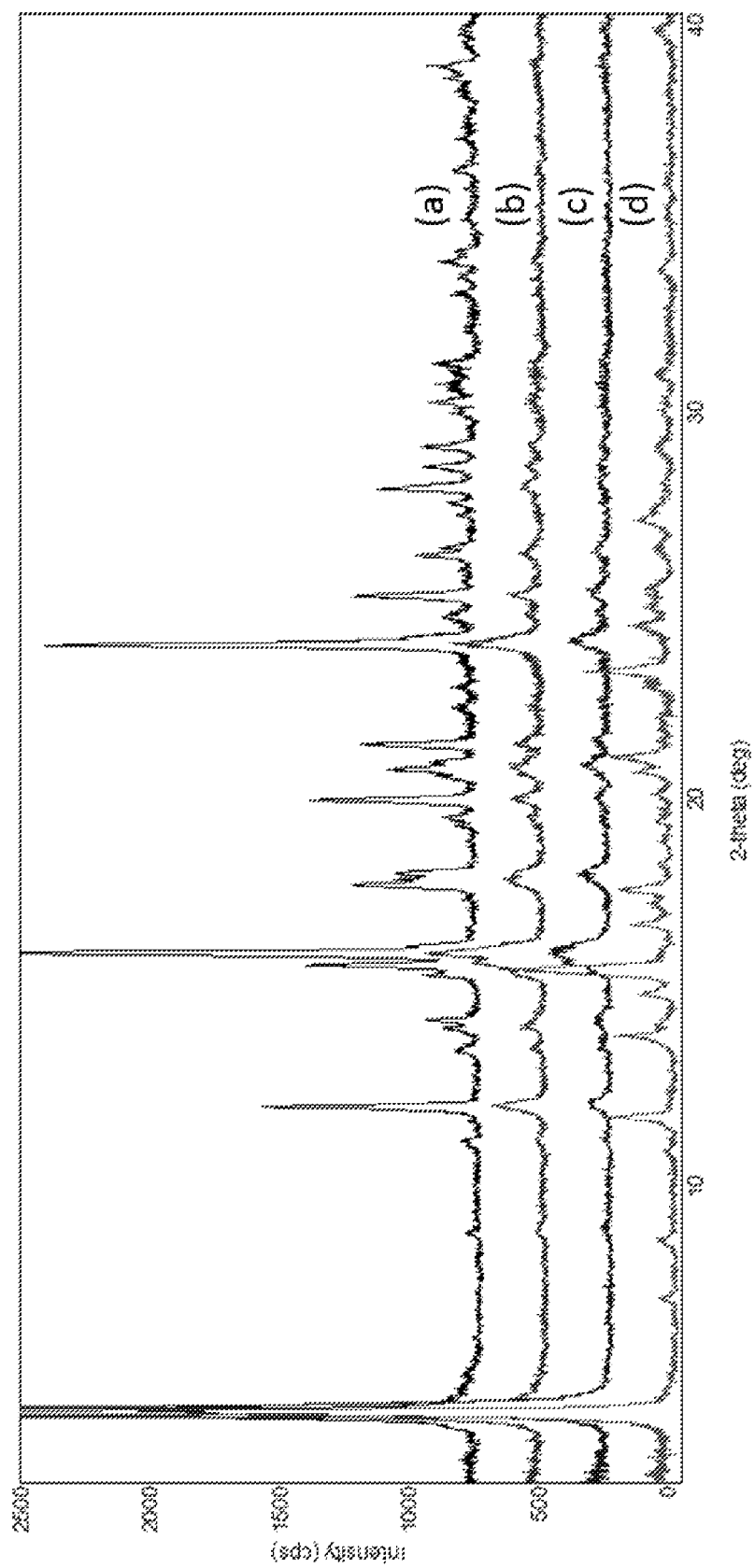
FIG. 11 shows XRPD patterns of squalamine phosphate samples of (a) Form 1 (Example 5), (b) after water-acetone wash of Form 2, (c) after water-ethanol wash of Form 2, and (d) Form 2 (Example 2, after crystallinity upgrade). The $H_2O$-acetone and $H_2O$-EtOH washed samples match Form 1 (i.e., Form 2 converted to Form 1).

A 100-L reactor was equipped with a thermocouple, a nitrogen inlet, a condenser, an addition funnel and a thermal regulation unit. A pre-prepared solution of water (26.5 L), sodium phosphate dibasic (397.0 g, 2.797 mol), and sodium phosphate monobasic (16.0 g, 0.133 mol) was transferred into the 100-L Reactor via a PTFE tubing attached in-line with a 0.2 or 0.4-micron filter cartridge. The contents of the 100 L Reactor were agitated under nitrogen at 25±5° C. at 125-250 RPM, resulting in a clear solution. A pH meter was standardized and then the pH of the phosphate buffer stirring in the 100 L Reactor was determined which was found to be at pH 8.1. Water (13.2 L) and methanol (26.5 L) were added and resulting mixture was heated to 60±5° C. over a period of 1.5 to 3.0 h. A solution of squalamine lactate (264.0 g, 0.327 mol) and methanol (1.32 L) was prepared and transferred into the addition funnel atop the 100 L Reactor via a PTFE tubing attached in-line with a 0.2 or 0.4-micron filter cartridge. The squalamine lactate/MeOH solution in the addition funnel was slowly transferred into the 100 L reactor over a period of 20-25 min while maintaining the temperature at 60±5° C. After the addition was over, the resulting cloudy mixture was heated to 70±5° C. to obtain a near clear solution which contained trace amounts of suspended particles. Heating was continued for at least an hour after which heating was turned off and the batch was allowed to cool to ambient temperature over several hours. The batch was then stirred over night at room temperature. The resulting white suspension was filtered and the cake was dried on the filter funnel until nearly no filtrate could be observed. The resulting white cake was washed with acetone (2×5.3 L). The washed cake was then put under a blanket of nitrogen and vacuum was pulled until nearly no filtrate could be observed. The wet cake was placed in a vacuum oven and dried over night at 25±5° C. under 5-125 torr pressure and Nitrogen purge of 2-10 mL/min. The drying was continued until a constant weight was achieved resulting in a total of 233.9 g (84.1% yield) of squalamine phosphate heptahydrate as white solid which was found to be 98.8 A % by HPLC (CAD) analysis and contained 11.5 wt. % H$_2$O (Theory=14.79% for heptahydrate) as determined by KF analysis. The XRPD analysis (FIG. 8, select peaks shown in Table 2) indicated that the isolated squalamine phosphate is crystalline in nature. This crystal form of squalamine phosphate was labelled Form 1. Results from DSC and TGA are shown in FIG. 10 and FIG. 11, respectively.

XRPD Analysis (Instrument: Rigaku MiniFlex 600):
Parameters: X-Ray tube Cu (Kα); tube voltage 40 kV; tube current 15 mA
- Soller (Inc.) 2.5 deg.; IHS 10.0 mm; DS 1.250 deg.; SS 1.250 deg.;
- Soller (rec.) 2.5 deg.; RS 0.15 mm; monochromatization KB filter (X1)
- Scan from 2 to 40 degrees 2-theta; 0.01 degrees/step; scan rate 2 degrees/min.

TABLE 2

Select peaks from XRPD pattern of squalamine phosphate (Form 1)

| No. | 2-theta (degrees) | Rel. intensity | Rel. height |
|---|---|---|---|
| 1 | 3.9 | 100 | 100 |
| 2 | 11.7 | 8.79 | 9.13 |
| 3 | 14.0 | 2.59 | 1.29 |
| 4 | 15.1 | 2.56 | 2.04 |
| 5 | 15.4 | 6.72 | 7.44 |
| 6 | 15.7 | 23.78 | 23.15 |
| 7 | 17.4 | 3.53 | 4.48 |
| 8 | 17.8 | 6.81 | 3.01 |
| 9 | 19.7 | 6.4 | 7.18 |
| 10 | 20.5 | 6.48 | 4.01 |
| 11 | 21.1 | 4.06 | 5.15 |
| 12 | 23.7 | 21.55 | 21.35 |
| 13 | 24.9 | 4.8 | 5.01 |
| 14 | 26.0 | 2.96 | 2.55 |
| 15 | 27.7 | 4.14 | 4.31 |
| 16 | 28.3 | 1.83 | 2.05 |
| 17 | 28.8 | 1.9 | 2.27 |

Example 6

Interconversions Between Form 1 and Form 2 of Squalamine Phosphate

Characterization of squalamine phosphate solids showed that a) there are two crystalline hydrated forms of squalamine phosphate (Form 1 and Form 2), and b) Form 1 is a lower hydrate (6-8% water) while Form 2 is a higher hydrate (9-12% water) by thermogravimetric analysis.

Washing Form 2 with water followed by acetone or ethanol wash and subsequent drying at 40° C. generates Form 1. When Form 2 was slurred in dry ethanol at 30° C. it also converted to Form 1. In addition Form 1 was also obtained by treating Form 2 at low humidity (27% RH), while at high humidity (70% RH) Form 2 remained the same.

The critical water activity in EtOH slurries also has been investigated in terms of the relative stability of ENT-01 Forms 1 and 2. The results indicate that a) Form 1 is more stable than Form 2 at or below 0.5 $A_w$, and, b) Form 2 more stable than Form 1 at $A_w$ levels 0.6 and above.

Overall, the data indicate that Form 2 is favored at high water content in slurry or high humidity in air, while Form 1 is more stable at lower humidity or low water content.

A. Relative Form Stability of ENT-01 Form 1 vs. Form 2

Form 1 and Form 2 are both hydrates with variable water content. From TGA analysis Form 1 samples showed weight losses in the range of 6-8% while Form 2 samples had weight losses in the range of 9-12%. In this study the relative stability of the two Forms was compared under different conditions. Results are summarized in Table 3.

Procedure 1: Water-Acetone and Water-Ethanol Wash

Two small portions of Form 2 (~100 mg each) were prepared in sample vials. The first one was slurried in water briefly followed by filtration and acetone wash. The second one was slurried in water briefly, filtered and washed with ethanol. Both samples were then oven dried at 40° C. overnight and analyzed by XRPD (FIG. 11).

Procedure 2: Low (27% RH) and High (70% RH) Humidity Conditioning

Figure 12:
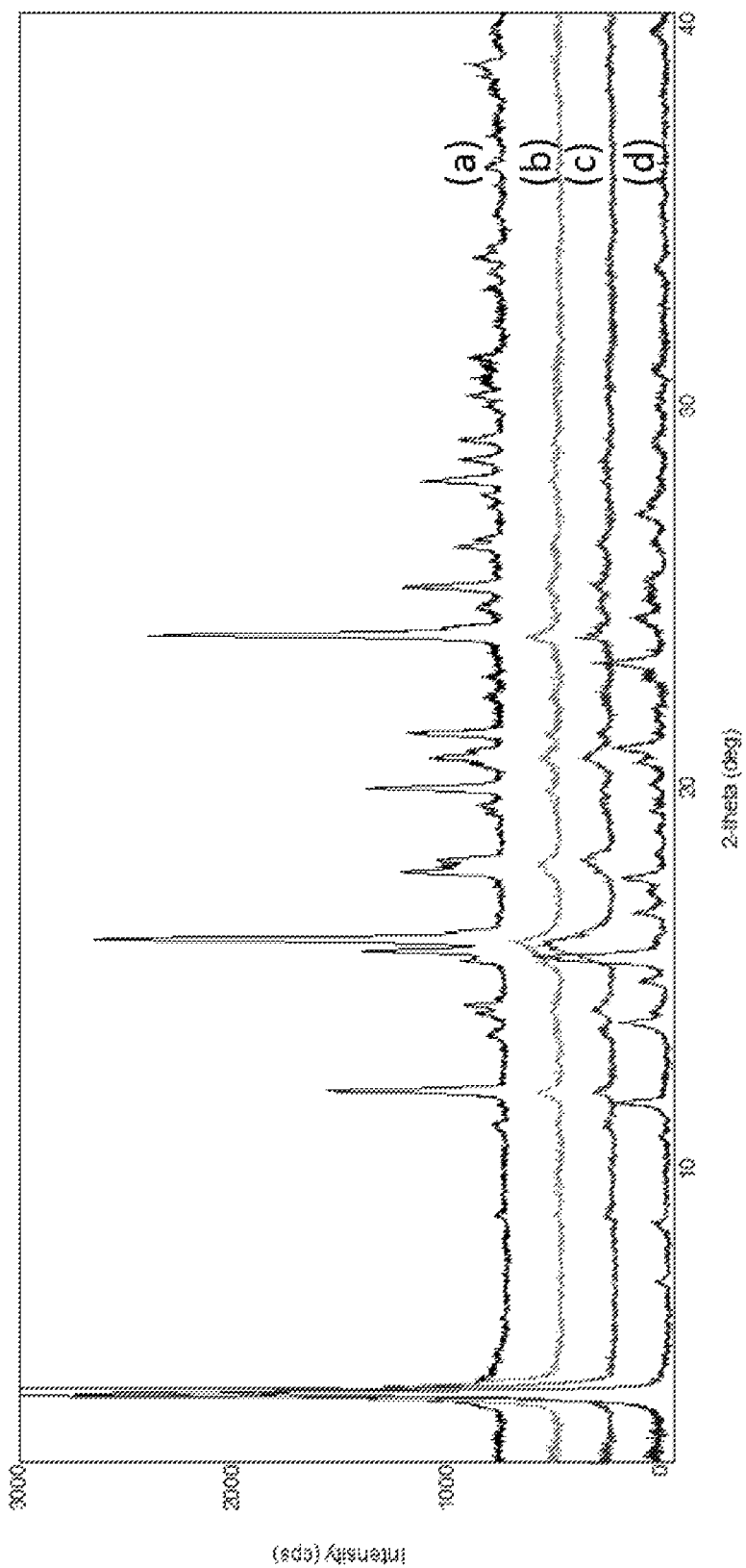
FIG. 12 shows XRPD patterns of squalamine phosphate samples of (a) Form 1 (Example 5), (b) Form 1 sample after 21° C., 27% RH conditions (c) Form 2 sample after 21° C., 27% RH conditions, (d) Form 2 (Example 2, after crystallinity upgrade). The low humidity treated Form 2 sample converted to Form 1, while Form 1 under the same conditions remained the same form.
Figure 13:
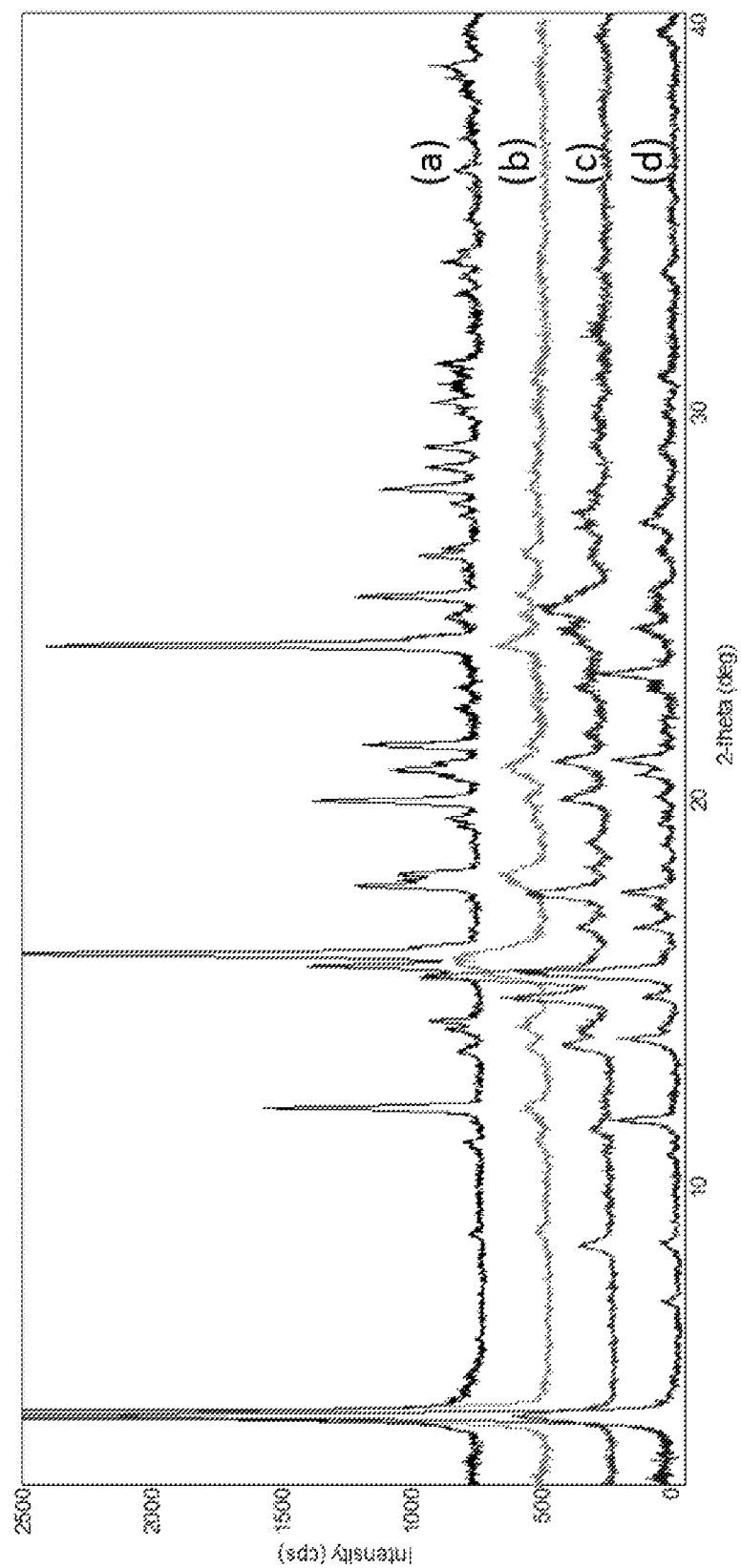
FIG. 13 shows XRPD patterns of squalamine phosphate samples of (a) Form 1 (Example 5), (b) Form 1 sample after 21° C., 70% RH conditions, (c) Form 2 sample after 21° C., 70% RH conditions, (d) Form 2 (Example 2, after crystallinity upgrade). At high humidity both samples remained the same as their respective starting forms.

One sample each of Form 1 and Form 2 on XRPD plates (~10 mg each) were exposed to 21° C. 27% RH and 21° C. 70% RH for one and two days, respectively. The four samples were analyzed by XRPD (FIG. 12 and FIG. 13).

Procedure 3: Dry Ethanol Slurry at 30° C.

Figure 14:
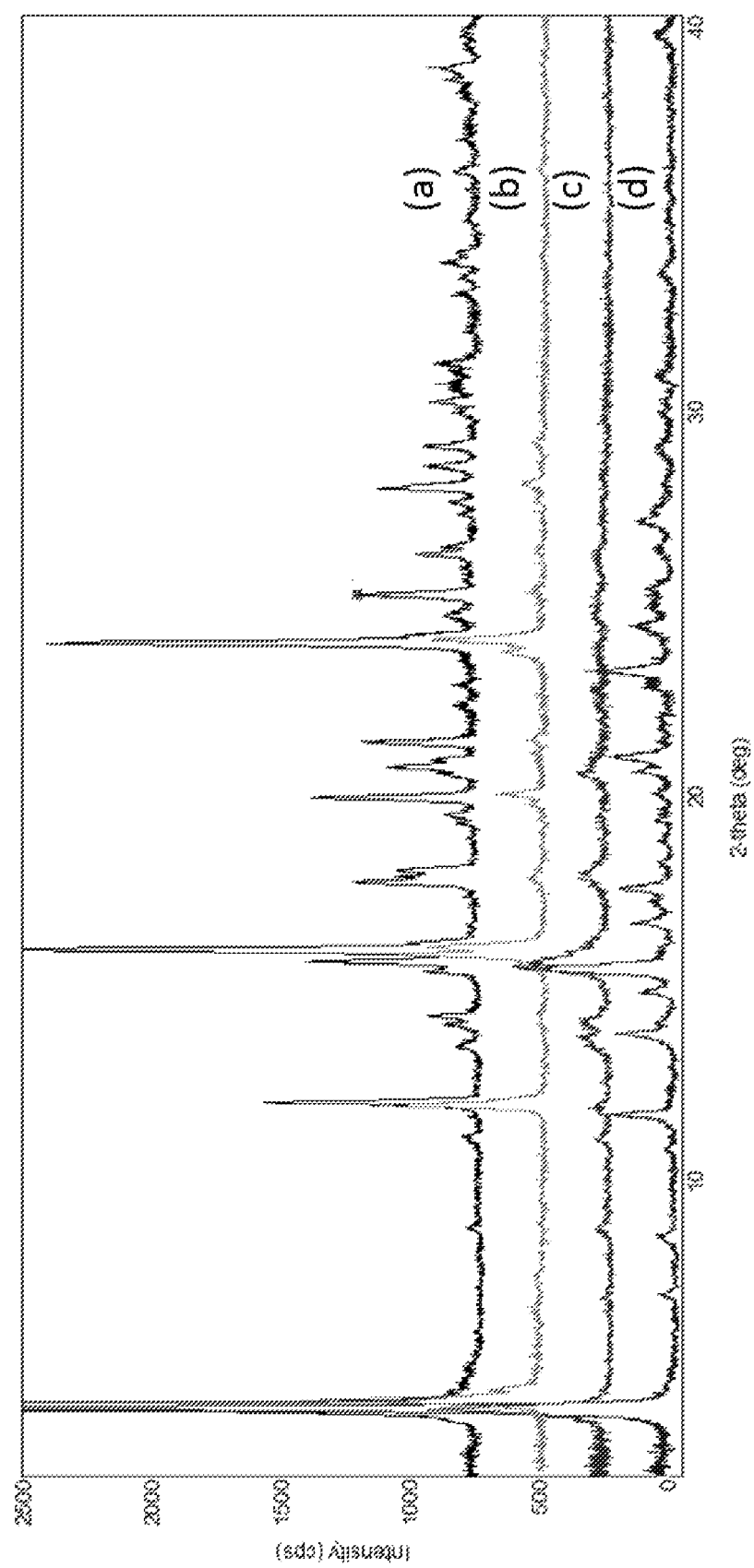
FIG. 14 shows XRPD patterns of squalamine phosphate samples of (a) Form 1 (Example 5), (b) Form 1 sample in dry EtOH at 30° C., (c) Form 2 sample in dry EtOH at 30° C., and (d) Form 2 (Example 2, after crystallinity upgrade). Both EtOH slurries have similar XRPD patterns to Form 1 (Example 5); in dry EtOH, Form 2 converted to Form 1.

A small portion of Form 1 (~50 mg) and a small portion of Form 2 (~50 mg) were prepared in scintillation vials and equal volumes of sieve dried ethanol was added, the slurries were conditioned overnight in a shaker at 30° C. The wet slurries were analyzed by XRPD (FIG. 14).

TABLE 3

Squalamine Phosphate Form Stability Study Summary from at pre-set % RH levels and in dry Ethanol

| Sample description | Condition | Duration | Final Form by XRPD |
|---|---|---|---|
| Form 2 | Water-acetone wash + 40° C. dry | overnight | Form 1 |
| | Water-ethanol wash + 40° C. dry | | |
| Form 1 | 21° C., 27% RH | | |
| Form 2 | | | |
| Form 1 | 21° C., 70% RH | Two nights | Form 1 |
| Form 2 | | | Form 2 |
| Form 1 | Slurry in dry ethanol at 30° C. | Overnight | Form 1 |
| Form 2 | | | |

The results from these three tests indicate that Form 1 is favored under low water content in slurry or low humidity in air, and Form 2 is more stable at higher humidity and/or water content.

B. Critical Water Activity for Relative Form Stability of ENT-01 Forms 1 and 2

For robust isolation of desired squalamine phosphate crystal form, critical water activity in EtOH has been investigated in terms of the relative stability of ENT-01 Forms 1 and 2. The procedure is detailed below.

Procedure: 0.1 to 0.9 Water Activity ($A_w$) in Ethanol

Nine samples of each Form 1 and Form 2 separately (~25 mg each) were prepared in scintillation vials. To each vial ½ mL of ethanol with water activity levels from 0.1 to 0.9 were added and the vials were let to condition in a shaker at 25° C. for 2-3 days. Similarly, six mixed samples of Form 1 and 2 were prepared and slurry conditioned at water activity levels of 0.1 to 0.6 in ethanol at 25° C. The wet cakes of each slurry were analyzed by XRPD.

The slurries post conditioning were analyzed by XRPD. The results are summarized in Table 4, showing the following key observations:

The Form 1 slurries in Ethanol at water activity levels of 0.1 to 0.6 at 25° C. stayed the same Form for three days. The XRPD patterns match that of Form 1.

Form 1 slurries in Ethanol at water activity levels of 0.7 to 0.9 at 25° C. all converted to Form 2 in three days.

The three day Form 2 slurries in Ethanol at water activity levels of 0.1 to 0.3 at 25° C. converted to Form 1. The XRPD patterns match that of Form 1.

Form 2 slurries in Ethanol at water activity levels of 0.4 to 0.9 at 25° C. stayed the same Form 2 for three days. The XRPD patterns match that of Form 2.

The seven day mixed Form 1 and 2 slurries in Ethanol at water activity levels of 0.1 to 0.5 $A_w$ at 25° C. converted to Form 1. The XRPD patterns match that of Form 1.

Seven day slurry of Form 1 and 2 in Ethanol at water activity level of 0.6 $A_w$ at 25° C. converted to Form 2 after two days. The XRPD pattern matches that of Form 2.

From these data, it can be summarized that Form 1 is stable at water activity levels at or lower than 0.5 $A_w$ in ethanol. And, Form 2 will be stable at $A_w$ levels 0.6 and above.

TABLE 4

Squalamine Phosphate Form Stability Study at 0.1 to 0.9 Critical Water Activity in Ethanol at 25° C.

| Sample Description | Water Activity $A_w$ | Water Volume Fraction | Duration | Final Form by XRPD |
|---|---|---|---|---|
| Form 1 + Form 2 | 0.000 | 0.000 | Three days | Form 1 |
| Form 1 + Form 2 | 0.099 | 0.013 | | |
| Form 1 + Form 2 | 0.205 | 0.030 | | |
| Form 1 + Form 2 | 0.298 | 0.048 | | |
| Form 1 + Form 2 | 0.398 | 0.073 | | Form 1 + Form 2 |
| Form 1 + Form 2 | 0.502 | 0.104 | | Form 1 + Form 2 |
| Form 1 + Form 2 | 0.605 | 0.145 | | Form 1 Form 2 |
| Form 1 + Form 2 | 0.700 | 0.198 | | Form 2 |
| Form 1 + Form 2 | 0.802 | 0.296 | | |
| Form 1 + Form 2 | 0.900 | 0.550 | | |
| Form 1 + 2 | 0.099 | 0.013 | Seven days | Form 1 |
| | 0.205 | 0.030 | | |
| | 0.298 | 0.048 | | |
| | 0.398 | 0.073 | | |
| | 0.502 | 0.104 | | |
| | 0.605 | 0.145 | | Form 2 |

Example 7

Preparation and Coating of Squalamine Phosphate Tablets

A blend was prepared by combining 518.6 g of Prosolv SMCC HD 90 (JRS Pharma), 13.4 g of Ac-Di-Sol SD-711 (FMC), 1.33 g of Aerosil 200 (Evonik), 3.4 g of magnesium stearate (Malinckrodt), and 135.8 g of squalamine phosphate Form 1 in a V-blender during 10 min to yield 667.6 grams of material (99%). This blend was added to the hopper of a tablet press. The target tablet parameters were a weight of 125 mg, thickness of 4.15 mm, hardness of 12 kp, and friability of NMT 1.0%. The die fill amount and compression parameters were set to achieve tablet requirements (Fill weight of 9.85, turret speed of 20 RPM, main compression of 5.8, and average upper compression of 2.5 KN). Using these parameters, 10 sample tablets were prepared that met required properties. The tableting process was initiated and tablets meeting requirements were collected (609.3 g, 91%).

Sterile water (1200 g) was added to a stainless-steel container equipped with a mixing blade adjusted to a suitable vortex without pulling air into the liquid. Opadry, II white (300.5 g) was added to the vortex and the mixer speed was adjusted to maintain a vortex during and after addition. Mixing was continued for a minimum of 45 min until a uniform suspension formed (133 min total). The target coating was a 4% weight gain to the squalamine phosphate tablets, which translated to a need for 217.6 grams of the suspension for 609.3 g of tablets. This was based on 20% of the coating solid and 56% efficiency of coating. The spray gun was loaded with the coating mixture and the squalamine phosphate tablets were loaded in the coating pan at 5.0 inches from the spray gun nozzle. Pre-heat time was set at 6 min 30 sec, spray rate at 4 g/min, pan speed at 15 rpm, inlet temperature at 60-75° C., exhaust temperature at 45-50° C., bed temperature at 45-50° C., atomization at 20 psi, and process air at 150 cfm. Spraying was begun and continued until the theoretical amount of 217.6 grams of coating suspension was applied. The pan speed was reduced to 3 rpm and the inlet temperature reduced to 0° C. in order to dry the tablets over 10 min. The coated tablets were collected and weighed to yield 626.9 g (99%) of coated squalamine phosphate tablets.

The coated squalamine phosphate tablets (10 per bottle) were stored in 30 cc HDPE bottles with 28 mm SecuRX foil sealed caps.

TABLE 5

Coated squalamine phosphate tablets met the following key specifications at Day 0 and at 3 months

| Test | Appearance | Assay by HPLC | Related Substances | Dissolution | Moisture |
|---|---|---|---|---|---|
| Criteria | White to off-white round tablet | 90.0-110.0% of label claim | Total Impurities NMT 4% | Q = 75% at 45 minutes | Report |
| Initial | Conforms | 100.3% | 1.7% | 101% | 4.39% |
| 3 months at 25° C., 60% RH | Conforms | 102.7 | 1.7% | 94% | 5.44% |

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof, inclusive of the endpoints. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. An isolated squalamine phosphate solid form designated as Form 2, which is at least 95% purified and having the following:
   (a) an X-ray powder diffraction pattern comprising a peak, in terms of 2-theta, at about 15.2° and at about 22.9°;
   (b) an X-ray powder diffraction pattern as shown in FIG. 15 with ±0.2°;
   (c) a differential scanning calorimetry (DSC) thermogram comprising an endothermic peak at about 90.9° C.;
   (d) a differential scanning calorimetry (DSC) thermogram as shown in FIG. 16 with ±0.4° C.;
   (e) a thermogravimetric analysis (TGA) as shown in FIG. 17 with ±0.4% weight; and/or
   an X-ray powder diffraction pattern comprising the following peaks: at about 11.4° 2-theta, at about 15.2° 2-theta and at about 22.9° 2-theta, as determined on a diffractometer using Cu-Kα radiation at a wavelength of 1.5406 Å.

2. The squalamine phosphate solid form of claim 1 having:
   (a) a water content of about 9-12%; or
   (b) a water content of more than about 9%.

3. A pharmaceutical composition comprising the solid form of squalamine phosphate designated as Form 2 according to claim 1 and a pharmaceutically acceptable carrier.

4. The pharmaceutical composition of claim 3, comprising at least about 90% by weight of the solid form of squalamine phosphate designated as Form 2.

5. The pharmaceutical composition of claim 3, additionally comprising a solid form of squalamine phosphate designated as Form 1.

6. A process for preparing the squalamine phosphate solid form of claim 1, the process comprising:
   (a) dissolving squalamine lactate in base, water, and alcohol to form a first solution;
   (b) heating the first solution to a first elevated temperature, wherein the first elevated temperature is greater than 25° C.;
   (c) adding a first amount of phosphoric acid ($H_3PO_4$) to the first solution to form a second solution;
   (d) heating the second solution to a second elevated temperature higher than the first elevated temperature;
   (e) adding a second amount of $H_3PO_4$ to the second solution;
   (f) obtaining a slurry; and
   (g) isolating the squalamine phosphate solid form.

7. The process of claim 6, comprising one or more of the following:
   (a) the base is sodium hydroxide;
   (b) the alcohol is ethanol;
   (c) the first elevated temperature is at least about 35° C.;
   (d) the second elevated temperature is at least about 45° C.;
   (e) the step of obtaining the slurry comprises seeding the mixture with Form 1 seeds;
   (f) the step of obtaining the slurry comprises adding a third amount of $H_3PO_4$ to the second solution;
   (g) the step of obtaining the slurry comprises cooling the second solution;
   (h) the process further comprises aging the slurry prior to the isolating step; and/or
   (i) the isolating step comprises filtering the slurry and washing filtered solids with acetone.

8. A squalamine phosphate solid form designated as Form 2 prepared by the process of claim 7, wherein the squalamine phosphate solid form is at least 95% purified and have:
   (a) an X-ray powder diffraction pattern comprising a peak, in terms of 2-theta, at about 15.2° and at about 22.9°;
   (b) an X-ray powder diffraction pattern as shown in FIG. 15 with ±0.2°;
   (c) a differential scanning calorimetry (DSC) thermogram comprising an endothermic peak at about 90.9° C.;
   (d) a differential scanning calorimetry (DSC) thermogram as shown in FIG. 16 with ±0.4° C.; and/or
   (e) a thermogravimetric analysis (TGA) as shown in FIG. 17 with ±0.4% weight.

* * * * *